United States Patent [19]

Gazzano-Santoro et al.

[11] Patent Number: 5,731,415

[45] Date of Patent: Mar. 24, 1998

[54] LIPOPOLYSACCHARIDE BINDING PROTEIN DERIVATIVES

[75] Inventors: Héléne Gazzano-Santoro, San Bruno; Georgia Theofan, Torrance; Patrick W. Trown, Danville, all of Calif.

[73] Assignee: XOMA Corporation, Berkeley, Calif.

[21] Appl. No.: 261,660

[22] Filed: Jun. 17, 1994

Related U.S. Application Data

[63] Continuation-in-part of Ser. No. 79,510, Jun. 17, 1993, abandoned.

[51] Int. Cl.$^6$ .......................... A61K 38/17; C07K 19/00; C12N 15/00; C12N 15/09
[52] U.S. Cl. .................. 530/350; 435/240.2; 435/252.3; 435/320.1; 514/8; 530/395; 536/234; 536/23.5
[58] Field of Search .............................. 435/69.1, 240.2, 435/252.3, 320.1; 935/60, 66; 536/23.4, 23.5; 530/387.7, 350, 395; 514/8

[56] References Cited

U.S. PATENT DOCUMENTS

| | | | |
|---|---|---|---|
| 5,089,274 | 2/1992 | Marra et al. | 424/534 |
| 5,171,739 | 12/1992 | Scott | 514/12 |
| 5,198,541 | 3/1993 | Elsbach et al. | 435/69.1 |
| 5,234,912 | 8/1993 | Marra et al. | 514/21 |
| 5,245,013 | 9/1993 | Ulevitch et al. | 530/380 |
| 5,308,834 | 5/1994 | Scott et al. | 514/12 |
| 5,334,584 | 8/1994 | Scott et al. | 514/12 |
| 5,348,942 | 9/1994 | Little, II et al. | 514/12 |

FOREIGN PATENT DOCUMENTS

| | | |
|---|---|---|
| WO 91/01639 | 2/1991 | WIPO . |
| WO 92/03535 | 3/1992 | WIPO . |
| WO 92/09621 | 6/1992 | WIPO . |
| WO 93/05797 | 4/1993 | WIPO . |
| WO 93/06228 | 4/1993 | WIPO . |
| WO 93/23434 | 11/1993 | WIPO . |
| WO 93/23540 | 11/1993 | WIPO . |
| WO 94/17819 | 8/1994 | WIPO . |
| WO 94/18323 | 8/1994 | WIPO . |
| WO 94/20128 | 9/1994 | WIPO . |
| WO 94/20129 | 9/1994 | WIPO . |

OTHER PUBLICATIONS

Little et al., "Functional Domains of Recombinant Bactericidal/Permeability Increasing Protein (rBPI$_{23}$)*" *J. Biol. Chem.* 269:1865–1872 (1994).
Bazil et al., "Biochemical characterization of a soluble form of the 53–kDa monocyte surface antigen", *Eur. J. Immunol.*, 16:1583–1589 (1986).
Beekhuizen et al., "CD14 Contributes to the Adherence of Human Monocytes to Cytokine–Stimulated Endothelial Cells", *J. Immunol.*, 147(11):3761–3767 (Dec. 1, 1991).
Bevilacqua et al., "Interleukin 1 Acts on Cultured Human Vascular Endothelium to Increase the Adhesion of Polymorphonuclear Leukocytes, Monocytes, and Related Leukocyte Cell Lines", *J. Clin. Invest.*, 76:2003–2011 (Nov. 1985).
Bevilacqua et al., "Identification of an inducible endothelial–leukocyte adhesion molecule", *Proc. Natl. Sci. USA*, 84:9238–9242 Bazil et al., Biochemical characterization of a soluble form of a 53–kDa monocyte surface antigen, *Eur. J. Immunol.*, 16:1583–1589 (1986).
Bone, "The Pathogenesis of Sepsis", *Annals Int. Med.*, 115:457–469 (1991).
Frey et al., "Soluble CD14 Participates in the Response of Cells to Lipopolysaccharide", *J. Exp. Med.*, 176:1665–1671 (Dec. 1992).
Gamble et al., "Stimulation of the adherence of neutrophils of umbilical vein endothelium by human recombinant tumor necrosis factor", *Proc. Natl. Acad. Sci. USA*, 82:8667–8671 (December 1985).
Gazzono–Santoro et al., "High–Affinity Binding of the Bactericidal/Permeability–Increasing Protein and a Recombinant Amino–Terminal Fragment to the Lipid A Region of Lipopolysaccharide", *Infect. Immun.*, 60(11):4754–4761 (Nov. 1992).
Gray et al., "Cloning of the cDNA of a Human Neutrophil Bactericidal Protein", *J. Biol. Chem.*, 264(16):9505–9509 (Jun. 5, 1989).
Han et al., "Lipopolysaccharide (LPS) Binding Protein, Truncated at the Ile–197, Binds LPS but does not Transfer LPS to CD14", *J. Biol. Chem.*, 269(11):8172–8175 (Mar. 18, 1994).
Larrick et al., "Complementary DNA Sequence of Rabbit CAP18—A unique Lipopolysaccharide Binding Protein", *Biochem. and Biophysical Res. Comm.*, 179(1):170–175 (Aug. 30, 1991).
Leatherbarrow, "Using linear and non–linear regression to fit biochemical data", *TIBS*, 15:455–458 (Dec. 1990).
Mannion et al., "Preferential Binding of the Neutrophil Cytoplasmic Granule–Derived Bactericidal/Permeability Increasing Protein to target Bacteria", *J. Immunol.*, 142(8):2807–2812 (Apr. 15, 1989).
Merrifield, "Instrument for Automated Synthesis of Peptides", *Anal Chem.*, 38(13):1905–1914 (Dec. 1966).
Merrifield, "Solid Phase Peptide Synthesis. I. The Synthesis of a Tetrapeptide", *J. Am. Chem. Soc.*, 85:2149–2154 (Jul 20, 1963).
Moore et al., "Endotoxin Enhances Tissue Factor and Suppresses Thrombomodulin Expression of Human Vascular Endothelium In Vitro", *J. Clin. Invest.*, 79:124–130 (Jan. 1987).

(List continued on next page.)

*Primary Examiner*—Vasu S. Jagannathan
*Assistant Examiner*—David S. Romeo
*Attorney, Agent, or Firm*—Marshall, O'Toole, Gerstein, Murray & Borun

[57] ABSTRACT

Disclosed are novel biologically active lipopolysaccharide binding protein (LBP) derivatives including LBP derivative hybrid proteins which are characterized by the ability to bind to and neutralize LPS and which lack the CD14-mediated immunostimulatory properties of holo-LBP.

10 Claims, 25 Drawing Sheets

OTHER PUBLICATIONS

Morrison and Ulevitch, "The Effects of Bacterial Endotoxins on Host Mediation Systems", *Am. J. Pathol.*, 93:527–618 (1978).

Ooi et al., "Endotoxin–neutralizing Properties of the 25 kD N–Terminal Fragment and a Newly Isolated 30 kD C–Terminal Fragment of the 55–60 kD Batericidal/Permeability–increasing Protein of Human Neutrophils", *J. Exp. Med.*, 174:649–655 (Sep. 1991).

Pohlman et al., "An Endothelial Cell Surface Factor)s) Induced In Vitro by Lipopolysaccharide, Interleukin 1, and Tumor Necrosis Factor–α Increases Neutorphil Adherence by a CDw18–Dependent Mechanism", *J. Immunol.*, 136(12):4548–4553 (Jun. 15, 1986).

Pugin et al., "lipopolysaccharide activation of human endothelial and epithelial cells is mediated by lipopolysaccaride–binding protein and soluble CD14", *Proc. Natl. Acad. Sci. USA.*, 90:2744–2748 (Apr. 1993).

Rogy et al., "The Role of Bactericidal/Permeability–Increasing Protien in the Treatment of Primate Bacteremia and Septic Shock", *J. Clin. Immunol.*, 14(2):120–133 (1994).

Schleimer and Rutledge., "Cultured Human Vascular Endothelial Cells Acquire Adhesiveness for Neutrophils after Stimulation with Interleukin 1, Endotoxin, and Tumor–Promoting Phorbol Diesters", *J. Immunol.*, 136(2):649–654 (Jan 15, 1986).

Schumann et al., "Structure and Function of Lipopolysaccharide Binding Protein", *Science*, 249:1429–1433 (Sep. 21, 1990).

Smith et al., "Recognition of an Endothelial Determinant for CD18–dependent Human Neutrophil Adherence and Transendothelial Migration", *J. Clin. Invest.*, 82:1746–1756 (1988).

Theofan et al., "An Amino–Terminal Fragment of Human Lipopolysaccharide–Binding Protein Retains Lipid A Binding but Not CD14–Stimulatory Activity", *J. Immunol.*, 154:3623–3629 (1994).

Weiss et al., "Purification and Characterization of a Potent Bactericidal and Membrane Active Protein from the Granules of Human Polymorphonuclear Leukocytes", *J. Biol. Chem.*. 253(8):2664–2672 (Apr. 1978).

Wigler et al., "Transfer of Purified Herpes Virus Thymidine Kinase Gene to Cultured Mouse Cells", *Cell*, 11:223–232 (May 1977).

Worthen et al., "Neutrophil Adherence Induced by Lipopolysaccharide In Vitro", *J. Clin Invest.*, 90:2526–2535 (Dec. 1992).

Wright et al., "Lipopolysaccharde (LPS) Binding Protein Opsonizes LPS–Bearing Particles for Recognition by a Novel Receptor on Macrophages", *J. Exp. Med.*, 170:1231–1241 (Oct. 1989).

Wright et al., "CD14 a Receptor for Complexes of Lipopolysaccharide (LPS) and LPS Binding Protein", *Science*, 249:1431–1433 (Sep. 21, 1990).

Wright et al., "Activation of the Adhesive Capacity of CR3 on Neutrophils by Endotoxin: Dependence on Lipopolysaccharide Binding Protein and CD14", *J. Exp. Med.*, 173:1281–1286 (May 1991).

Journal of Biological Chemistry vol. 263. No. 27, 25 Sep. 1988 pp. 13479–13481 Tobias et al.

Journal of Immunology vol. 144. No. 2, 15 Jan. 1990 pp. 662–666. Marra et al.

```
  1 GCC AAC CCC GGC TTG GTC GCC AGG ATC ACC GAC AAG GGA CTG CAG TAT GCG GCC
  1>Ala Asn Pro Gly Leu Val Ala Arg Ile Thr Asp Lys Gly Leu Gln Tyr Ala Ala

55 CAG GAG GGG CTA TTG GCT CTG CAG AGT GAG CTC CTG CTG AGG ATC ACG CTG GAC
 19>Gln Glu Gly Leu Leu Ala Leu Gln Ser Glu Leu Leu Leu Arg Ile Thr Leu Asp

109 TTC ACC GGG GAC TTG AGG ATC CCC CAC GTC GGC CGT GGG TAT GAG TAC TTC CAC
 37>Phe Thr Gly Asp Leu Arg Ile Pro His Val Gly Arg Gly Tyr Glu Tyr Phe His

163 AGC AAC ATC CAC AGC TGT GAG CTG CTT CAC CTC TCT GCG AGG CTG AGG CCT CCT
 55>Ser Asn Ile His Ser Cys Glu Leu Leu His Leu Ser Ala Leu Arg Pro Val Pro

217 GGC CAG GGC AGT CTC AGT CTC GAC TCC ATC CGG GTC CAG GGC AGG
 73>Gly Gln Gly Ser Leu Ser Leu Asp Ser Ile Arg Val Gln Gly Arg

271 TGG AAG GTG CGC AAG TCA TTC AAA TTC TTT CTA CAG GGC TCT TTT GAT GTC AGT GTC
 91>Trp Lys Val Arg Lys Ser Phe Lys Phe Phe Leu Gln Gly Ser Phe Asp Val Ser Val

325 AAG GGC ATC AGC ATT TCG GTC AAC CTC CTG TTG GGC GAG TCC TCC GGG AGG
109>Lys Gly Ile Ser Ile Ser Val Asn Leu Leu Leu Gly Ser Glu Ser Gly Arg

379 CCC ACA GTT ACT GCC TCC AGC AGT GAC AGT GAC ATC GCT GAC GTG GAG GTG GAC
127>Pro Thr Val Thr Ala Ser Ser Ser Asp Ser Asp Ile Ala Asp Val Glu Val Asp

433 ATG TCG GGA GAC TTG GGG TGG CTG TTG AAC CTC TTC CAC AAC CAG ATT GAG TCC
145>Met Ser Gly Asp Leu Gly Trp Leu Leu Asn Leu Phe His Asn Gln Ile Glu Ser

487 AAG TTC CAG AAA GTA CTG GAG AGC AGG ATT TGC GAA ATG ATC CAG AAA TCG GTG
146>Lys Phe Gln Lys Val Leu Glu Ser Arg Ile Cys Glu Met Ile Gln Lys Ser Val

541 TCC TCC GAT CTA CAG CCT TAT CTC CAA ACT CTG CCA GTT ACA ACA GAG ATT
181>Ser Ser Asp Leu Gln Pro Tyr Leu Gln Thr Leu Pro Val Thr Thr Glu Ile
```

FIGURE 1

```
  1 ATG GGG GCC TTG GCC AGA GCC CTG CCG TCC ATA CTG CTG GCA TTG CTG CTT

52 ACG TCC ACC CCA GAG GCT CTG GGT GCC AAC CCC GGC TTG GTC GCC AGG ATC
                                   1>Ala Asn Pro Gly Leu Val Ala Arg Ile

103 ACC GAC AAG GGA CTG CAG TAT GCG GCC CAG GAG GGG CTA TTG GCT CTG CAG
 10>Thr Asp Lys Gly Leu Gln Tyr Ala Ala Gln Glu Gly Leu Leu Ala Leu Gln

154 AGT GAG CTG CTC AGG ATC ACG CTG CCT GAC TTC ACC GGG GAC TTG AGG ATC
 27>Ser Glu Leu Leu Arg Ile Thr Leu Pro Asp Phe Thr Gly Asp Leu Arg Ile

205 CCC CAC GTC GGG CGT GGG CGC TAT GAG TTC CAC AGC CTG AAC ATC CAC AGC
 44>Pro His Val Gly Arg Gly Arg Tyr Glu Phe His Ser Leu Asn Ile His Ser

256 TGT GAG CTG CTT CAC TCT GCG CTG AGG CCT GTC CCT GGC CAG GGC CTG AGT
 61>Cys Glu Leu Leu His Ser Ala Leu Arg Pro Val Pro Gly Gln Gly Leu Ser

307 CTC AGC ATC TCC GAC TCC AGC AGC CAG GGC TCC CAG GGC AGG TGG AAG GTG CGC
 78>Leu Ser Ile Ser Asp Ser Ile Arg Gln Gly Val Gln Gly Arg Trp Lys Val Arg

358 AAG TCA TTC TTC AAA CTA CAG GGC TCC TTT GAT GTC AGT GTC AAG GGC ATC
 95>Lys Ser Phe Phe Lys Leu Gln Gly Ser Phe Asp Val Ser Val Lys Gly Ile

409 AGC ATT TCG AAC CTC CTG TTG GGG AGC GAG TCC TCC GGG AGG CCC ACA
112>Ser Ile Ser Asn Leu Leu Leu Gly Ser Glu Ser Ser Gly Arg Pro Thr

460 GTT ACT GCC TCC AGC AGT AGC GAT GCT TTC ATC GAC GTG GAG GTG GAC ATG
129>Val Thr Ala Ser Ser Ser Asp Ala Phe Ile Asp Val Ala Asp Val Glu Asp Met

511 TCG GGA GAC TTG GGG TGG CTG TTG AAC CTC TTC CAC CAG ATT GAG TCC
146>Ser Gly Asp Leu Gly Trp Leu Leu Asn Leu Phe His Gln Ile Glu Ser
```

FIGURE 2A

```
562  AAG TTC CAG AAA GTA CTG GAG AGC AGG ATT TGC GAA ATG ATC CAG AAA TCG
163> Lys Phe Gln Lys Val Leu Glu Ser Arg Ile Cys Glu Met Ile Gln Lys Ser

613  GTG TCC TCC GAT CTA CAG CCT TAT CTC CAA ACT CTG CCA GTT ACA ACA GAG
180> Val Ser Ser Asp Leu Gln Pro Tyr Leu Gln Thr Leu Pro Val Thr Thr Glu

664  ATT GAC AGT TTC GCC GAC ATT GAT TAT AGC TTA GTG GAA GCC CCT CGG GCA
197> Ile Asp Ser Phe Ala Asp Ile Asp Tyr Ser Leu Val Glu Ala Pro Arg Ala

715  ACA GCC CAG ATG CTG GAG GTG ATG TTT AAG GGT GAA ATC TTT CAT CGT AAC
214> Thr Ala Gln Met Leu Glu Val Met Phe Lys Gly Glu Ile Phe His Arg Asn

766  CAC CGT TCT CCA GTT ACC CTC CTT GCT GCA GTC ATG AGC CTT CCT GAG GAA
231> His Arg Ser Pro Val Thr Leu Leu Ala Ala Val Met Ser Leu Pro Glu Glu

817  CAC AAC AAA ATG GTC TAC TTT GCC ATC TCG GAT TAT GTC TTC AAC ACG GCC
248> His Asn Lys Met Val Tyr Phe Ala Ile Ser Asp Tyr Val Phe Asn Thr Ala

868  AGC CTG GTT TAT CAT GAG GAA GGA TAT CTG AAC TTC TCC ATC ACA GAT GAC
265> Ser Leu Val Tyr His Glu Glu Gly Tyr Leu Asn Phe Ser Ile Thr Asp Asp

919  ATG ATA CCG CCT AAT ATC CGA CTG ACC AAG ACC AAG TCC TTC CGA CCC
282> Met Ile Pro Pro Asn Ile Arg Leu Thr Lys Thr Lys Ser Phe Arg Pro

970  TTC GTC CCA CGG TTA GCC CTC TAC CCC AAC ATG AAC CTG GAA CTC CAG
299> Phe Val Pro Arg Leu Ala Leu Tyr Pro Asn Met Asn Leu Glu Leu Gln

1021 GGA TCA GTG CCC TCT GCT CCG CTC CTG AAC TTC AGC CCT GGG AAT CTG TCT
316> Gly Ser Val Pro Ser Ala Pro Leu Leu Asn Phe Ser Pro Gly Asn Leu Ser
```

FIGURE 2B

```
1072 GTG GAC CCC TAT ATG GAG ATA GAT GCC TTT GTG CTC CTG CCC AGC TCC AGC
333>Val Asp Pro Tyr Met Glu Ile Asp Ala Phe Val Leu Leu Pro Ser Ser Ser

1123 AAG GAG CCT GTC TTC CGG GTG AGT CTC CGG GCC ACT GTG TCC GCC ACC TTG
350>Lys Glu Pro Val Phe Arg Val Ser Leu Arg Ala Thr Val Ser Ala Thr Leu

1174 ACC TTC AAT ACC AGC AAG ATC ACT GGG TTC CTG AAG CCA GGA AAG GTA AAA
367>Thr Phe Asn Thr Ser Lys Ile Thr Gly Phe Leu Lys Pro Gly Lys Val Lys

1225 GTG GAA CTG AAA GAA TCC AAA GTT GGA CTA TTC AAT GCA GAG CTG TTG GAA
384>Val Glu Leu Lys Glu Ser Lys Val Gly Leu Phe Asn Ala Glu Leu Leu Glu

1276 GCG CTC CTC AAC TAT TAC ATC CTT AAC ACC TTC TAC CCC AAG TTC AAT GAT
401>Ala Leu Leu Asn Tyr Tyr Ile Leu Asn Thr Phe Tyr Pro Lys Phe Asn Asp

1327 AAG TTG GCC GAA GGC CTT CCC CTT CCT CTG CTG AAG CGT GTT CAG CTC TAC
418>Lys Leu Ala Glu Gly Phe Pro Leu Pro Leu Leu Lys Arg Val Gln Leu Tyr

1378 GAC CTT GGG CTG CAG ATC CAT AAG GAC TTC CTG TTC TTG GGT GCC AAT GTC
435>Asp Leu Gly Leu Gln Ile His Lys Asp Phe Leu Phe Leu Gly Ala Asn Val

1429 CAA TAC ATG AGA GTT
452>Gln Tyr Met Arg Val
```

FIGURE 2C

Pharmacokinetics of 1 mg/kg $^{125}$I-rBPI$_{23}$ or $^{125}$I-rLBP$_{25}$

```
BPI ... VNPGVVVRISQKGLDYASQQGTAALQKELKRIKIPDYSDSFKIKHLGKGHVSFYSMDIRE
         ::: : ::: :: :: :   :::  :: ::   ::  :: :    :  :  :: ::
LBP ... ANPGLVARITDKGLQYAAQEGLLALQSELLRITLPDFTGDLRIPHVGRGRYEFHSLNIHS
        10        20        30        40        50        60

BPI ... FQLPSSQISMVPNVGLKFSISNANIKISGKWKAQKRFLKMSGNFDLSIEGMSISADLKLG
         : :: :::   ::: ::: :  :: :: :  ::: ::::    ::: ::: :::
LBP ... CELLHSALRPVPGQGLSLSISDSSIRVQGRWKVRKSFFKLQGSFDVSVKGISISVNLLLG
       70        80        90       100       110       120

BPI ... SNPTSGKPTITCSSCSSHINSVHVHISKSKVGWLIQLFHKKIESALRNKMNSQVCEKVTN
        :: :: :::::::::::: :   : :::  ::: :::   :::
LBP ... SE-SSGRPTVTASSCSSDIADVEVDMSG-DLGWLLNLFHNQIESKFQKVLESRICEMIQK
       130       140       150       160       170       180

BPI ... SVSSELQPYFQTLPVMTKI
        :::: ::::: :::::::
LBP ... SVSSDLQPYLQTLPVTTEI
       190       197

LIPOPOLYSACCHARIDE BINDING PROTEIN DERIVATIVES

This is a continuation-in-part of U.S. patent application Ser. No. 08/079,510, abandoned, filed Jun. 17, 1993.

BACKGROUND OF THE INVENTION

The present invention relates generally to proteins useful for the treatment of gram-negative bacterial infections and specifically to the neutralization of the effects of lipopolysaccharide (LPS) which is also known as endotoxin. LPS is a major component of the outer membrane of gram-negative bacteria and consists of serotype-specific O-side chain polysaccharides linked to a conserved region of core oligosaccharide and lipid A. LPS is an important mediator in the pathogenesis of septic shock and is one of the major causes of death in intensive-care units in the United States. It has been observed that exposure to LPS during sepsis stimulates an immune response in monocytes and macrophages that results in a toxic cascade resulting in the production of tumor necrosis factor (TNF) and other proinflammatory cytokines. Morrison and Ulevitch, *Am. J. Pathol.*, 93:527 (1978). Endothelial damage in sepsis probably results from persistent and repetitive inflammatory insults. Bone, *Annals Int. Med.* 115:457 (1991).

LPS-binding proteins have been identified in various mammalian tissues. Among the most extensively studied of the LPS-binding proteins is bactericidal/permeability-increasing protein (BPI), a basic protein found in the azurophilic granules of polymorphonuclear leukocytes. Human BPI protein has been isolated from polymorphonuclear neutrophils (PMNs) by acid extraction combined with either ion exchange chromatography or *E. coli* affinity chromatography. Weiss et al., *J. Biol. Chem.*, 253:2664 (1978); Mannion et al., *J. Immunol.* 142:2807 (1989).

The holo-BPI protein isolated from human PMNs has potent bactericidal activity against a broad spectrum of gram-negative bacteria. This antibacterial activity appears to be associated with the amino terminal region (i.e. amino acid residues 1–199) of the isolated human holo-BPI protein. In contrast, the C-terminal region (i.e. amino acid residues 200–456) of the isolated holo-BPI protein displays only slightly detectable anti-bacterial activity. Ooi et al., *J. Exp. Med.*, 174:649 (1991). Human DNA encoding BPI has been cloned and the amino acid sequence of the encoded protein has been elucidated. Gray et al., *J. Biol. Chem.*, 264:9505 (1989). Amino-terminal fragments of BPI include a natural 25 Kd fragment and a recombinant 23 Kd, 199 amino acid residue amino-terminal fragment of the human BPI holo-protein referred to as rBPI$_{23}$. See, Gazzano-Santoro et al., *Infect. Immun.* 60:4754–4761 (1992). In that publication, an expression vector was used as a source of DNA encoding a recombinant expression product (rBPI$_{23}$) having the 31-residue signal sequence and the first 199 amino acids of the N-terminus of the mature human BPI, as set out in SEQ ID NOS: 11 and 12 taken from Gray et al., supra, except that valine at position 151 is specified by GTG rather than GTC and residue 185 is glutamic acid (specified by GAG) rather than lysine (specified by AAG). Recombinant holoprotein referred to herein as rBPI has also been produced having the sequence set out in SEQ ID NOS:11 and 12 taken from Gray et al., supra, with the exceptions noted for rBPI$_{23}$. See also, Elsbach et al., U.S. Pat. No. 5,198,541 the disclosure of which is hereby incorporated by reference. In addition to its bactericidal effects, BPI has been shown to neutralize the toxic and cytokine-inducing effects of LPS to which it binds.

Lipopolysaccharide binding protein (LBP) is a 60 kD glycoprotein synthesized in the liver which shows significant structural homology with BPI. Schumann et al. disclose the amino acid sequences and encoding cDNA of both human and rabbit LBP. Like BPI, LBP has a binding site for lipid A and binds to the LPS from rough (R-) and smooth (S-) form bacteria. Unlike BPI, LBP does not possess significant bactericidal activity, and it enhances (rather than inhibits) LPS-induced TNF production. Schumann et al., *Science*, 249:1429 (1990). Thus, in contrast to BPI, LBP has been recognized as an immunostimulatory molecule. See, e.g., Seilhamer, PCT International Application WO 93/06228 which discloses a variant form of LBP which it terms LBP-β.

One of the normal host effector mechanisms for clearance of bacteria involves the binding to and subsequent phagocytosis by neutrophils and monocytes. As part of this process, bacteria are exposed to bactericidal and bacteriostatic factors, including oxygen radicals, lysosomal enzymes, lactoferrin and various cationic proteins. LBP opsonizes LPS-bearing particles and intact Gram-negative bacteria, mediating attachment of these LBP-coated particles to macrophages. Wright et al., *J. Exp. Med.* 170:1231 (1989). The attachment appears to be through the CD14 receptor of monocytes which binds complexes of LPS and LBP. Wright et al., *Science* 249.1431 (1990). Anti-CD14 mAbs have been shown to block the synthesis of TNF by whole blood incubated with LPS. Wright et al. *Science* 249.1431 (1990). Interaction of CD14, which is present on the surface of polymorphonuclear leukocytes as well as monocytes, with LPS in the presence of LBP has been shown to increase the adhesive activity of neutrophils. Wright et al., *J. Exp. Med.* 173:1281 (1991), Worthen et al., *J. Clin. Invest.* 90:2526 (1992). Thus, while BPI has been shown to be cytotoxic to bacteria and to inhibit proflammatory cytokine production stimulated by bacteria, LBP promotes bacterial binding to and activation of monocytes through a CD14-dependent mechanism.

LPS, either directly or by inducing proinflammatory cytokines such as IL-1 and TNF, induces the expresion of adhesion molecules including CD54 (intercellular adhesion molecule-1, ICAM-1) and E-selectin (endothelial-leukocyte adhesion molecule-1, ELAM-1) on endothelial cells, and thereby increases binding of leukocytes in vitro. Schleimer and Rutledge, *J. Immunol.* 136:649 (1986); Pohlman et al., *J. Immunol.* 136:4548 (1986); Bevilacqua et al., *J. Clin. Invest.* 76:2003 (1985); Gamble et al., *Proc. Natl. Acad. Sci. USA.* 82:8667 (1985); Smith et al., *J. Clin. Invest.* 82:1746 (1988); and Bevilacqua et al., *Proc. Natl. Sci. USA* 84:9238 (1987). However, as CD14 has not been detected on the surface of endothelial cells (Beekhuizen et al., *J. Immunol.* 147:3761 (1990)) and no other receptor for LPS on endothelial cells has been identified, a different mechanism may exist whereby LPS can affect the endothelium.

Soluble CD14, found in serum (Bazil et al., *Eur. J. Immunol.* 16:1583 (1986)), has been hypothesized to be responsible for transmitting the LPS signal to endothelial cells. Specifically, soluble CD14 has been shown to mediate a number of LPS-dependent effects on endothelial cells, including E-selectin and VCAM expression, IL-1, IL-6 and IL-8 secretion, and cell death. Frey et al., *J. Exp. Med.* 176:1665 (1992); Pugin et al., *Proc. Natl. Acad. Sci. USA.* 90:2744 (1993).

Recent studies have shown that soluble CD14 is involved in the LPS-mediated adhesion of neutrophils to endothelial cells. Anti-CD14 mAbs were able to completely inhibit the adhesion induced by LPS, indicating that the contribution of other CD14-independent LPS receptors to these effects is minimal. The protein(s) on the endothelial cells that soluble CD14 might associate with to transduce the LPS signal remains to be identified. LBP has been shown to be involved in the signal transduction of LPS through soluble CD14; however, at high concentrations of LPS or soluble CD14, LBP does not further enhance the response of endothelial cells to LPS (Pugin et al., *Proc. Natl. Acad. Sci. USA.* 90:2744 (1993).

Larrick et al., *Biochem. and Biophysical Res. Commun.,* 179:170 (1991) relates to a cationic protein obtained from rabbit granulocytes which is identified as CAP18. CAP118 is identified as bearing no sequence homology with either BPI or LBP. In the course of their disclosure, Larrick et al. characterize other publications which discuss the structure of proteins including LBP and incorrectly attribute to the Wright et al., supra disclosure the speculation that "LBP is believed to be composed of two regions: an amino-terminal domain that binds to LPS and a carboxy-terminal domain that may (emphasis supplied) mediate binding of the LBP-LPS complex to the CD14 receptor on leukocytes."

Ulevitch, PCT International Application WO 91/01639 discloses methods and compositions for treatment of sepsis comprising administering anti-CD14 antibodies. The published application also describes "LBP peptide analogs" at page 17 which are stated to be polypeptides capable of competitively inhibiting the binding of LPS-LBP complexes to CD14 expressed on the surface of monocyte derived macrophages. The sequences of the three disclosed "LBP peptide analogs" show 90 to 100% homology with CD14 polypeptide sequences and no homology with LBP sequences.

Ulevitch et al., U.S. Pat. No. 5,245,013 discloses. a lipopolysaccharide binding protein which binds to Gram-negative bacterially secreted LPS and retards in vitro binding of LPS to high density lipoprotein.

Marra, PCT International Application WO 92/03535 discloses various chimeric BPI molecules including an rLBP/BPI chimeric molecule designated LBP25K/BPI30K [LBP (1–197)/BPI(200–456)]and comprising the first 197 amino acid residues of LBP and amino acid residues 200–456 of BPI wherein the coding sequence for the amino-terminal 25 kD portion of LBP was linked to the coding sequence for the carboxy-terminal portion of the BPI protein by virtue of an engineered ClaI site within the coding sequence. The resulting molecule reacted positively in an ELISA assay utilizing anti-BPI protein antibodies and also reacted positively in an endotoxin binding assay. Rogy et al., *J. Clin. Immunol.,* 14:120–133 (1994) describes experiments utilizing the LBP (1–197)/BPI(200–456) molecule wherein animals treated with the molecule in a primate bacteremia model demonstrated decreased LPS levels compared to controls, but still developed the sequalae of septic shock. For example, no significant reduction in endotoxin mediated cytokine synthesis was observed in endotoxin-treated baboons to whom the compound was administered.

There exists a need in the art for LPS binding and neutralizing proteins which lack CD14-mediated immunostimulatory properties, including the ability to mediate LPS activity through the CD14 receptor.

SUMMARY OF THE INVENTION

The present invention provides novel biologically active polypeptide derivatives of Lipopolysaccharide Binding Protein (LBP), including LBP derivative hybrid proteins, which are characterized by the ability to bind to LPS and which lack CD14-mediated immunostimulatory properties, including the ability of LBP holoprotein to mediate LPS activity via the CD14 receptor. More particularly, LBP protein derivatives including LBP derivative hybrid proteins according to the invention lack those carboxy terminal-associated elements characteristic of the LBP holoprotein which enable LBP to bind to and interact with the CD14 receptor on monocytes and macrophages so as to provide an immunostimulatory signal to monocytes and macrophages.

Presently preferred LBP protein derivatives are characterized by a molecular weight less than or equal to about 25 kD. Particularly preferred LBP protein derivatives of the invention are LBP fragments comprising an amino-terminal region of LBP (e.g., amino acid residues 1–197). A molecule comprising the first 197 amino terminal residues of LBP and designated rLBP$_{25}$ exemplifies the derivatives of the invention. This particular derivative includes amino acid regions comprising LBP residues 17 through 45, 65 through 99 and 141 through 167 which correspond to respective LPS binding domains (e.g., residues 17 through 45, 65 through 99 and 142 through 169) of Bactericidal/Permeability-Increasing protein (BPI).

LBP derivative hybrid proteins of the invention comprise hybrids of LBP protein sequences with the amino acid sequences of other polypeptides and are also characterized by the ability to bind to LPS and the absence of CD14-mediated immunostimulatory properties. Such hybrid proteins can comprise fusions of LBP amino-terminal fragments with polypeptide sequences of other proteins such as BPI, immunoglobulins and the like. Preferred LBP/BPI hybrids of the invention comprise at least a portion (i.e., at least five consecutive amino acids and preferably ten or more amino acids) of an LPS binding domain of BPI. One preferred LBP derivative hybrid protein of the LBP/BPI type comprises an amino-terminal LBP amino acid sequence selected from within the amino terminal half of LBP (e.g. within amino acid residues 1–197 of LBP) in which one or more portions of that sequence is replaced by the corresponding sequence of BPI selected from within the amino terminal half of BPI (e.g., within amino acid residues 1–199 of BPI). Another preferred LBP derivative hybrid protein comprises a fusion of amino terminal portions of LBP and heavy chain regions of IgG. Other LBP derivative hybrid proteins comprise LBP amino acid sequences into which all or portions of LPS binding domains of e.g., BPI or other LPS binding protein have been inserted or substituted for all or part of an LPS binding region of LBP. Preferred LBP derivative hybrid proteins include those in which all or portions of the previously-noted amino terminal LPS binding domains of BPI replace the corresponding region within LBP.

LBP protein derivatives and LBP derivative hybrid proteins of the invention are expected to display one or more advantageous properties in terms of pharmacokinetics, LPS binding, LPS neutralization and the like.

The present invention further provides novel pharmaceutical compositions comprising the LBP protein derivatives and LBP derivative hybrid proteins along with pharmaceutically acceptable diluents, adjuvants, and carriers and correpsondingly addresses the use of LBP protein derivatives and LBP derivative hybrid proteins in the manufacture of medicaments for treating gram negative bacterial infections and the sequelae thereof.

Polypeptides of the invention may be synthesized by assembly of amino acids. In addition, the invention provides DNA sequences, plasmid vectors, and transformed cells for producing the LBP protein derivatives and LBP hybrid derivative proteins of the invention.

Numerous additional aspects and advantages of the invention will become apparent to those skilled in the art upon consideration of the following detailed description of the invention which describes presently preferred embodiments thereof.

BRIEF DESCRIPTION OF THE DRAWINGS

FIG. 1 depicts the DNA sequence and translated amino acid sequence (1–197) of rLBP$_{25}$ [SEQ ID NOS:1 and 2];

FIG. 2 depicts the DNA sequences and translated amino acid sequence (1–456) of rLBP [SEQ ID NOS:3 and 4];

FIG. 23 depicts a homology comparison of the amino-terminal amino acid residues of human LBP and human BPI.

DETAILED DESCRIPTION

Figure 3:
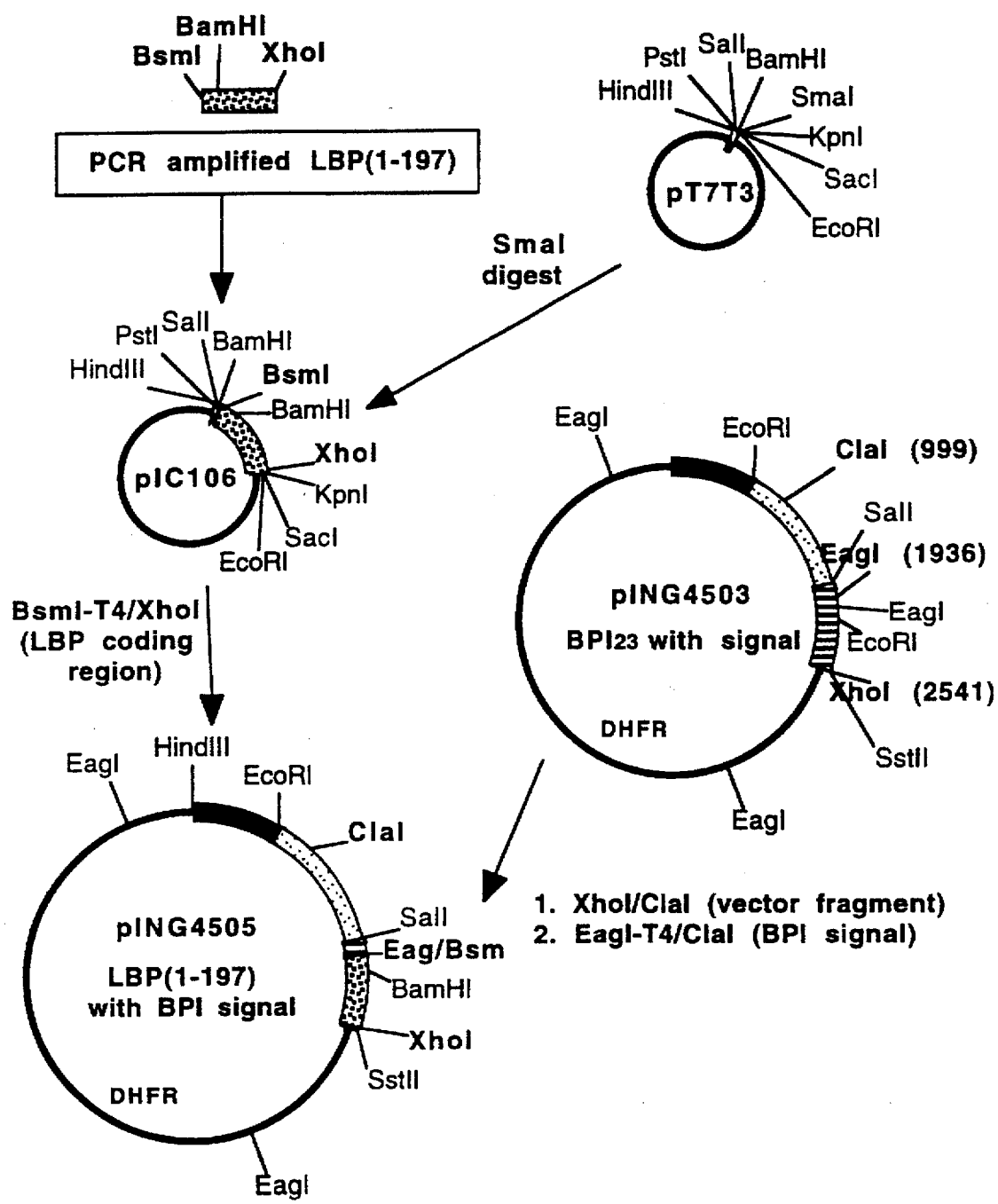
FIG. 3 depicts the construction of an rLBP$_{25}$ mammalian expression vector pING4505.

The present invention encompasses LBP protein derivatives and LBP derivative hybrid proteins which are characterized by the ability to bind to LPS but which lack the carboxy terminal-associated immunostimulatory element(s) characteristic of the LBP holoprotein and thus lack the CD14-mediated immunostimulatory activity characteristic of LBP holoprotein. Preferred LBP protein derivatives are characterized as including N-terminal LBP fragments having a molecular weight of about 25 kD. Most preferred are LBP N-terminal fragments characterized by the amino acid sequence of the first 197 amino acids of the amino-terminus of LBP set out in FIG. 1 and SEQ ID NOS:1 and 2. It is also contemplated that LBP protein derivatives containing N-terminal fragments considerably smaller than 25 kD and comprising substantially fewer than the first 197 amino acids of the N-terminus of the LBP holoprotein molecule are suitable for use according to the invention provided they retain the ability to bind to LPS. Thus, specifically contemplated are LBP derivatives comprising part or all of one or more of three regions (defined by LBP amino acid sequences 17–45, 65–99 and 141–167) corresponding (by reason of amino acid homology) to LPS binding regions (comprising amino acid sequences 17–45, 65–99 and 142–169) of BPI. Moreover, it is contemplated that LBP protein derivatives comprising greater than the first 197 amino acid residues of the holo-LBP molecule, i.e., including amino acids on the carboxy-terminal side of residue 197 of rLBP as disclosed in FIG. 2 and SEQ ID NOS:3 and 4 will likewise prove useful according to the methods of the invention provided they lack CD14-mediated immunostimulatory activity. It is further contemplated that those of skill in the an are capable of making additions, deletions and substitutions of the amino-acid residues of SEQ ID NOS:1–4 without loss of the desired biological activities of the molecules. Such, LBP protein derivatives may be obtained by deletion, substitution, addition or mutation, including mutation by site-directed mutagenesis of the DNA sequence encoding the LBP holoprotein, wherein the LBP protein derivative maintains LPS-binding activity and lacks CD14-mediated immunostimulatory activity. One preferred LBP derivative is that wherein the alanine residue at position 131 of the illustrative LBP (1–197) polypeptide fragment is substituted with a cysteine residue. The resulting LBP (1–197) (Cys 131) polypeptide may have the ability to dimerize via interchain disulfide bond formation through cysteine 131 and the resulting dimer may be characterized by improved biological activity.

Also contemplated are LBP derivative hybrid proteins including LBP/BPI hybrid proteins [but excluding the hybrid designated LBP(1–197)/BPI(200–456) noted above] and LBP-Ig fusion proteins which are characterized by the ability to bind LPS but which lack CD-14 immunostimulatory activity. A preferred LBP/BPI hybrid protein of the invention is a protein comprising one or more portion of the amino-terminal half of LBP, e.g., selected from within amino acid residues 1–197 of LBP, and a one or more portions of the amino-terminal half of BPI, e.g., selected from within amino acid residues 1–199 of BPI.

Other LBP hybrid proteins comprise LBP amino acid sequences into which all or portions of LPS binding domains of other LPS binding proteins (such as BPI) have been inserted or substituted. Preferred LBP hybrid proteins include those in which all or portions of the LPS binding domains of BPI (comprising BPI residues 17–45, 65–99 and 142–169) are substituted into the corresponding region of LBP. Portions of such BPI domains substituted into the hybrid proteins may comprise as few as five continuous amino acids but preferably include ten or more continuous amino acids.

LBP derivative hybrid proteins in which all or portions of the LPS binding regions of BPI are substituted into the corresponding region of LBP thus include those comprising at least a part of an LPS binding domain of BPI selected from the group of amino acid sequences consisting of:

ASQQGTAALQKELKRIKPDYSDSFKIKH (SEQ ID NO:17) designated Domain I comprising the amino acid sequence of human BPI from about position 17 to about position 45;

SSQISMVPNVGLKFSISNANIKISGKWKAQKRFLK (SEQ ID NO:18) designated Domain II comprising the amino acid sequence of human BPI from about position 65 to about 99; and VHVHISKSKVGWLIQLFHKKIESALRNK (SEQ ID NO:19) designated Domain III comprising the amino acid sequence of human BPI from about position 142 to about position 169.

These LPS binding domains of BPI correspond to LBP regions consisting of:

AAQEGLLALQSELLRITLPDFTGDLRIPH (SEQ IS NO:20) comprising the amino acid sequence of human LBP from about position 17 to about position 45;

HSALRPVPGQGLSLSISDSSIRVQGRWKVRKSFFK (SEQ ID NO:21) comprising the amino acid sequence of human LBP from about position 65 to about 99; and VEVDMSGDLGWLLNLFHNQIESKFQKV (SEQ ID NO 22) comprising the amino acid sequence of human LBP from about position 141 to about position 167.

According to another aspect of the invention, DNA sequences are provided which encode the above-described LBP protein derivatives and LBP derivative hybrid proteins. Also provided are autonomously replicating DNA plasmid vectors including such DNA sequences and host cells stably transformed or transfected with such DNA sequences in a manner allowing their expression. Transformed host cells of the invention are of manifest utility in procedures for the large-scale production of the LBP protein derivatives and LBP derivative hybrid proteins of the invention involving the cultured growth of the hosts in a suitable medium and the isolation of the proteins from the cells or their growth medium.

The invention further provides novel pharmaceutical compositions comprising an LBP protein derivative or an LBP derivative hybrid protein which retains LPS-binding activity and lacks CD14-mediated immunostimulatory activity together with pharmaceutically acceptable diluents, adjuvants, and carriers. The compositions are useful in methods for treating a gram-negative bacterial infection, including the sequelae thereof such as endotoxin related shock, and one or more of conditions associated with gram-negative bacterial infection and resulting endotoxic shock such as disseminated intravascular coagulation, anemia, thrombocytopenia, leukopenia, adult respiratory distress syndrome, renal failure, hypotension, fever and metabolic acidosis. Such methods comprise administering an LBP protein derivative or LBP derivative hybrid protein to a subject suffering from a gram-negative bacterial infection, including the sequelae thereof.

When employed for treatment of a gram-negative bacterial infection, including the sequelae thereof, LBP protein derivatives and LBP derivative hybrid proteins of the invention are preferably administered parenterally and most preferably intravenously in amounts broadly ranging from about 0.1 milligram and about 100 milligrams per kilogram of body weight of the treated subject with preferred treatments ranging from about 1 milligrams and 25 milligrams per kilogram of body weight. It is contemplated that administration of LBP derivative protein derivatives, such as $rLBP_{25}$, and LBP hybrid proteins may be useful as one aspect of a combination therapy in which BPI or other antibiotics are administered to a subject.

According to a further aspect of the invention, LBP protein derivatives and LBP derivative hybrid proteins may be administered in combination with other therapeutic compositions which are not strictly antibiotics but rather which neutralize the endotoxic effects of LPS such as anti-LPS antibodies and antibodies to constituents of the LPS mediated toxic cascade such as anti-TNF antibodies.

The following detailed description relates to the manufacture and properties of LBP protein derivatives and LBP hybrid proteins of the invention. More specifically, Example 1 relates to the construction of vectors for expression of an exemplary LBP protein derivative, $rLBP_{25}$. Example 2 relates to the construction of vectors for expression of rLBP. Examples 3 and 4 relate to the incorporation of the vectors of Examples 1 and 2 into appropriate host cells and further describes the expression and purification of $rLBP_{25}$ and rLBP. Examples 5 and 6 relate to construction of vectors encoding LBP/BPI hybrid promins. Example 7 relates to in vitro transcription translation of the LBP/BPI hybrid protein, LBP(1–43)/BPI(44–199)and BPI(1–159)/LBP(158–197). Example 8 relates to the pharmacokinetics of $rLBP_{25}$, rLBP and $rBPI_{23}$ in vivo. Example 9 relates to the binding of $rLBP_{25}$ and rLBP to Lipid A. Example 10 relates to competition by $rLBP_{25}$ and $rBPI_{23}$ for the binding of $^{125}I$-$rLBP_{25}$ to immobilized lipid A. Example 11 relates to competition by rLBP and $rBPI_{23}$ for the binding of $^{125}I$-rLBP to immobilized lipid A. Example 12 relates to the effect of $rLBP_{25}$ and rLBP on an LAL assay. Example 13 relates to the effect of $rLBP_{25}$ and rLBP on the binding/uptake $^{125}I$-labeled LPS on TNF production by a human monocyte cell line THP-1. Example 14 relates to the effect of $rLBP_{25}$ and rLBP on TF and TNF production by isolated PBMCs. Example 15 relates to the effect of $rLBP_{25}$ on LPS-induced adhesiveness of endothelial cells for neutrophils. Example 16 relates to the effect of rLBP and $rLBP_{25}$ on bacterial binding to monocytes and polymorphonuclear cells. Example 17 relates to a sandwich ELISA assay for rLBP and $rLBP_{25}$. Example 18 relates to construction of vectors for production of LBP (1–197) (Cys 131). Example 19 relates to construction of vectors for production of LBP-IgG hybrid fusion proteins. Example 20 relates to in vitro transcription/translations of truncated LBP fragments and determination of their ability to mediate LPS stimulation of TNF activity. Example 21 relates to construction of vectors for production of LBP/BPI hybrid proteins. Example 22 relates to construction of vectors for production of LBP/BPH hybrid proteins comprising BPI/LBP active domain replacement anti partial replacement routants. Example 23 relates to properties of synthetic LBP peptides.

EXAMPLE 1

Construction of Vectors for Expression of $rLBP_{25}$ Protein

A. Cloning and sequencing of human $rLBP_{25}$

The DNA encoding amino acids 1–197 of human LBP without the signal sequence (designated "$rLBP_{25}$") was obtained by PCR using human liver poly $(A)^+$ RNA (Clontech Laboratories, Palo Alto, Calif.) as the source of material for amplification. Reverse transcription of the RNA to cDNA and PCR amplification were carded out using the GeneAmp RNA PCR Kit (Perkin Elmer Cetus, Norwalk, Conn.) according to the manufacturer's protocols. The sequence of human LBP was obtained from GenBank, accession number M35533, as published by Schumann et al., *Science*, 249:1429-1431 (1990). The 5' PCR primer corresponded to the amino terminal sequence of the coding region of mature LBP and included a BsmI recognition site at its 5' end. The sequence of this primer, LBP-Bsm, was: 5'-GAATGCAGCCAACCCCGGCTTGGTCGCCA-3' (SEQ ID NO:5). The 3' PCR primer was designed to place a stop codon and an XhoI site following the isoleucine at amino acid position No. 197. The sequence of this primer, LBP-2, was: 5'-CTCGAGCTAAATCTCTGTTGTAACTGGC-3' (SEQ ID NO:6). This amino acid was chosen as the endpoint of rLBP$_{25}$ based on sequence homology with an amino-terminal active fragment of BPI (designated rBPI$_{23}$).

The amplified rLBP$_{25}$ DNA was blunt-end cloned into SmaI cut pT7T318U (Pharmacia, LKB Biotechnology, Piscataway, N.J.) to generate plasmid pIC106. The LBP insert in pIC106 was sequenced using Sequenase (USB). The rLBP$_{25}$ DNA sequence obtained and the derived amino acid sequence is set out in SEQ ID NOS:1 and 2. The sequence differs in two areas from the sequence of the corresponding region of LBP as published by Schumann et al. (1990) *Science*, 249:1429-1431, which involve changes in amino acids. These sequence differences are detailed in Table 1.

B. Construction of Vectors for Expression of rLBP$_{25}$ in Mammalian Cells

A vector for the expression of rLBP$_{25}$ using the BPI signal sequence was constructed using the rLBP$_{25}$ coding region sequence isolated from PIC106 by digestion with BsmI, blunt ending with T4 polymerase, and digestion with XhoI. This was ligated to two fragments isolated from pING4503 (a plasmid described in co-owned and copending U.S. Ser. No. 07/885,911 filed May 19, 1992 by Theofan et al. which is hereby incorporated by reference). Briefly, the construction of pING4503 is based on plasmid pING2237N which contains the mouse immunoglobulin heavy chain enhancer element, the LTR enhancer-promoter element from Abelson murine leukemia virus (A-MuLV) DNA, the SV40 19S/16S splice junction at the 5' end of the gene to be expressed, and the human genomic gamma-1 polyadenylation site at the 3' end of the gene to be expressed. Plasmid pING2237N also has a mouse dihydrofolate reductase (DHFR) selectable marker. The two fragments from pING4503 were the vector fragment generated by digestion with ClaI and XhoI, and a fragment containing the BPI signal sequence generated by digestion with EagI, blunt ending with T4 polymerase, and digestion with ClaI. This ligation resulted in a fusion of the BPI signal to the rLBP$_{25}$ coding region, keeping the correct reading frame, and generating pING4505 (DHFR gene). The corresponding gpt vector, designated pING4508, was generated by subcloning the SalI to SstII insert from pING4505 into the SalI and SstII vector fragment from pING3920 (the structure of which is described in co-owned and copending U.S. Ser. No. 07/718,274 filed Jun. 20, 1991 by Grinna et al., which is hereby incorporated by reference). The construction of pING4505 is outlined in FIG. 3.

EXAMPLE 2

Construction of Vectors for Expression of rLBP Proteins

A. Cloning and Sequencing of Human rLBP

The DNA encoding full length human rLBP (amino acids 1-452, designated "rLBP," plus the 25 amino acid signal sequence) was obtained by PCR using human liver poly (A)$^+$ RNA (Clontech Laboratories, Palo Alto, Calif.) as described for rLBP$_{25}$ above. The 5' PCR primer introduced a SalI recognition site at the 5' end of the LBP signal. The sequence of this primer, LBP-3, was: 5'-CATGTCGACACCATGGGGGCCTTG G-3' (SEQ ID NO:7). The 3' PCR primer was designed to introduce an SstII site following the stop codon of LBP. The sequence of this primer, LBP-4, was: 5'-CATGCCGCGGTCAAACTCTCATGTA-3' (SEQ ID NO:8). The amplified rLBP DNA was blunt-end cloned into SmaI cut pT7T318U to generate plasmid pIC128. The LBP insert in pIC128 was sequenced using Sequenase (USB). The rLBP DNA sequence obtained and the derived amino acid sequence are shown in SEQ ID NOS:3 and 4. Additional differences were found between the LBP sequence in pIC128 and the sequence of LBP as published by Schumann et al., *Science* 249:1429-1431 (1990). The rLBP sequence actually encoded 456 amino acids; there was an insertion of 4 amino acids at position 241. The rLBP sequence in pIC128 additionally contained several nucleotide substitutions that did not change the amino acids compared to Schumann et al. All the differences are highlighted in Table 1. The amino acid sequence is identical to the recently published sequence of LBP$_\beta$ (Seilhamer, PCT International Application WO 93/06228), however, the nucleotide sequence of rLBP herein differs from that of the published LBP$_\beta$ sequence at the sequence encoding amino acids 152 and 179 as shown in Table 1.

TABLE 1

LBP Sequence Differences

| Amino Acid Position [1] | rLBP Sequence | | Schumann LBP Sequence | |
|---|---|---|---|---|
| | Nucleotide | Protein | Nucleotide | Protein |
| -21 | GCC | A | GCA | A |
| 72 | CCT | P | CCC | P |
| 129 | GTT | V | GGT | G |
| 130 | ACT | T | TAC | Y |
| 131 | GCC | A | TGC | C |
| 132 | TCC | S | CTC | L |
| 148 | GAC | D | GAT | D |
| 149 | TTG | L | TCG | S |
| 152[2] | CTG | L | CTC | L |
| 179 | TCG/TCA[3] | S | TCA | S |
| 241-245 | GTC ATG AGC CTT CCT (SEQ ID NO:9) | VMSLP (SEQ ID NO:10) | GCT | A |
| 411 | TTC | F | CTC | L |

[1] Amino Acid positions as numbered in SEQ ID NO:4.
[2] This amino acid position not identified as different for LBP-β.
[3] Both nucleotide sequences were found in different PCR-derived clones.

This amino acid position also not identified as different for LBP-β.

B. Construction of Vectors for Expression of rLBP in Mammalian Cells

To construct a vector for expression of rLBP in mammalian cells, pIC128 was digested with SalI and SstII, the LBP insert was isolated, and then subcloned into SalI and SstII digested vector pING4222 which is described in co-owned and copending U.S. Ser. No. 08/013,801 filed Feb. 2, 1993 which is hereby incorporated by reference. The resulting rLBP vector was designated pING4539 and also contained the DHFR gene for selection.

EXAMPLE 3

Production and Purification of rLBP

Mammalian cells are preferred host cells for production of LBP protein derivatives of the invention because such cells allow secretion and proper folding of heterodimeric and multimeric proteins and provide post-translational modifications such as pro-sequence processing and glycosylation.

Mammalian cells which may be useful as hosts for the production of LBP protein derivatives (including LBP/BPI hybrid proteins and rLBP-Ig fusion proteins) include cells of lymphoid origin, such as the hybridoma Sp2/O-Ag14 (ATCC CRL 1581) and cells of fibroblast origin, such as Veto cells (ATCC CRL 81), CHO-K1, CHO-DXB11, or CHO-DG44. The latter cell line (a DHFR$^-$mutant of CHO Toronto obtained from Dr. Lawrence Chasin, Columbia University) was maintained in Ham's F12 medium plus 10% fetal bovine serum supplemented with glutamine/penicillin/streptomycin (Irvine Scientific, Irvine, Calif.).

CHO-DG44 cells were transfected with linearized pING4539 DNA (40 µg, digested with PvuI, phenol-chloroform extracted and ethanol precipitated) using electroporation. Following recovery, the cells were diluted and $1\times10^4$ cells were plated per 96-well plate well in selective medium consisting of an αMEM medium lacking nucleosides (Irvine Scientific) and supplemented with dialyzed fetal bovine serum (100 ml serum dialyzed using 4L cold 0.15 NaCl using 6000–8000 cutoff for 16 hours at 4° C.). Untransfected CHO-DG44 cells are unable to grow in this medium because they possess the DHFR$^-$ mutation and were removed during successive feedings with the selective medium. At 1.5–2 weeks, microcolonies consisting of transfected cells were observed.

Clones were analyzed for the presence of LBP-reactive protein in culture by ELISA using Immulon-II 96 well plates (Dynatech). Supernatant samples were added to the plates, incubated 46 hours, 4° C. followed by goat anti-LBP antiserum and peroxidose-labeled rabbit anti-goat anti-serum. The 21 most productive positive clones were expanded in selective αMEM medium and then grown on selective medium supplemented with 0.05µM methotrexate. The best producing amplified clone was chosen based on ELISA of supernatants as described above and then expanded in αMEM media containing 0.05µM methotrexate for growth in roller bottles.

rLBP was produced in CHO-DG44 cells transfected with the plasmid pING-4539. All incubations were performed in a humidified 5% $CO_2$ incubator maintained at 37° C. Working stock cultures were grown in DME/F-12 with 10% FCS, and were then seeded into 40 2-liter roller bottles (500 mL per bottle) at a density of $9.6\times10^4$ cells/mL in DME/F-12 with 5% FCS ($4.8\times10^7$ cells/bottle). Four days later, the culture supernatants from each bottle were removed and then replaced with 500 mL of fresh media (DME/F-12 with 2.5% FCS). Ten mL of an S-Sepharose (Pharmacia) ion exchange resin slurry (50% v/v, sterilized by autoclaving) was then added to each bottle, and incubation was continued. After 2 days, the media containing S-Sepharose was harvested and replaced with fresh media again containing S-Sepharose. This process was repeated one more time, to yield three harvests of S-Sepharose over a four day period. After each harvest, the S-Sepharose resin was allowed to settle for 1 hour, and the spent media was removed by aspiration. The sedimented S-Sepharose was resuspended in fresh media and pooled. The method of purification using S-Sepharose has been described and claimed in co-owned and copending U.S. patent application Ser. No. 07/855,501 and in co-owned and copending PCT U.S. Ser. No. 93/04752 filed May 19, 1993, the disclosures of which are hereby incorporated by reference in their entirety.

All chromatographic resins used in the purification of rLBP and rLBP$_{25}$ were depyrogenated by immersion in 0.2N NaOH, 1M NaCl and then rinsed with pyrogen-free water All buffers and reagents were prepared with bottled, pyrogert-free water for irrigation (Baxter).

The S-Sepharose resin harvested from culture supernatants was washed successively with 5 volumes of cold 20 mM MES, 0.1M NaCl, pH 6.8 (two times), 20 mM NaAc, 0.1M NaCl pH 4.0 (two times), and 20 mM NaAc, 0.4M NaCl, pH 4.0 (two times). For each of these sedimentations, the resin (in 1 L roller bottles) was allowed to settle at 1×g in the cold. The resin from each harvest (100–200 mL settled volume) was next packed into individual 5×10 cm columns and equilibrated in 20 mM NaAc, 0.4M NaCl, pH 4.0 at 4° C. Two of the columns were subsequently washed with 20 mM NaAc, 0.7M NaCl, pH 4.0, until the absorbance at 280 nm approached zero, and were then batch eluted with 20 mM NaAc, 1.0M NaCl, pH 4.0. Eluted rLBP was identified by SDS-PAGE in 12.5% gels. These gels also showed that some of the rLBP has eluted in the 0.7M NaCl wash. Consequently, the third batch of resin (about 300 mL) was eluted with a gradient of NaCl (0.4M to 1.0M) in 20 mM NaAc, pH 4.0, and 8.5 mL fractions were collected. SDS-PAGE analysis of column fractions indicated that rLBP eluted between fractions 70 and 100. It was estimated that the amount of total protein present in all three eluates was approximately 800 mg.

The S-Sepharose fractions containing rLBP from the three harvests were pooled (850 mL), and one-half of the material (425 ml, or about 400 mg rLBP) was purified further. To this material was added 1275 mL of 20 mM NaAc, pH 4.0, such that the final concentration of NaCl would be approximately 0.25M, and the solution was applied to a second S-Sepharose column (2.5×30 cm) equilibrated at 4° C. in 20 mM NaAc, 0.4M NaCl, pH 4.0. The column was eluted with a gradient of NaCl (0.4 to 1.0M) in 20 mM NaAc, pH 4.0, and column fractions containing rLBP were again identified by SDS-PAGE and pooled. The final volume of pooled material was 133 ml, and it contained about 260 mg of rLBP.

Final purification of rLBP was accomplished by chromatographing the eluate from the second S-Sepharose column on a 345 mL Sephacryl S-100 size exclusion column equilibrated in 20 mM NaCitrate, 0.15M NaCl, pH 5.0 at 4° C. Five 25 mL aliquots of the S-Sepharose eluate were successively applied to, and eluted from, the column, and 3.7 mL fractions were collected. SDS-PAGE analysis of the effluent fractions indicated that rLBP eluted as a single band, and peak fractions were pooled and stored at 4° C. The peak fractions from all five S-100 runs were then pooled. The final material (about 245 mg) was >99% pure by SDS-PAGE, and exhibited a molecular weight of about 60 kD.

EXAMPLE 4

Production and Purification of rLBP$_{25}$

CHO-DG44 cells were transfected with linearized pING4505 DNA (40 µg, digested with PvuI, phenol-chloroform extracted and ethanol precipitated) using the calcium phosphate method of Wigler, et al., Cell, 11:223 (1977). Following calcium phosphate treatment, the cells were plated in T75 flasks and transfectants were obtained by growth in selective medium consisting of an αMEM medium lacking nucleosides (Irvine Scientific) and supplemented with dialyzed fetal bovine serum (100 ml serum dialyzed using 4L cold 0.15 NaCl using 6000–8000 cutoff for 16 hours at 4° C.). Untransfected CHO-DG44 cells are unable to grow in this medium because they possess the DHFR$^-$ mutation and were removed during successive feedings with the selective medium. At 1.5–2 weeks, only microcolonies consisting of transfected cells were observed. The transfected cells were removed from the flasks by trypsinization and subcloned by limiting dilution in 96 well plates.

Subclones were analyzed for the presence of rLBP$_{25}$ protein in culture supernatants by anti-gamma ELISA using Immulon-II 96 well plates (Dynatech) with LPS as a pre-coat, followed by culture supernatant, goat anti-LBP antiserum and peroxidase-labeled rabbit anti-goat antiserum. The positive clones were also retested for LBP specific mRNA. The top producing clone was expanded in selective αMEM medium for growth in roller bottles.

rLBP$_{25}$ was produced in CHO-DG44 cells transfected with the plasmid pING4505 following procedures similar to those described above in Example 3 for rLBP, with minor modifications. After the harvested S-Sepharose was washed in 20 mM NaAc, 0.4M NaCl, pH 4.0, rLBP$_{25}$ was batch eluted by the addition of 20 mM NaAc, 1.0M NaCl, pH 4.0. To the pooled 1.0M NaCl eluates from the 3 harvests (862 mL) was added 137 mL of 0.5M MES, such that the final volume was 999 mL, and the final NaCl concentration was about 0.87M. At this stage, it was estimated that the amount of total protein present was about 775 mg.

A portion of S-Sepharose eluate (549 mL) was diluted with water such that the final volume was 1600 mL, and the final NaCl concentration was about 0.3M. This diluted material was applied to a 2.5×20 cm column of Q-Sepharose previously equilibrated in 20 mM MES, 0.2M NaCl, pH 5.5 at 4° C. The eluate flowing through the column (which contains the rLBP$_{25}$) was then applied to a second S-Sepharose column (2.5×30 cm), and the column was eluted with a gradient of 0.4M to 1.2M NaCl in 20 mM NaAc, pH 4.0. rLBP$_{25}$-containing fractions were identified by SDS-PAGE and peak fractions were pooled. This pooled material (60 mL) was divided into 20 mL aliquots and sequentially chromatographed on Sephacryl S-100. Peak fractions from the three runs were pooled and rechromatographed over the same S-100 column. The final material (about 33 mg) was>99% pure by SDS-PAGE, and exhibited a molecular weight of about 22 kDa.

EXAMPLE 5

Construction of Vectors for Expression of LBP (1–43)/BPI (44–199) Hybrid Protein In this example vectors encoding a hybrid protein [LBP (1–43)/BPI (44–199) hybrid] comprising the first 43 amino-terminal amino acids of LBP and amino acid residues 44–199 of BPI (for BPI see [SEQ ID NOS:11 AND 12] were constructed.

A. Construction of Intermediate Vector pIC111

Figure 4:
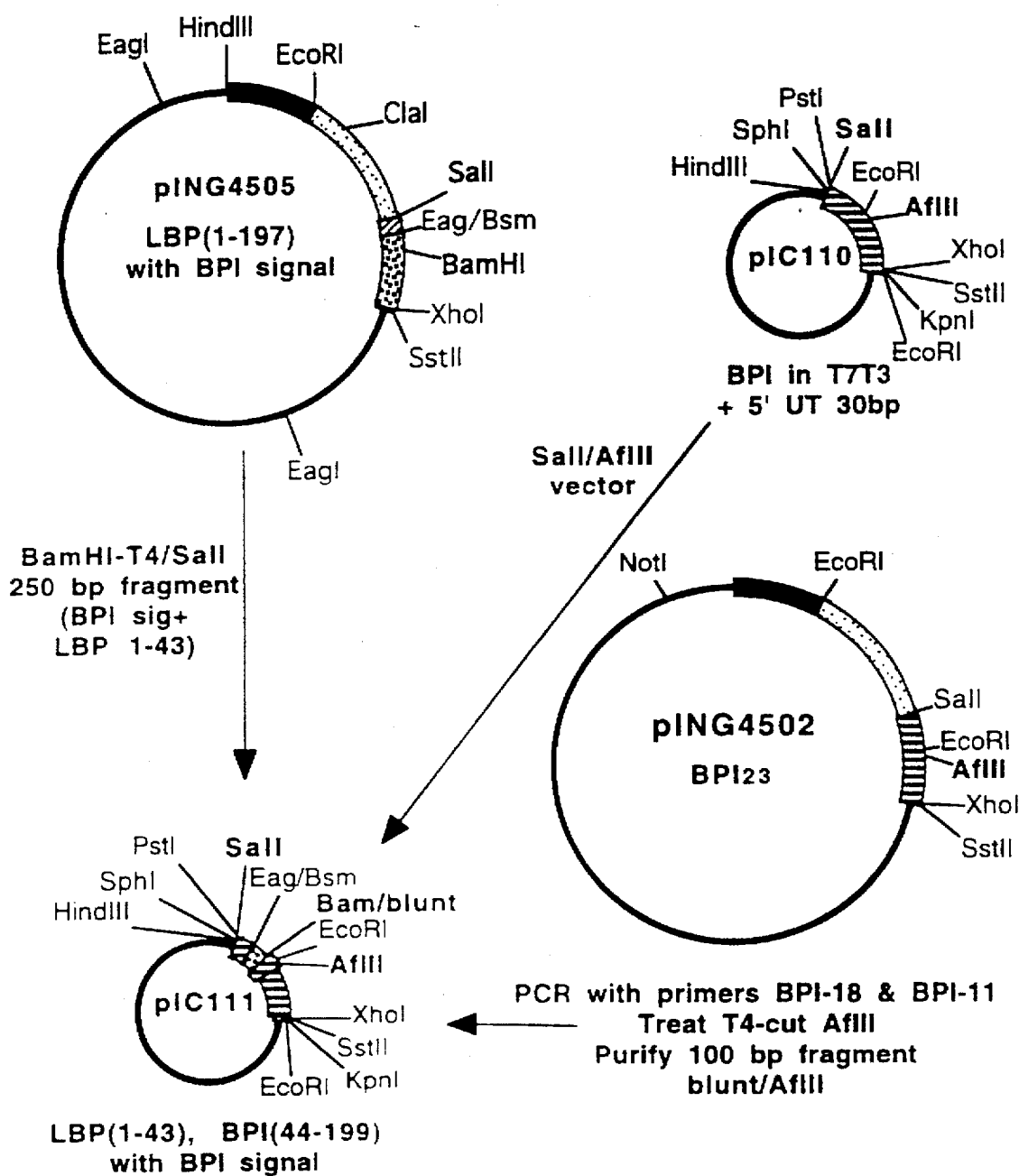
FIG. 4 depicts construction of a vector pIC111 encoding an LBP (1–43)/BPI (44–199) hybrid protein.

Intermediate vector pIC111 was constructed according to the following procedure as set out in FIG. 4. A 250 bp fragment was isolated from pING4505 that encoded the BPI signal sequence and amino acids 1–43 of LBP by digesting with BamHI, blunting the end with T4 polymerase, then cutting with Sal I. To generate a fragment of BPI that would provide a blunt junction beginning with amino acid 44, a PCR fragment was produced using two primers. The sequence of primer BPI-18 was 5' AAGCATCTTGG-GAAGGGG 3' [SEQ ID NO:13] and the sequence of primer BPI-11 was 5' TATTTTGGTCATTACTGGCAGAGT 3' [[SEQ ID NO:14]. The BPI-containing plasmid pING4502 was used as template. Plasmid pING4502 is essentially the same as plasmid pING4503, but does not contain the 30 bp of the 5' UT region of BPI and has the gpt gene instead of DHFR gene for selection. The PCR amplified DNA was digested with AflII and the resulting 100 bp fragment, encoding BPI residues 44 through about 76 was purified. This fragment was ligated together with the 250 bp BPI signal/LBP 1–43 fragment described above into the SalI-AflII vector fragment from pIC110 (BPI in T7T3) to generate pIC111.

B. Construction of Mammalian Expression Vector pING4525

The insert in pIC111 encoding LBP (1–43)/BPI (44–199) with BPI signal was digested with SalI and SstII and subcloned into SalI-SstII digested pING4502 vector to generate mammalian expression vector pING4525. The construction of pING4525 is set out in FIG. 5.

C. Construction of Vector for In Vitro Transcription, Translation (pML105)

Figure 6:
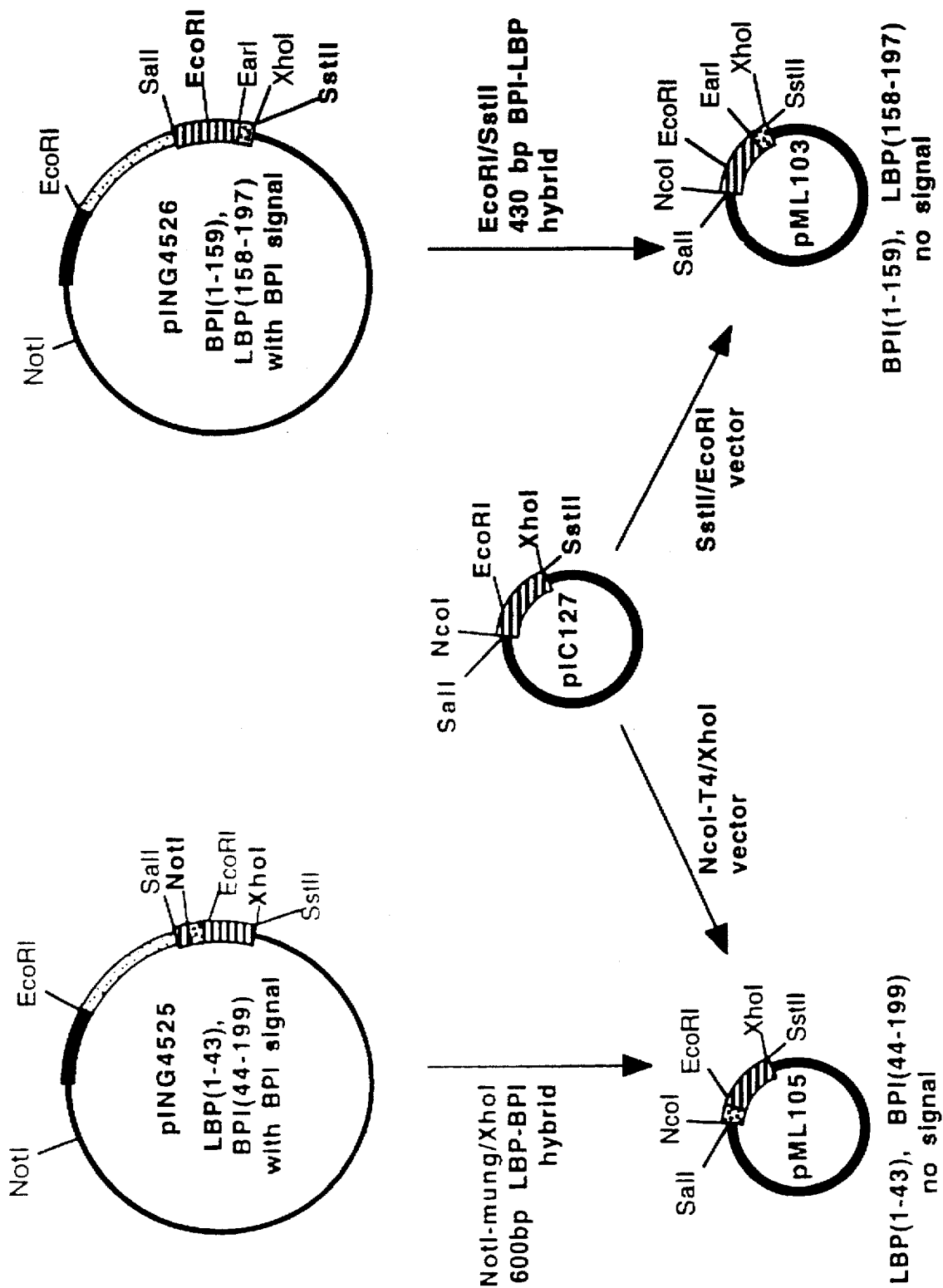
FIG. 6 depicts construction of plasmids pML105 and pML103 for in vitro transcription/translation of LBP/BPI hybrid proteins.

The construction of in vitro transcription plasmid pML105 is set out in FIG. 6. pING4525 was digested with NotI, treated with mung bean nuclease to blunt the end, then digested with XhoI. The resulting 600 bp fragment, which encodes LBP (1–43)/BPI (44–199) without a signal sequence, was gel purified. This fragment was subcloned into pIC127 plasmid which had been digested with NcoI, treated with T4 polymerase then XhoI, to generate pML105. pIC127 is essentially pGEM1 (Promega, WI) with a BPI$_{23}$ insert cloned downstream of the SP6 RNA polymerase promoter designed for in vitro transcription of the BPI. Digestion of pIC127 with NcoI followed by T4 polymerase (to fill in) generates an ATG that can be joined in a blunt junction to a sequence that can then be transcribed in a cell free system.

EXAMPLE 6

Construction of Vectors for Expression of BPI (1–159)/LBP (158–197) Hybrid Protein In this example a vector encoding a hybrid protein [BPI (1–159)/LBP (158–197)] comprising the first 159 amino terminal amino acids of BPI and amino acid residues 158–197 of LBP was constructed.

A. Construction of intermediate pIC112.

Figure 7:
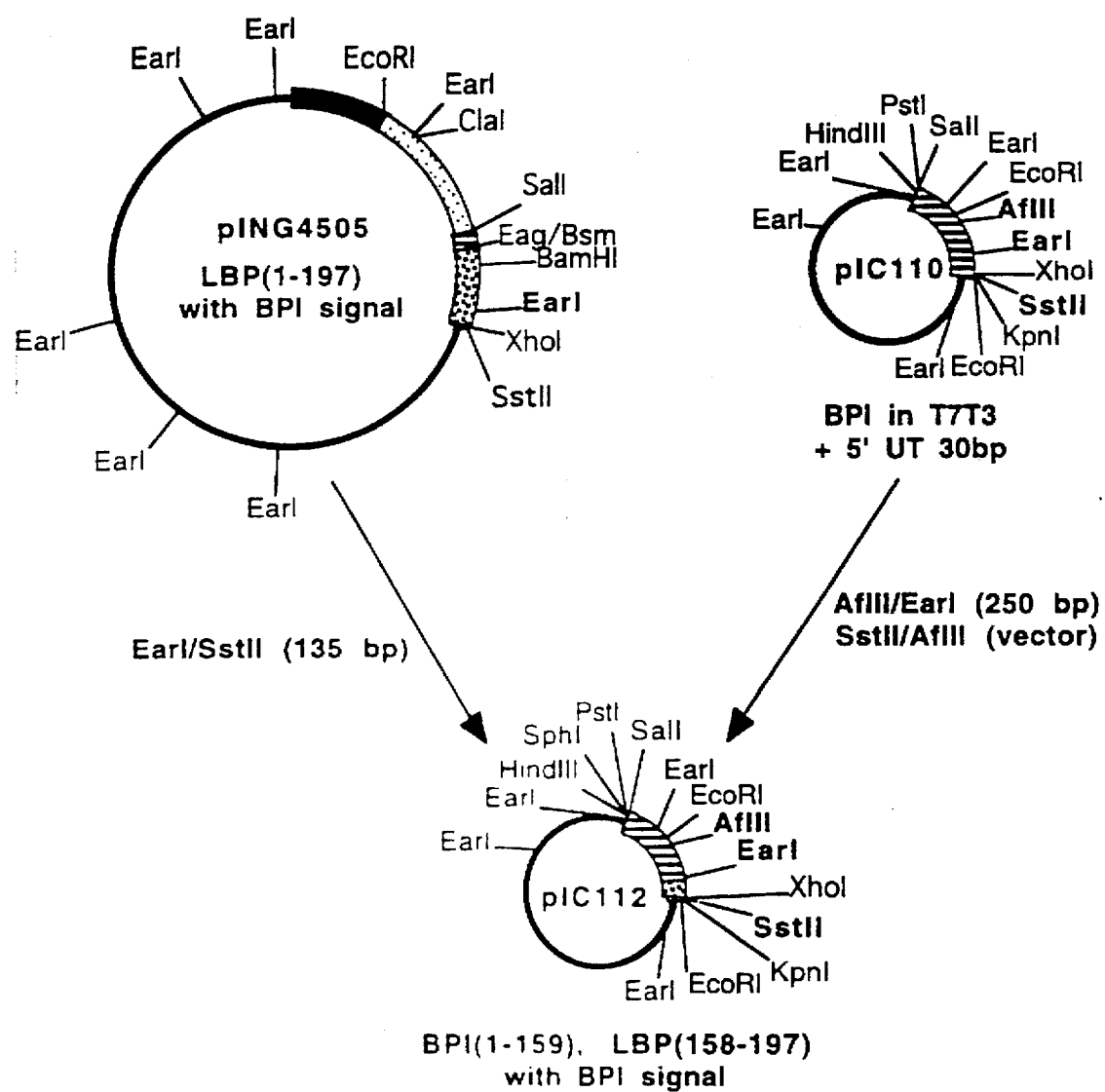
FIG. 7 depicts construction of a vector pIC112 encoding a BPI (1–159)/LBP (158–197) hybrid protein.
Figure 8:
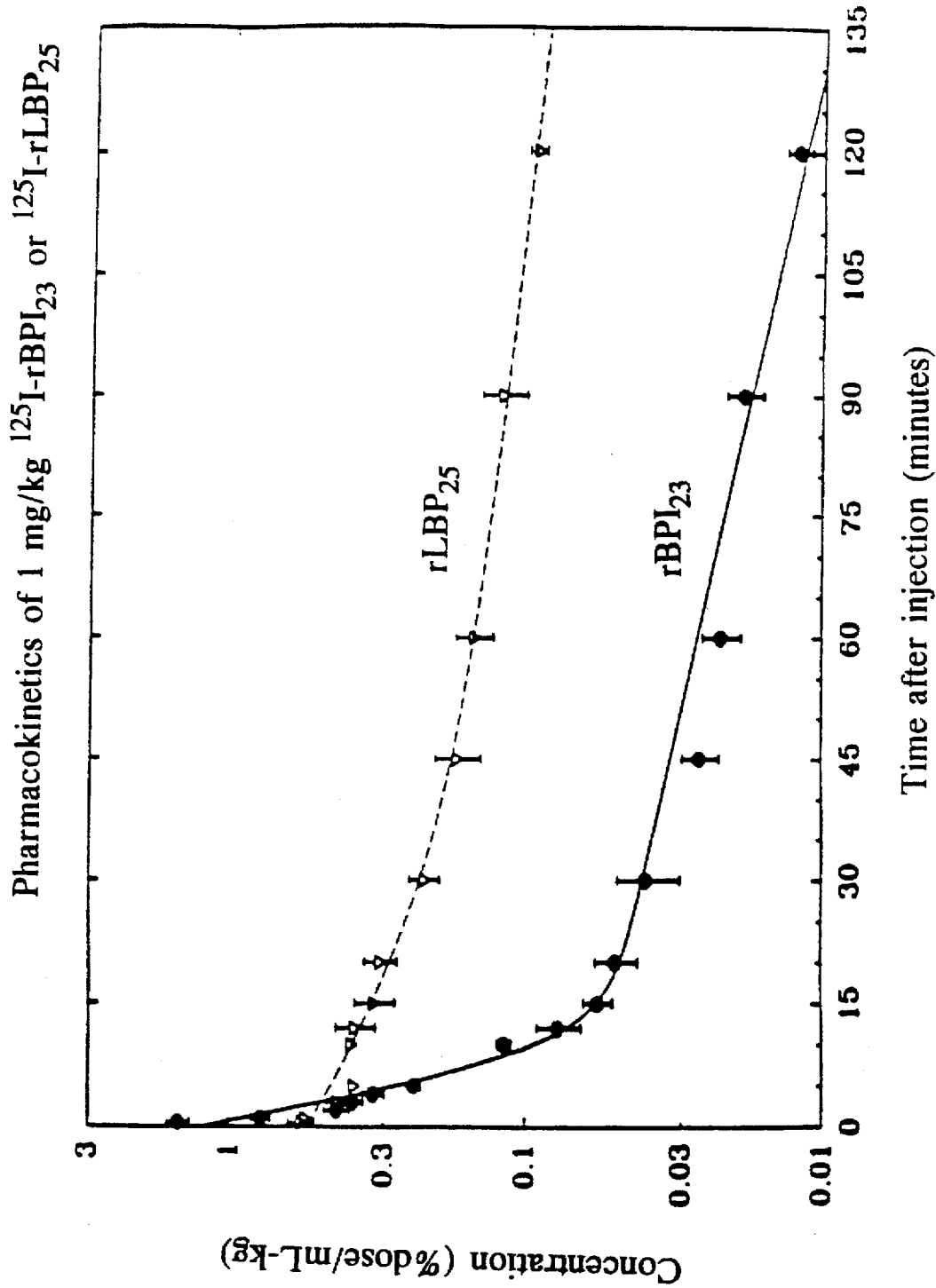
FIG. 8 depicts a graph illustrating the pharmacokinetics of $^{125}$I labeled rLBP$_{25}$ and rBPI$_{23}$.

Plasmid pING4505 was digested with EarI and SstII and the 135 bp fragment corresponding to LBP 158–197 (plus stop condon) was gel purified. This fragment was ligated with 2 fragments from pIC110, the 250 bp AflII-EarI fragment and the vector fragment (SstII-AflII) to generate pIC112 as set out in FIG. 7.

B. Construction of Mammalian Expression Vector pING4526.

Figure 5:
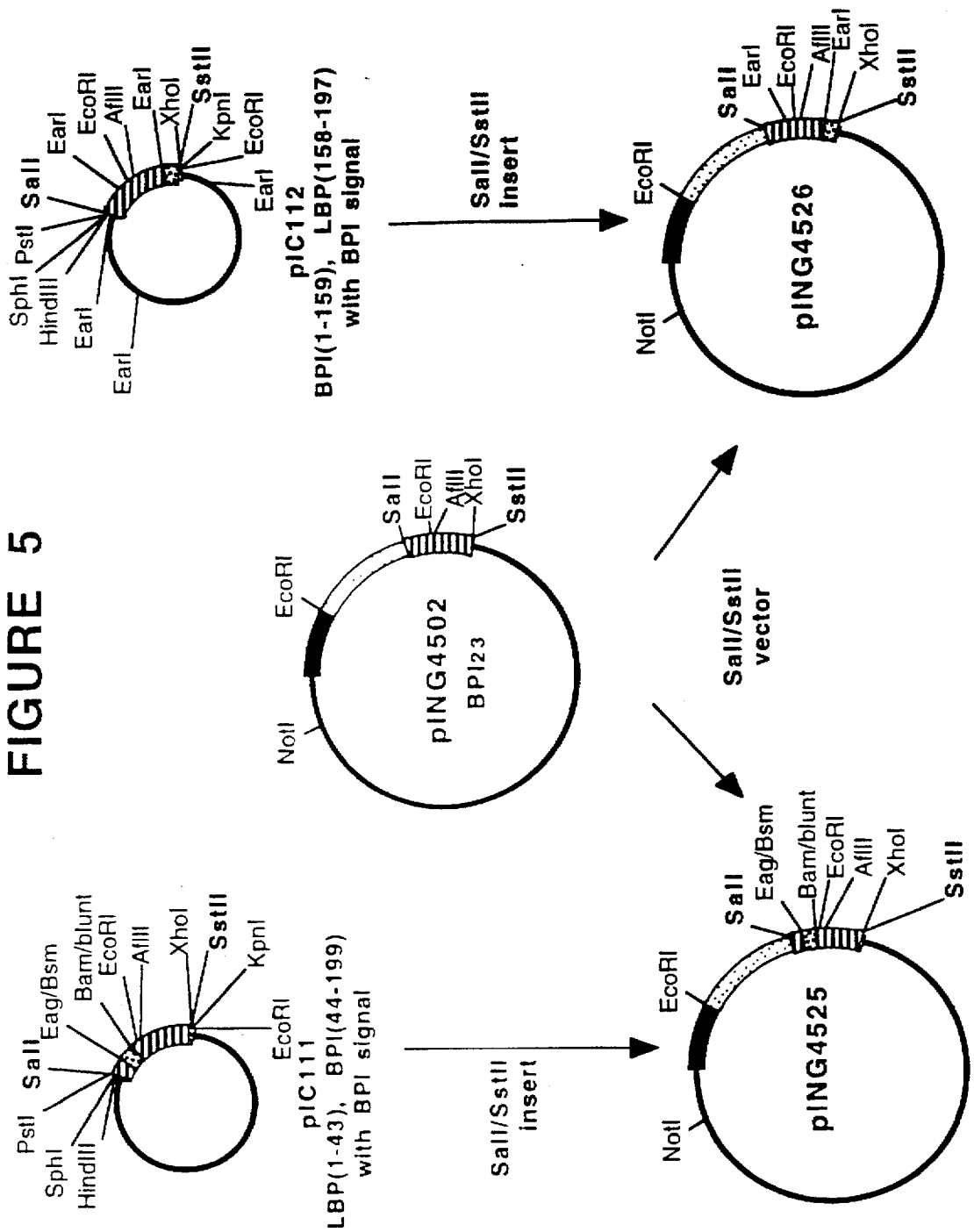
FIG. 5 depicts construction of mammalian expression vectors pING4525 and pING4526 for LBP/BPI hybrid proteins.

The insert encoding BPI (1–159)/LBP (158–197) was excised from pIC112 with SalI and SstII and subcloned into SalI-SstII digested pING4502 to generate pING4526 as set out in FIG. 5.

C. Construction of Vector for In Vitro Transcription/ Translation (pML103)

pING4526 was used as the source of a 430 bp EcoRI-SstII fragment (encoding BPI 61–159/LBP 158–197). This fragment was subcloned into the SstII-EcoRI vector fragment from pIC127 to generate pML103, encoding the BPI (1–159)/LBP (158–197) insert in a vector for in vitro transcription. This construction is set out in FIG. 6.

EXAMPLE 7

In Vitro Transcription/Translation and Lipid A Binding Activity of LBP/BPI Hybrid Protein In this example, in vitro transcription/translation reactions were carried out for plasmids encoding BPI$_{23}$ and the LBP/BPI hybrid proteins of Examples 5 and 6. Specifically, the TNT™ Coupled Reticulocyte Lysate System Kit (Promega, WI) with SP6 RNA polymerase was used to carry out in vitro transcription/translation of plasmids pML103 and pML105 to produce hybrid LBP/BPI proteins. The kit is a complete system, which provides all the reagents necessary to make protein. One adds only the DNA template specifying the protein sequence of interest, a radiolabeled amino acid ($^{35}$S-methionine) and a ribonuclease inhibitor (Promega's recombinant RNasin).

The protocol used to generate the LBP/BPI hybrid proteins was essentially that suggested by Promega's Technical Bulletin #126. Reactions were prepared in volume of 50 μL containing: TNT Rabbit Reticulocyte Lysate, TNT Reaction Buffer, TNT SP6 RNA Polymerase, amnino acid mixture minus Methionine, $^{35}$-S Methionine used was in vivo cell labelling grade purchased from Amersham (catalog #SJ.1015). One microgram of DNA from either pML103 or pML105 was put into the in vitro transcription-translation system. As specified by Promega, the transcription-translation reactions were incubated for 2 hours in a water bath at 30° C., then analyzed in various ways to assess the protein products made.

The amounts and molecular weights of the LBP/BPI hybrid proteins were determined by SDS PAGE/Phosphorimager analysis (Molecular Dynamics, CA), TCA precipitation and ELISA. The binding of the LBP/BPI hybrid proteins to immobilized J5 Lipid A was also measured.

A BPI sandwich ELISA was carded out using rabbit anti-BPI as the capture antibody on the plate and biotin labeled anti-BPI followed by alkaline phosphatase conjugated to streptavidin as the detection system.

A J5 Lipid A binding (RIA) binding assay was carded out using pop-apart Iratoulon-2 strips coated overnight with 25 ng per well of J5 Lipid A. Two sets of plates (coated and uncoated) were blocked for three hours at 37° C. with 0.1% BSA/PBS, washed with PBS/0.05% Tween, then binding was done at 37° C. for one hour with 50 μL of a 1:25 dilution of the transcription-translation reactions. After binding, plates were washed, then placed in scintillation vials with 2 mL of scintillation fluid and counted in a (Beckman) beta-counter.

Comparable amounts of LBP/BPI hybrid protein of the anticipated molecular weight were made for each of the analogs. However, when the total protein in each reaction was quantitated by ELISA, the yields appeared to differ. The absolute numbers obtained in the ELISA may reflect altered epitopes in the LBP/BPI hybrid proteins which may not be recognized equally by the rabbit anti-BPI antibody. In particular, the low amount of pML105 detected by ELISA is thought to underestimate the actual protein yield. The LBP/BPI hybrid proteins bound immobilized J5 Lipid A as well as $BPI_{23}$ (1–199) made with pIC127. Specific binding (background corrected) for the LBP/BPI hybrid proteins is shown in Table 2. LBP/BPI hybrid proteins of the invention may have such desired properties as LPS-binding activity comparable to $rBPI_{23}$, while lacking CD14-mediated immunostimulatory activity characteristic of the holo-LBP proteins, and may have advantageous pharmacokinetic properties such as increased half-life as compared with rBPI23 as measured in Example 8 below.

TABLE 2

| Plasmid | Description | Yield ELISA | Specific Binding RIA, J5 Lipid A |
|---------|-------------|-------------|----------------------------------|
| pIC127  | BP123 (1–199) | 57 ng | 140,000 cpms |
| pML103  | BPI (1–159) LBP (158–197) | 100 ng | 210,000 cpms |
| pML105  | LBP (1–43) BPI (44–199) | 12 ng | 150,000 cpms |

EXAMPLE 8

Pharmacokinetics of $rLBP_{25}$, rLBP and $rBPI_{23}$ in Male CD Rats (The pharmacokinetics of $rLBP_{25}$, rLBP and $rBPI_{23}$ were investigated in rats using an ELISA assay.) The pharmacokinetics of 1 mg/kg $rLBP_{25}$ was investigated in 3 male CD rats. Blood samples were collected at selected times (from 0.5 minutes to 72 hours) after administration of dose. Plasma samples were then assayed by ELISA using affinity purified rabbit anti-$LBP_{25}$ as the capture antibody and biotin labelled affinity purified rabbit anti-$LBP_{25}$ as the secondary antibody.

The plasma concentration-time profile of $rLBP_{25}$ could be fit to a three-compartment model, with α half-life of 2.3±0.3 minutes, β half-life of 10.8±1.0 minutes, and γ half-life of 101±14 minutes, with a systemic mean residence time of about 9.2±0.8 minutes (Table 3). The rate of clearance of $rLBP_{25}$ from the plasma was about 10 times faster than that observed for rLBP, and about 5 times slower than the clearance rate of $rBPI_{23}$. Unlike BPI, removing the carboxy terminal end of LBP significantly increased its clearance rate. However, the steady state volume of distribution of $LBP_{25}$ is similar to that of LBP, suggesting that the distribution of LBP was not affected by this modification.

The pharmacokinetics of 1 mg/kg rLBP was investigated in 3 male CD rats. Blood samples were collected at selected times (from 0.5 minutes to 75 hours) after administration of dose. Plasma samples were then assayed by ELISA using affinity purified rabbit anti-$LBP_{25}$ as the capture antibody and biotin labelled affinity purified rabbit anti-$LBP_{25}$ as the secondary antibody.

The plasma concentration-time profile of rLBP could be fit to a three-compartment model, with α half-life of 14±2 minutes, β half-life of 130±16 minutes, γ half-life of 561±37 minutes (Table 3). The rate of clearance of rLBP from the plasma was very slow, about 60 times slower than $rBPI_{23}$.

TABLE 3

Pharmacokinetics Parameter Values from the Serum Clearance Curve of 1 mg/kg rBPI$_{23}$, rLBP$_{25}$ and rLBP
(mean ± se)

| Test Article | Vc mL/kg | Vss mL/kg | Clearance mL/min/kg | MRT minutes | $t_{1/2}$ α minutes | $t_{1/2}$ β minutes |
|---|---|---|---|---|---|---|
| rBPI$_{23}$ | 62.3 ± 15 | 78 ± 16 | 25.5 ± 5.4 | 3.0 ± 0.0 | 1.62 ± 0.06 | 18.0 ± 3.0 |
| rLBP$_{25}$ | 46.8 ± 0.6 | 269 ± 60 | 5.1 ± 0.4 | 51.8 ± 8.9 | 2.33 ± 0.3 | 10.8 ± 1.0 |
| rLBP | 55.7 ± 9.0 | 208 ± 77 | 0.45 ± 0.1 | 437.6 ± 55 | 13.57 ± 2.0 | 129.7 ± 16 |

Vc = volume of distribution of the central compartment.
Vss = steady state volume of distribution.
MRT = total body mean residence time.
$t_{1/2}$ α = alpha half-life.
$t_{1/2}$ β = beta half-life.

EXAMPLE 9

Binding of rLBP$_{25}$ and rLBP to Lipid A

In this example, the binding of rLBP$_{25}$ to immobilized lipid A was determined according to the method of Gazzano-Santoro et al., Infect. Immun. 60: 4754–4761 (1992) but utilizing $^{125}$I labeled rLBP$_{25}$ instead of $^{125}$I labeled rBPI$_{23}$. Radioiodination of proteins was performed essentially as previously described (Gazzano-Santoro et al.) except that the iodination was performed in the absence of Tween 20 and the iodinated protein was exchanged by gel filtration into 20 mM citrate, pH 5.0, 0.15M NaCl, 0.1% F68 (Poloxamer 88) 0.002% Polysorbate 80.

Figure 9:
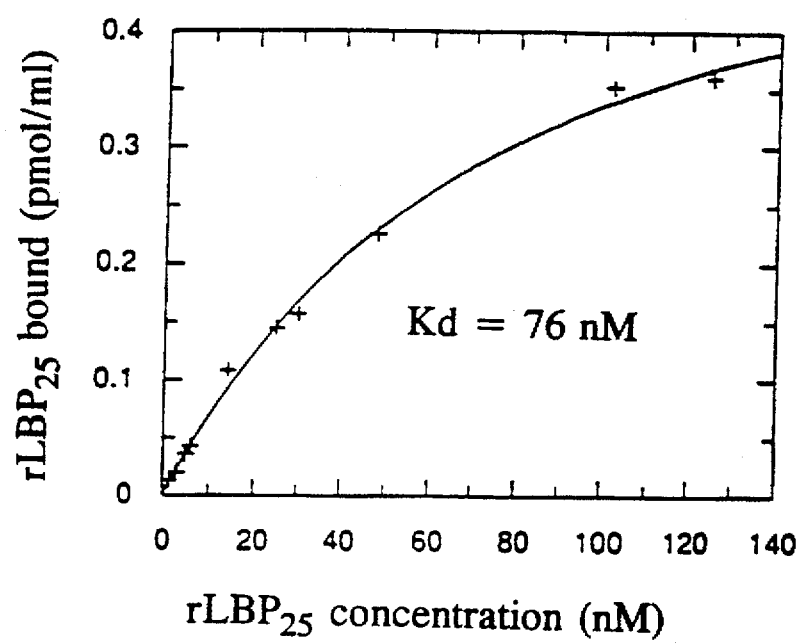
FIG. 9 depicts binding of rLBP$_{25}$ to $E.$ $coli$ J5 lipid A.

Specifically, an E. colt. J5 lipid A suspension was sonicated, diluted in methanol to a concentration of 0.1 µg/mL and 100 µL aliquots were allowed to evaporate in wells (Immulon 2 Removawell Strips, Dynatech) at 37° C. overnight. The wells were then blocked with 215 µL of D-PBS/0.1% BSA (D-PBS/BSA) for three hours at 37° C. The blocking buffer was discarded, the wells were washed in D-PBS/0.05% Tween 20 (D-PBS/T) and incubated overnight at 4° C. with D-PBS/T containing increasing amounts of $^{125}$I labeled rLBP$_{25}$, or rBPI$_{23}$ as described in Gazzano-Santoro et al. After three washes, bound radioactivity was counted in a gamma counter. The binding to wells treated with (D-PBS/BSA) only was taken to represent nonspecific binding; specific binding was defined as the difference between total and nonspecific binding. For rLBP, the experiment was performed as described above except that the wells were blocked in D-PBS/1%BSA, washed with D-PBS/0.1%BSA and the binding incubation buffer was D-PBS/0.1% BSA. The resulting data were fitted to a standard binding equation by computerized non-linear curve fitting (Leatherbarrow, Trends Biochemical Sciences, 15:455–458 (1990); GraFit Version 2.0, Erathicus Software Ltd., Staines, UK). According to these experiments the labeled rLBP$_{25}$ had a K$_d$ of about 76 nM (FIG. 9) and the rLBP had a K$_d$ of about 60 nM, while rBPI$_{23}$ had a K$_d$ of approximately 3 nM, indicating an approximately 15–25 fold lower binding affinity of rLBP25 and rLBP, as compared with rBPI$_{23}$, for LPS. However, the binding of rLBP$_{25}$ and rLBP were comparable, demonstrating that the LBS-binding site of rLBP is localized in the N-terminal portion of the molecule.

EXAMPLE 10

Figure 10:
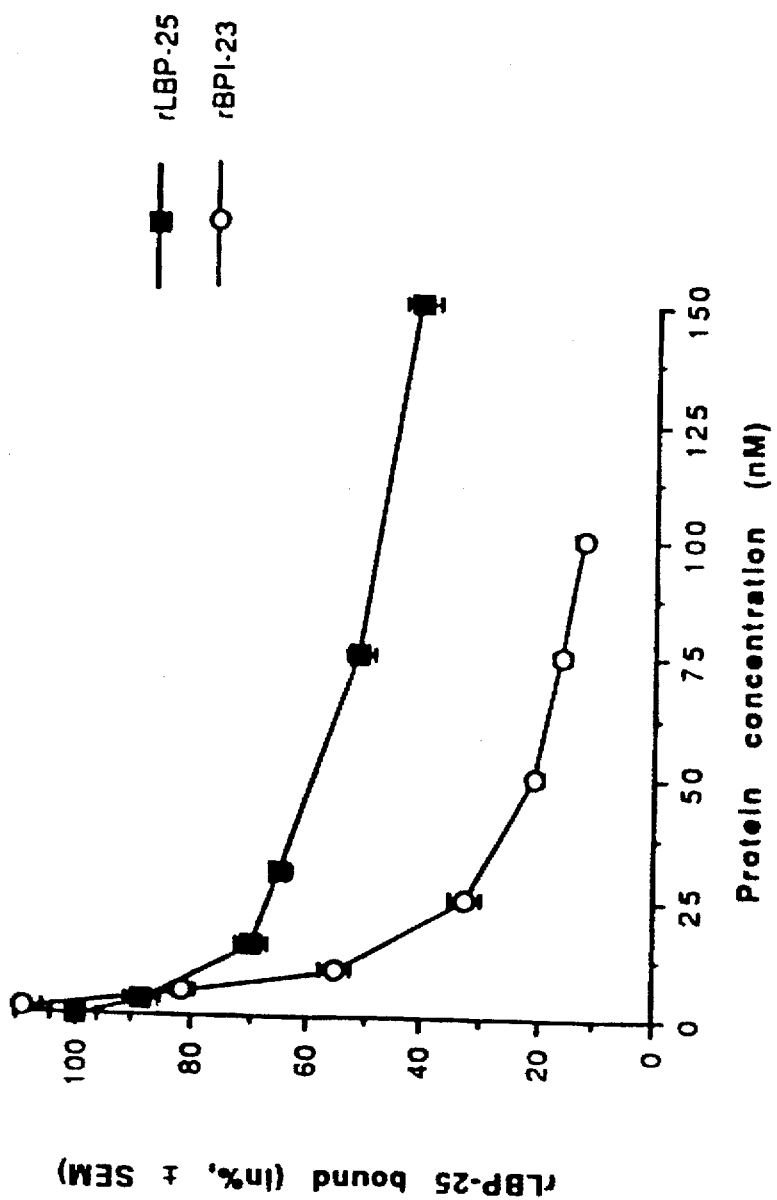
FIG. 10 depicts competition by rBPI$_{23}$ and by rLBP$_{25}$ for the binding of $^{125}$I-rLBP$_{25}$ to immobilized lipid A.

Competition by rBPI$_{23}$ and by rLBP$_{25}$ for the Binding of $^{125}$I-rLBP$_{25}$ to Immobilized Lipid A In this example, the inhibition of $^{125}$I-labeled rLBP$_{25}$ binding to E. coli J5 lipid A by unlabeled rBPI$_{23}$ or rLBP$_{25}$ was determined. Specifically, E. coli J5 lipid A was diluted in methanol to a concentration of 1 µg/mL and 50 µL aliquots were allowed to evaporate in wells overnight at 37° C. The wells were then blocked in D-PBS/BSA. Increasing amounts of unlabeled rBPI$_{23}$ or rLBP$_{25}$ in a 50 µL volume were then added and the wells were incubated overnight at 4° C. in D-PBS/T. Twenty microliters of $^{125}$I-rLBP$_{25}$ (0.65× 10$^6$ cpm, specific activity 5.29 µCi/µg) were added directly to each well and further incubated for one hour at 4° C. After three washes in D-PBS/T, wells were counted. FIG. 10 shows that although rLBP$_{25}$ is able to compete with $^{125}$I-rLBP$_{25}$ for binding to lipid A, rBPI$_{23}$ is a better competitor. These results are consistent with the difference in relative affinity as shown in Example 9.

EXAMPLE 11

Figure 11:
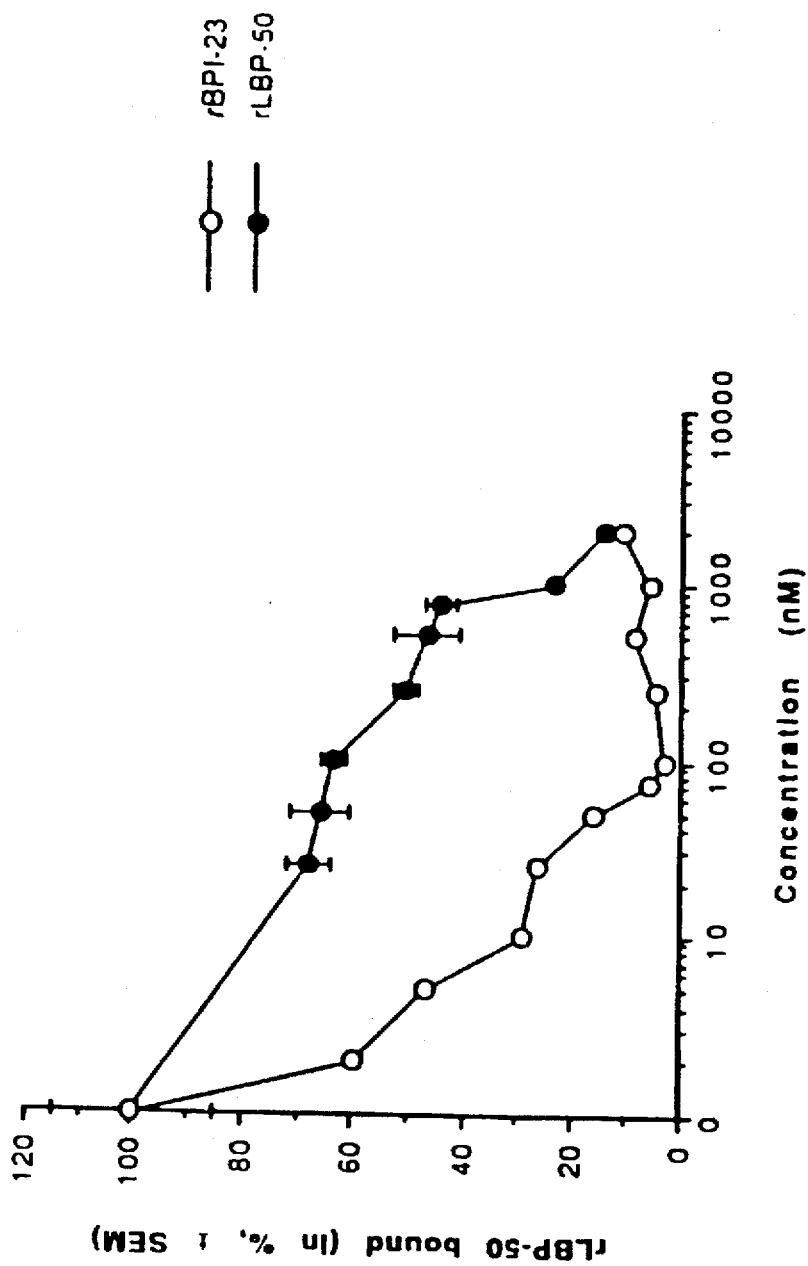
FIG. 11 depicts competition by rBPI$_{23}$ and by recombinant LBP holoprotein (rLBP) for the binding of $^{125}$I-rLBP to immobilized lipid A.

Competition by rBPI$_{23}$ and by rLBP for the Binding of $^{125}$I-rLBP to Immobilized Lipid A In this example, the inhibition of $^{125}$I-labeled rLBP binding to E. coli J5 lipid A by rBPI$_{23}$ and rLBP was determined. Specifically, E. coli J5 lipid A was diluted in methanol to a concentration of 1 µg/mL and 100 µL aliquots were allowed to evaporate in wells overnight at 37° C. Following incubation, the wells were blocked in D-PBS/1%BSA. Increasing amounts of unlabeled rBPI$_{23}$ or rLBP mixed with a fixed amount of $^{125}$I-rLBP (1.45×10$^6$ cpm, specific activity 1.74 µCi/µg) were added to wells in a 100 µL volume and incubated overnight at 4° C. in D-PBS/BSA. After three washes in D-PBS/BSA, wells were counted. FIG. 11 shows the results wherein increasing amounts of both rLBP and rBPI$_{23}$ compete with radiolabeled rLBP binding for the immobilized lipid A. These results show that rBPI$_{23}$ was more potent than rLBP at competing for rLBP (FIG. 11) binding to lipid A consistent with the difference in relative affinity as shown in Example 9.

EXAMPLE 12

Ability of rLBP$_{25}$ and rLBP to Inhibit the LAL Assay

Figure 12:
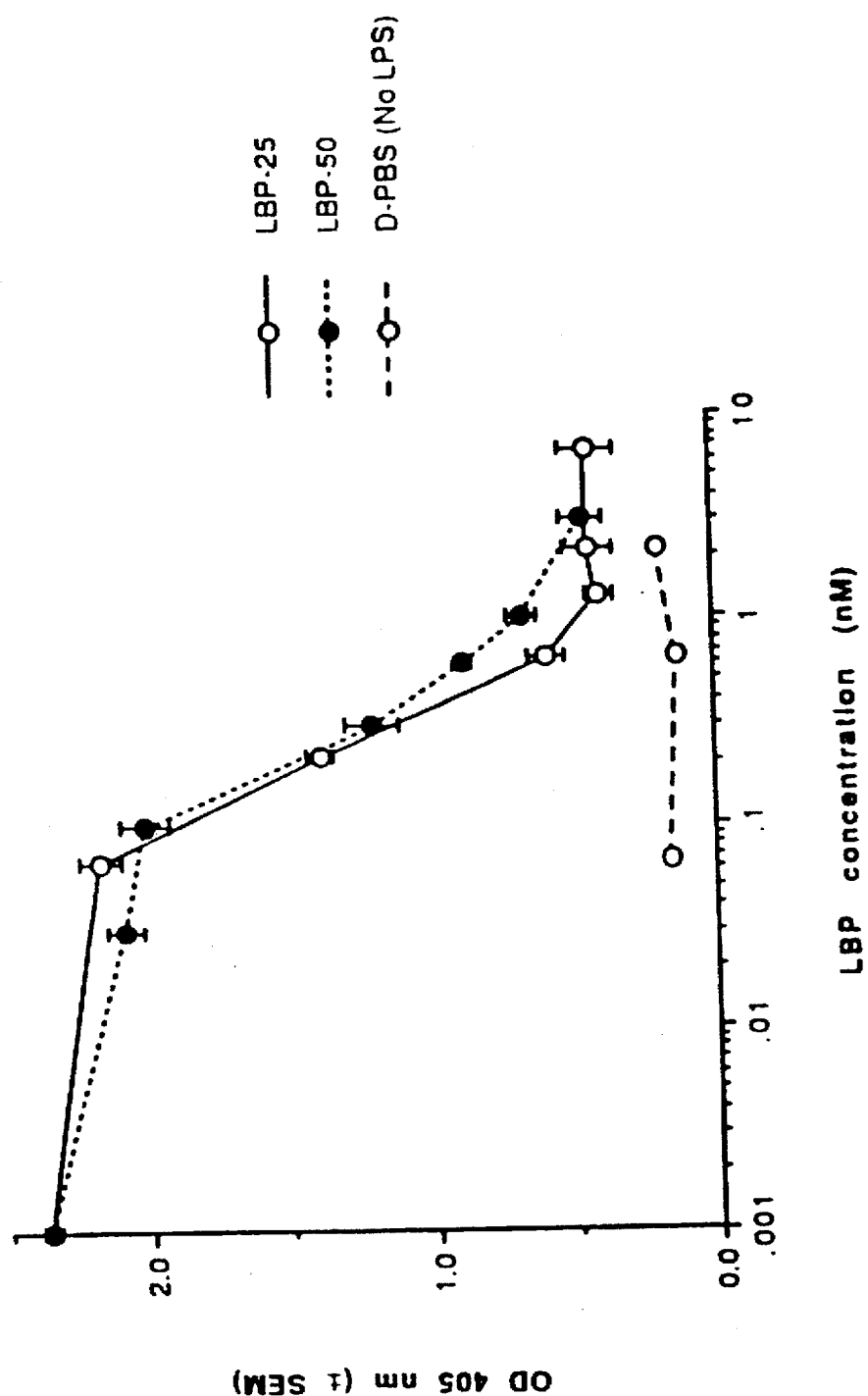
FIG. 12 depicts the ability of rLBP$_{25}$ and rLBP to inhibit the LAL assay.

In this example, the effect of rLBP$_{25}$ and rLBP were compared for their ability to inhibit the Limulus amebocyte lysate (LAL) assay. Specifically, increasing concentrations of the LPS binding proteins were incubated in the presence of 2 ng/mL of E. coli 0113 LPS (60 µL volume) for three hours at 37° C. The samples were then diluted with PBS to bring the LPS concentration to 333 pg/mL and the amount of LPS activity was determined in the chromogenie LAL assay (Whittaker Bioproducts, Inc.). The results shown in FIG. 12 show that rLBP$_{25}$ and the rLBP protein products had comparable endotoxin neutralizing activity in the LAL assay.

EXAMPLE 13

Effect of LBP Molecules on Binding/Uptake of $^{125}$I-labeled LPS and on TNF Production by THP-1 Cells In this example, the effect of rLBP$_{25}$ and rLBP on binding/uptake of LPS and TNF production by a human monocyte cell line bearing CD14 receptors on its cell surface was determined. Specifically, THP-1 human monocyte cells (obtained from the American Type Culture Collection Tumor Immunology Bank, 12301 Parklawn Dr., Rockville, Md. 20852) were grown to a density of $3.5 \times 10^5$/mL in RPMI 1640 media (Gibco Laboratories, Grand Island, N.Y.) supplemented with 10% heat-inactivated fetal bovine serum (Hyclone Laboratories, Logan, Utah), 1 mM glutamine, 1 mM pyruvate (Gibco), and 10U/mL penicillin and streptomycin (Gibco). The cells were transferred at the same density into the above medium supplemented with 100 nM 1,25 dihydroxyvitamin D$_3$ (Biomol Research Laboratories, Plymouth Meeting, PA) and allowed to grow for another 3 days before use. Tubes containing $2 \times 10^6$ cells in 1 mL of RPMI/0.1% BSA were incubated in the presence of 20 ng/mL of $^{125}$I-labeled Ra LPS (List Biological Laboratories, Campbell Calif.) with various concentrations of rLBP$_{25}$, or rLBP. Nonspecific uptake was determined by adding a 2000-fold excess of unlabeled RaLPS for one hour at 37° C. At the end of the incubation time, the cells were removed from the binding medium by centrifugation through a layer of dibutyl/dioctyl phthalate oil and counted. Supernatants were sampled at the end of the assay to determine TNF production.

Figure 13:
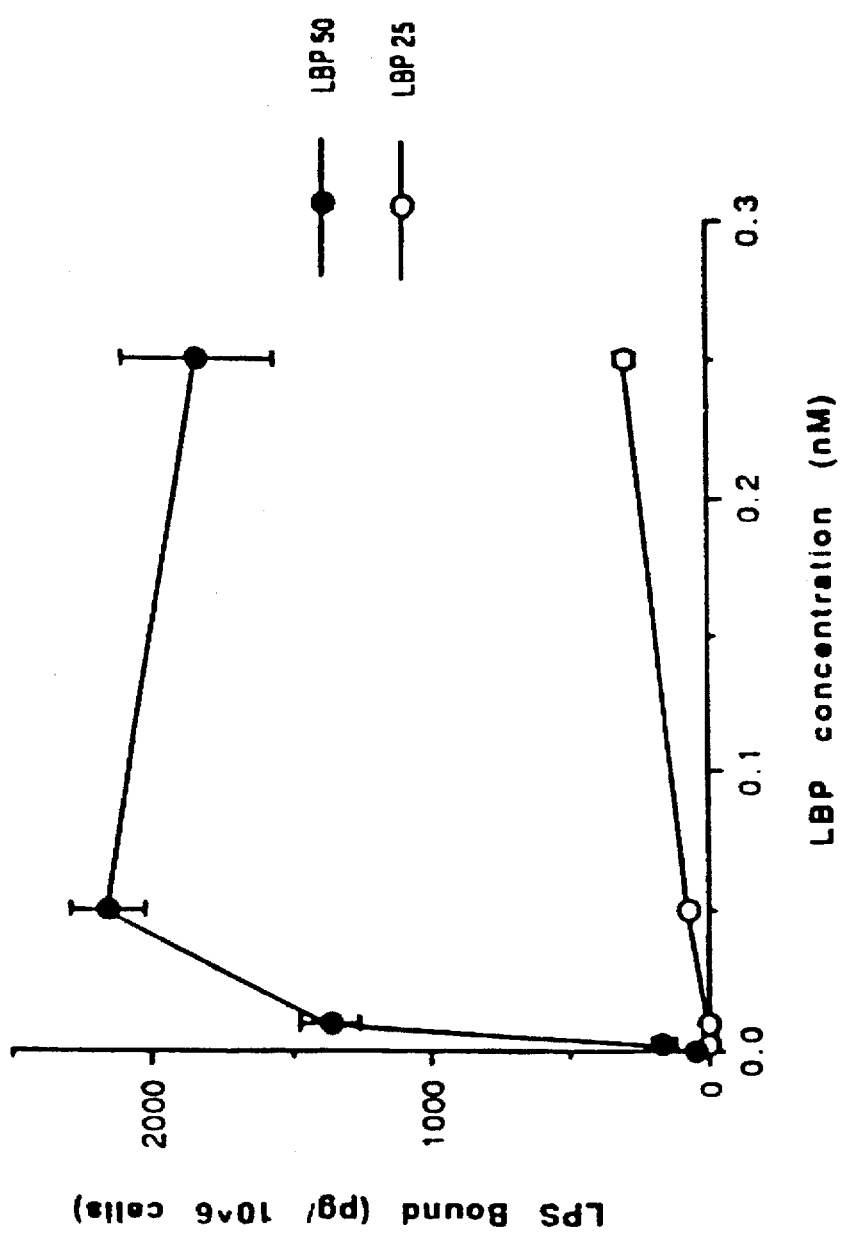
FIG. 13 depicts the effect of rLBP$_{25}$ and rLBP on binding uptake of $^{125}$I-labeled LPS by THP-1 cells.
Figure 14:
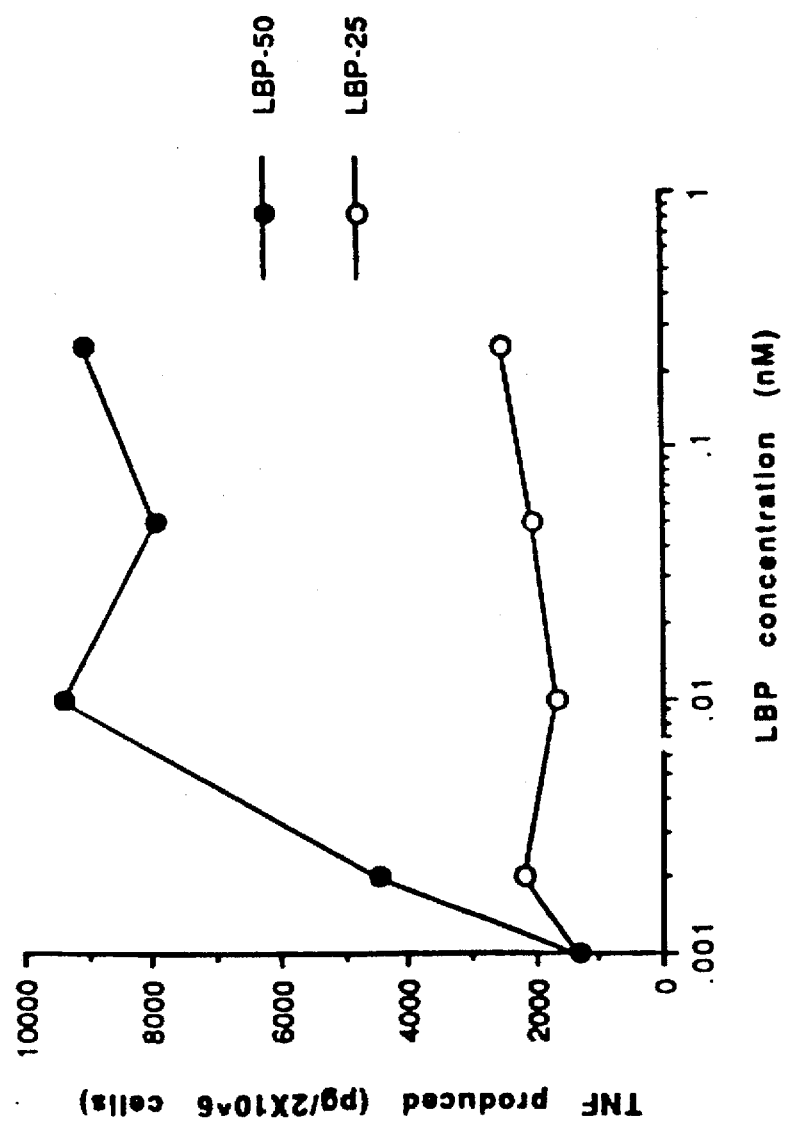
FIG. 14 depicts the effect of rLBP$_{25}$ and rLBP molecules on TNF production by THP-1 cells.

The presence of rLBP stimulated both the uptake of 125I-labeled LPS (FIG. 13) and the release of TNF (FIG. 14) by the THP-1 cells. In contrast, if the cells are incubated with rLBP$_{25}$, there was no significant uptake of $^{125}$I-labeled LPS (FIG. 13) and no significant TNF production (FIG. 14).

EXAMPLE 14

Effect of LBP Molecules on TF and TNF Production in PBMCs

In this example, peripheral blood mononuclear cells (PBMCs) isolated from healthy human donors were used in a model system to determine the effects of rLBP$_{25}$ and rLBP on LPS-mediated effects. PBMCs include approximately 20% monocytes which are known to produce tissue factor (TF) which is a cell surface protein responsible for initiating blood clotting and tumor necrosis factor (TNF) when stimulated by LPS Tissue Factor if assembled with factor VII initiates the blood coagulation cascades. TF activity induced by LPS has been implicated in the pathogenesis of disseminated intravascular coagulation (DIC), which is a major complication of gram-negative sepsis. Bone, *Annals Int. Med.* 115:457 (1991).

According to the experimental protocol, PBMCs were prepared from buffy coat from the blood of healthy human donors by separation over Ficoll-Hypaque. The percentage of monocytes (15–25%) in different PBMC preparations was determined by fluorescence activated cell sorting (FACS) analysis based on the expression of CD14 antigen. The PBMCs ($2 \times 10^6$/mL) were incubated in 1 mL Dulbecco's modified Eagle medium containing 25 mM HEPES, at 37° C., 5% CO$_2$ for 4 hours. During this incubation, LPS in varying concentrations is present with varying concentrations of rLBP or rLBP$_{25}$ or 20% fetal bovine serum (FBS). After incubation the cells and media were separated by centrifugation. The cells were washed with Tris-NaCl buffer (0.1M Tris, 0.15M NaCl, 0.1% bovine serum albumin, pH7.4) then lysed in the same buffer by adding 15 mM octyl-beta-D-glycopyranoside and incubated at 37° C. for 30 minutes.

To determine TNF production by the PBMCs incubated as described above, the supernatant of the PBMCs was assayed for TNF by ELISA (T Cell Sciences, Cambridge, Mass.).

To determine TF production, total cellular TF activity was determined in the PBMC lysate using a two-stage amidolytic assay, similar to that described by Moore et al., *J. Clin. Invest.* 79: 124–130 (1987). In the first stage, the PBMC lysate was mixed with coagulation factor VII and factor X, in order to combine TF with factor VII, which in turn, activated factor X. In the second stage the activity of factor Xa was measured using a chromogenic peptide substrate. Factor VII, factor X and this synthetic peptide substrate (Spectrozyme FXa [MeO-CO-D-CHG-Gly-Arg-pNA)] were the products of American Diagnostica, Greenwich, Conn. TF activity was calculated by reference to standard curves obtained with dilutions of rabbit brain thromboplastin (Sigma Chemical Co., St. Louis, Mo.) in the amidolytic assay.

For this assay in a 96 well microtiter plate, cell lysate (containing $10^3$–$10^4$ monocytes) or different dilutions of the thromboplastin standard (corresponding to 0.1 to 1 μl buffer (0.1M Tris, 0.15M NaCl, pH 7.4) containing 7 mM CaCl$_2$. The mixture was incubated at room temperature for 20 min. Then 50 μl of Spectrozyme FXa, (synthetic substrate for factor Xa; 1.4 mg/ml) was added and the rate of absorbance increase at 405 mn was measured using a kinetic plate reader (Molecular Devices, Menlo Park, Calif.).

Figure 15A:
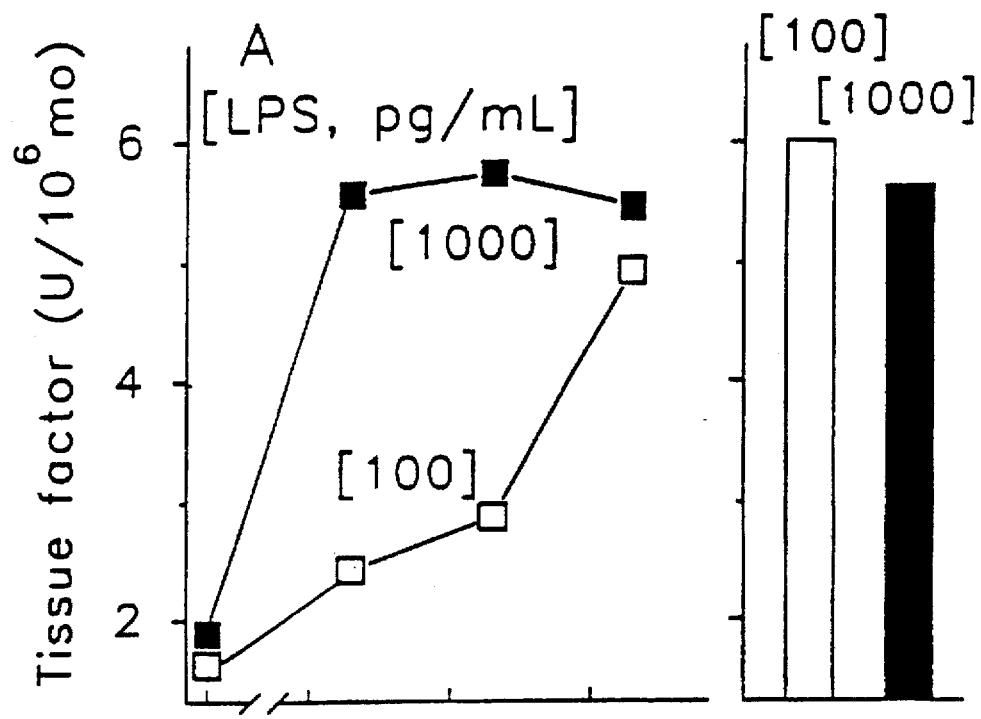
FIGS. 15A and 15B depict the effect of rLBP on Tissue Factor (TF) and TNF production, respectively, in PBMCs.
Figure 15B:
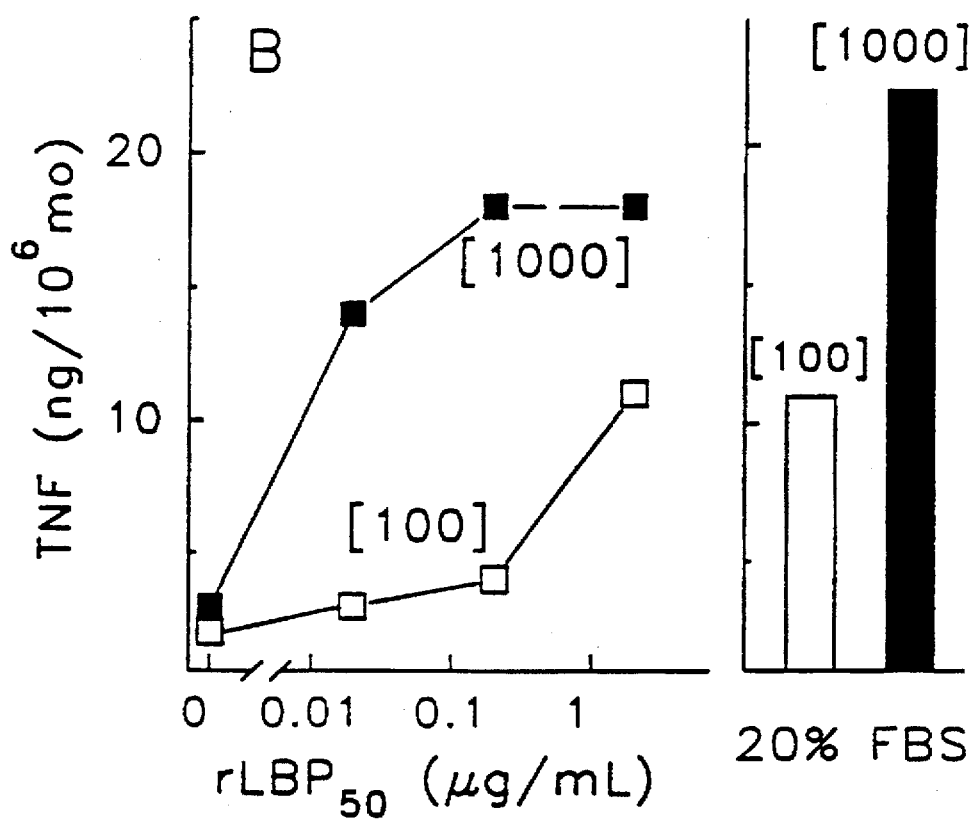

According to one experiment, varying amounts of recombinant rLBP (produced according to the method of Example 3) and 100 or 1000 pg/ml of *E. coli* LPS were contacted with the isolated PBMCs to determine the effect of rLBP on the appearance of TF in the cell lysate and on TNF release. The results in FIGS. 15a and 15b show that rLBP greatly stimulates the LPS-mediated synthesis of TF and TNF. Similarly, incubation of LPS (100 or 1000 pg/ml) and 20% fetal bovine serum (FBS) also resulted in TF and TNF synthesis. Since LBP is present in serum, the bar-graphs at the right of FIGS. 15a and 15b show that serum also mediates LPS mediated responses of TF and TNF production. To determine whether the effects of LPS are mediated by the CD14 antigen present on the surface of monocytes, antibodies to this determinant were included in the incubation mixture in other experiments. Addition of anti-CD14 monoclonal antibody (MY4; Coulter Immunology, Hialeah, Fla.) in the presence of serum or rLBP inhibited the induction of both tissue factor activity and TNF release. The extent of inhibition diminished at higher LPS concentrations.

Figure 16:
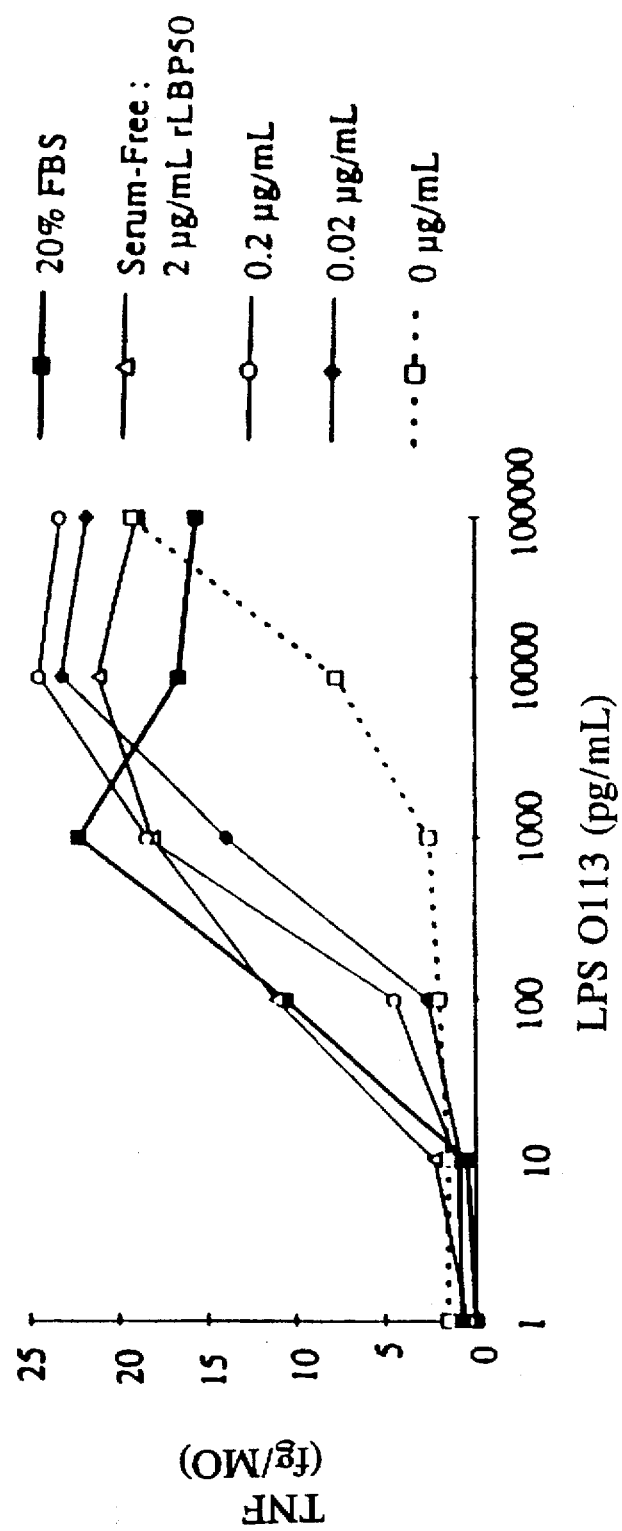
FIG. 16 depicts the effect of rLBP on TNF production in PBMCs.
Figure 17:
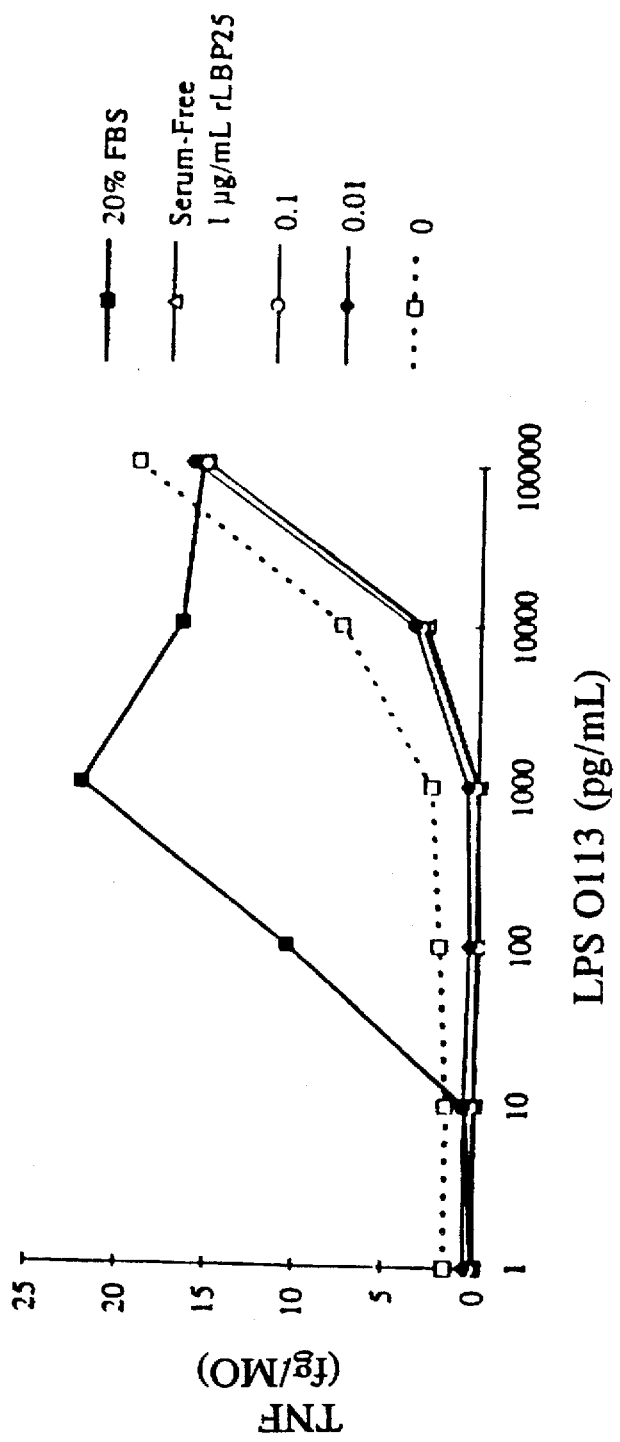
FIG. 17 depicts the effect of rLBP$_{25}$ on TNF production in PBMCs.

The use of the PBMC model to determine TF and TNF production was then repeated to compare the effect of rLBP$_{25}$ with that of recombinant rLBP on LPS-induced TF and TNF production. The results with varying concentrations of LPS shown in FIG. 16 compare administration of 20% FBS with serum-free media containing various concentrations of recombinant rLBP. These results again demonstrate that rLBP potentiates TNF release. The results shown in FIG. 17 with varying concentrations of LPS compare administration of 20% FBS with varying concentrations of rLBP$_{25}$ in serum-free media. In contrast to the results with rLBP, these results demonstrate that rLBP$_{25}$ does not have an immunostimulatory effect and therefore does not potentiate the release of TNF.

Figure 18:
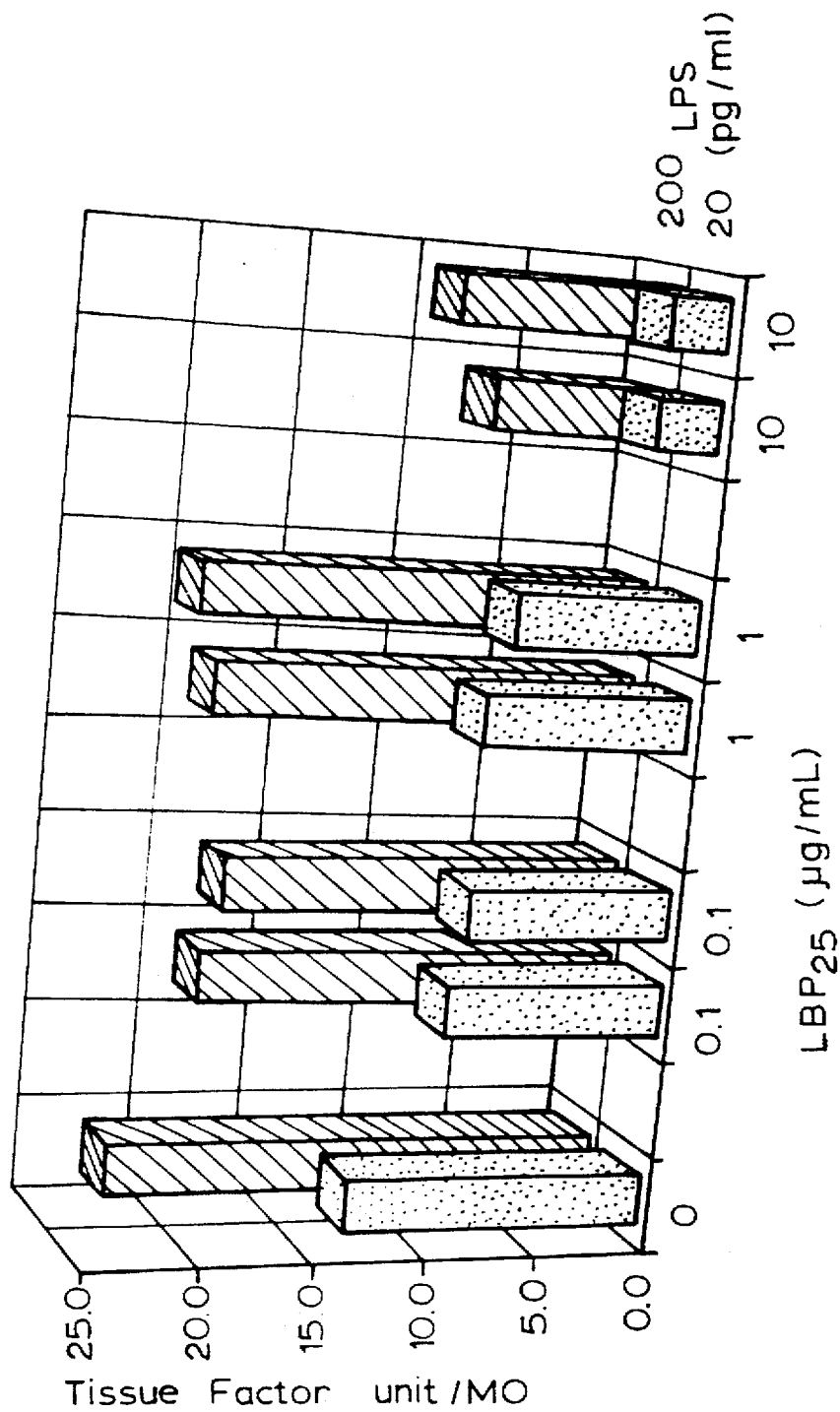
FIG. 18 depicts the effect of LBP molecules on Tissue Factor production in PBMCs.

Although rLBP$_{25}$ could not mediate the CD14-dependent LPS stimulation of monocytes to produce TF or TNF, the ability of rLBP$_{25}$ to compete with rLBP and inhibit the LPS-mediated appearance of TF on the PBMC cell surface was tested. Specifically, rLBP$_{25}$ produced according to the method of Example 4 was added in concentrations ranging from 0.1 to 10.0 µg/mL to PMBCs that were incubated with a constant amount of rLBP (2 µg/ml) and stimulated with either 20 pg/mL or 200 pg/mL LPS. The results shown in FIG. 18 demonstrate that not only does rLBP$_{25}$ not mediate LPS-stimulated TF production similar to rLBP but also it effectively competes with rLBP to substantially reduce the LPS-induced TF production. Similar effects were obtained for TNF production.

EXAMPLE 15

Figure 19:
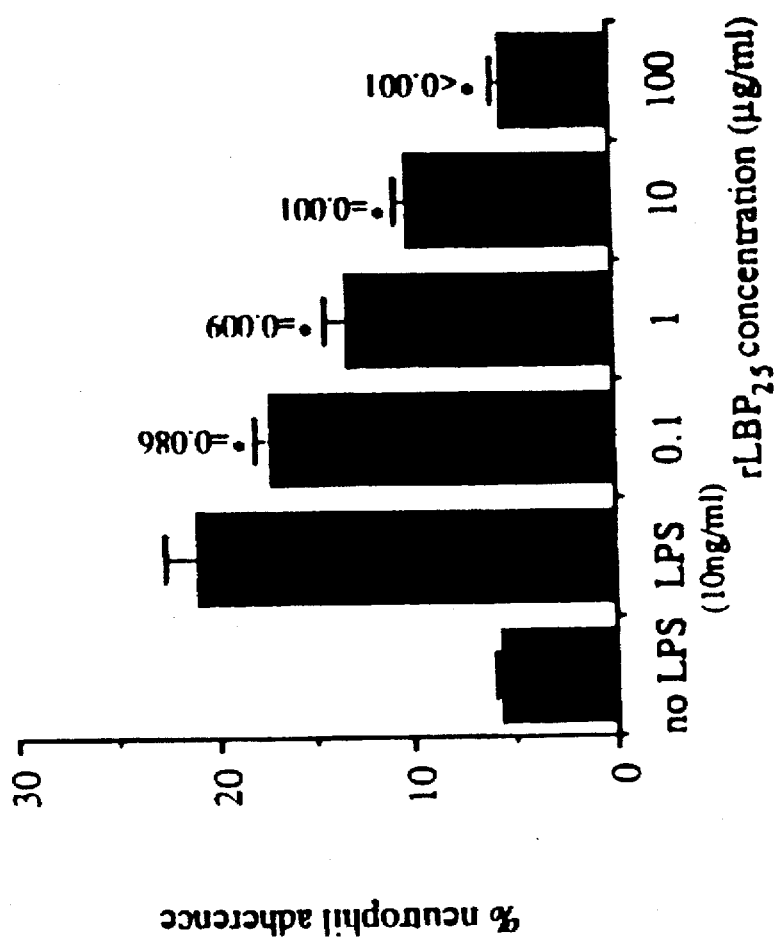
FIG. 19 depicts the effect of rLBP$_{25}$ on LPS induced endothelial adhesiveness for neutrophils.

Effect of rLBP$_{25}$ on LPS Induction of Endothelial Cell Adhesiveness for Neutrophils In this example, the effect of rLBP$_{25}$ on LPS induction of endothelial cell adhesiveness for neutrophils was studied in an in vitro adherence assay. Human umbilical cord endothelial cells (HUVEC) were cultured in a 48-well plate and incubated for 4 hours at 37° C. with 10 ng/mL LPS (*E. coli* 0113) in M199 supplemented with 2% FCS, or with the medium only. rLBP$_{25}$ was added to the LPS-containing wells at concentrations varying frown 0.1 to about 100 µg/mL to determine its ability to neutralize the LPS-induced increase in the adhesiveness of endothelial cells. Following the four hour incubation, HUVEC monolayers were washed three times, and 2.5×10$^5$ $^{51}$Cr-labeled human blood neutrophils in 0.2 mL RMPI-2% FCS were added to each well. The plate was incubated at 37° C. for 30 minutes. After the incubation, the supernatant was aspirated and each well was washed with 1 mL of warm medium to remove non-adherent neutrophils. The cells remaining in each well were solubilized with 0.2 mL of 0.25N NaOH and the lysates were counted in a gamma counter. Percent neutrophil adherence was calculated as 100×cpm lysate/cpm added. The data presented in FIG. 19 on the mean of percent neutrophil adherence of four replicates per group. The results shown in FIG. 19 demonstrate that rLBP$_{25}$ at 100 µg/ml completely inhibits the LPS-induced neutrophil adhesion. Under the conditions of this assay, 10 or 1 µg/mL of rLBP$_{25}$ inhibits 71% and 51%, respectively, of the LPS-stimulated adherence, while 0.1 µg/mL of rLBP$_{25}$ had no significant inhibitory effect.

EXAMPLE 16

Effect of rLBP and rLBP$_{25}$ on Bacteria Binding to Monocytes

In this example, the effect of rLBP$_{25}$ on bacterial binding to monocytes and polymorphonuclear neutrophils (PMNs) was compared with that of rLBP. White blood cells (WBC) were isolated by lysis with NH$_4$Cl of acid-citrate-dextran treated blood and red blood cell ghosts removed by washing. Bacteria were cultured overnight in Trypticase soy broth, washed extensively, incubated for 1 hour at room temperature with 1 mg/ml fluorescein isothiocyanate (FITC), and washed. Most strains were then incubated for 30 minutes at 60° C. and washed again. The concentration of bacterial cells was then determined turbidometrically.

In order to measure bacterial binding and uptake by WBC, WBC adjusted to 10$^7$/ml in pooled normal human serum (NHS) were mixed with a 5-fold excess of bacteria in NHS and incubated. Experiments were terminated by transferring the tubes to 4° C. and/or adding cytochalasin B. Cells were then washed extensively with ice cold DPBS and analyzed immediately on a FACScan (Becton Dickinson, San Jose, Calif.). Binding is defined as the percent of cells with bacteria at time zero. Uptake is defined as the percent of cells with bacteria after 15 minutes at 37° C. minus the percent of cells with bacteria at time zero.

Figure 20:
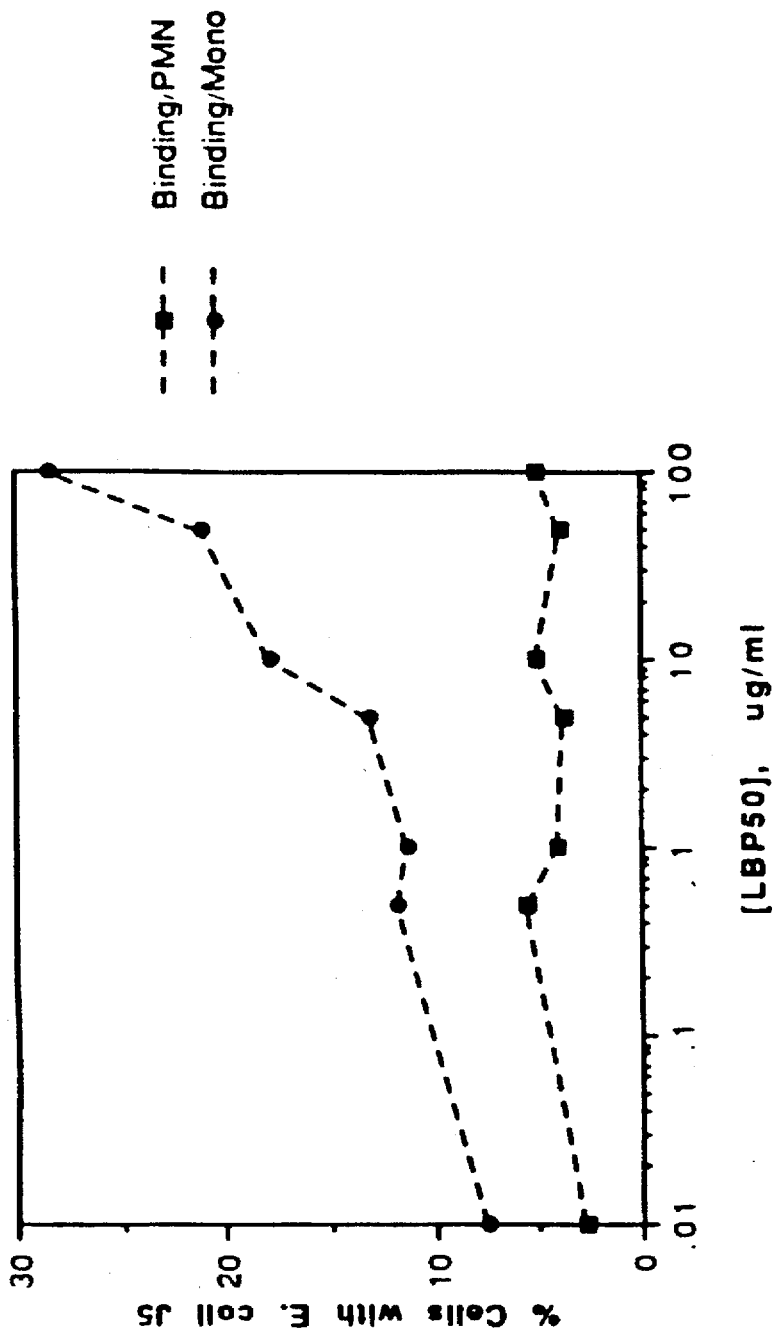
FIG. 20 depicts the effect of rLBP on bacterial binding to monocytes.
Figure 21:
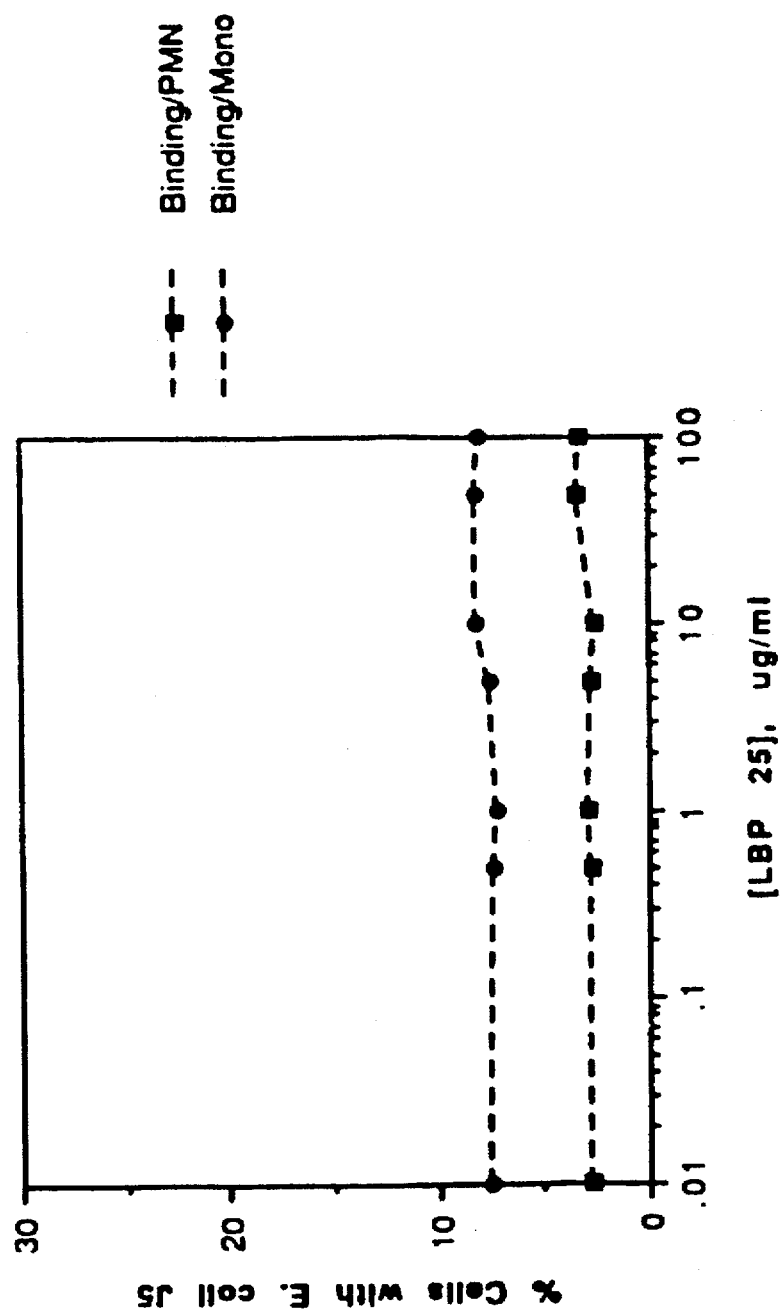
FIG. 21 depicts the effect of rLBP$_{25}$ on bacterial binding to monocytes.

For the determination of the effect of rLBP and rLBP$_{25}$ on bacterial binding to monocytes, isolated WBC in 100% allogeneic human serum mixed with *E. coli* J5 bacteria that had been pretreated with various concentrations of rLBP or rLBP$_{25}$. As shown in FIGS. 20 and 21, there was minimal binding (<10%) to either monocytes or PMNs by the bacteria in the absence of rLBP or rLBP$_{25}$. rLBP mediated a concentration-dependent binding of bacteria to monocytes, that reached 30% at 100 µg/mL rLBP (FIG. 20). This rLBP-enhanced binding of bacteria to monocytes was shown to be inhibited by an anti-CD14 monoclonal antibody (mAb MY4) but not by an isotype-matched control (mAb 5C2). In striking contrast, rLBP$_{25}$ was unable to mediate such a CD14-dependent enhanced binding to monocytes as induced by rLBP (FIG. 21). No comparable increase in binding to PMNs is mediated by either rLBP or rLBP$_{25}$. This finding is consistent with the much lower levels of CD14 on PMNs as opposed to monocytes.

EXAMPLE 17

LBP Sandwich ELISA

Figure 22:
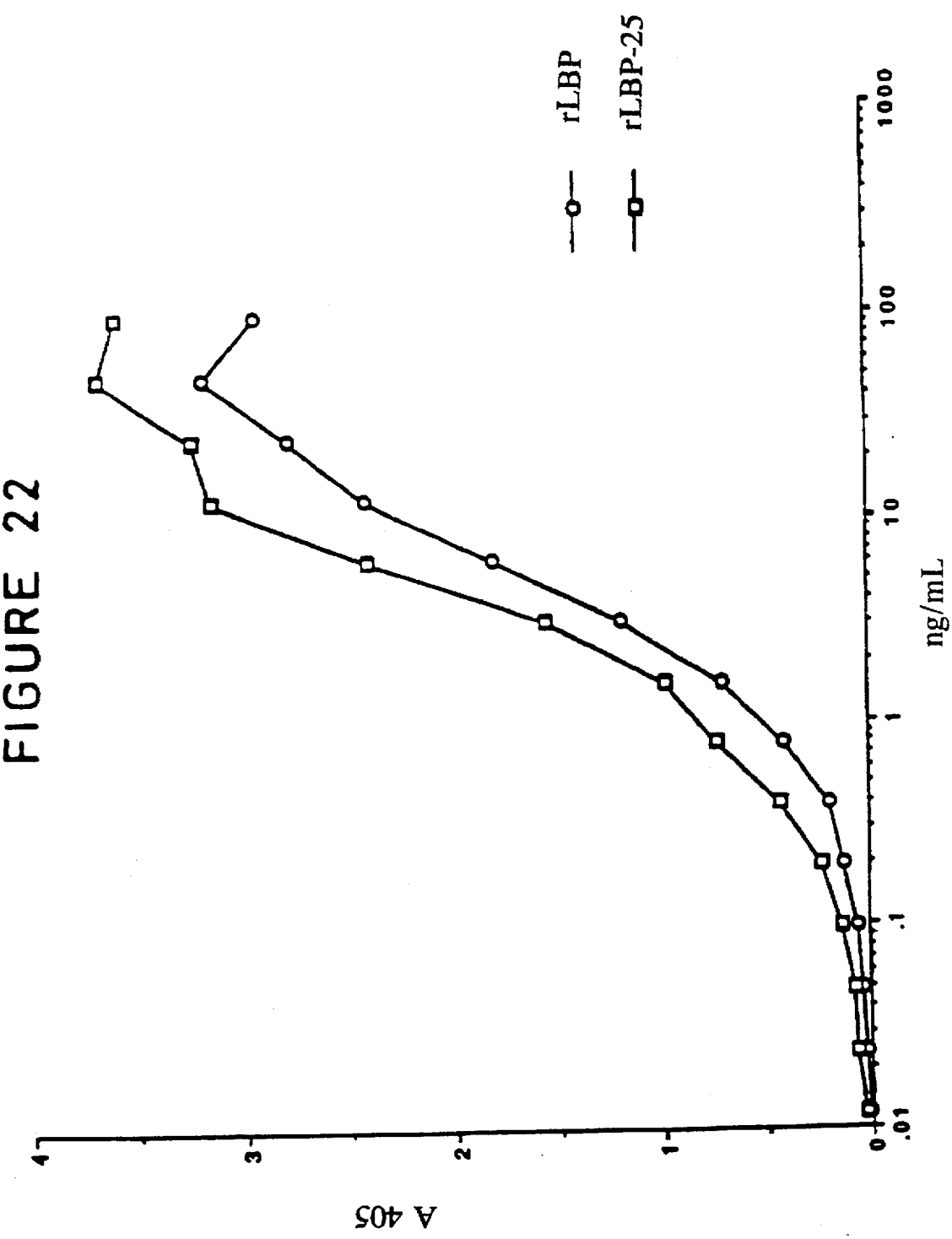
FIG. 22 depicts the binding of rLBP and rLBP$_{25}$ in an LBP sandwich ELISA assay.

An LBP sandwich ELISA has been developed which utilizes a rabbit anti-rLBP antibody on solid-phase with a biotin-labeled rabbit anti-rLBP as the detector. Both rLBP and rLBP$_{25}$ were detected by this ELISA (FIG. 22). The linear range of the rLBP standard curve was 40 to 800 pg/mL.

In this assay, rBPI produced a signal which was approximately 5 orders of magnitude lower than that of rLBP. For example, the signal produced by 100,000 ng/mL of rBPI was equivalent to the signal produced by 0.7 ng/mL of rLBP. Therefore, endogenous BPI will have a negligible effect on the accurate measurement of LBP.

Fifty microliters of affinity purified rabbit anti-rLBP antibody (1 µg/mL in PBS) were incubated overnight at 2–8° C. (or alternatively, 1 hour at 37° C.) in the wells of Immulon 2 (Dynatech Laboratories Inc., Chantilly, Va.) microliter plates. The antibody solution was removed and 200 µL of 1% non-fat milk in PBS (blocking agent) was added to all wells. After blocking the plates for one hour at room temperature, the wells were washed three times with 300 µL of wash buffer (PBS/0.05% Tween-20). Standards, samples and controls were diluted in triplicate with PBS containing 1% bovine serum albumin, 0.05% Tween 20 (PBS-BSA/Tween) and 10 units/mL of sodium heparin (Sigma Chemical Co., St. Louis, Mo.) in separate 96-well plates. rLBP or rLBP$_{25}$ standard solutions were prepared as serial two-fold dilutions from 100 to 0.012 ng/mL. Each replicate and dilution of the standards, samples and controls (50 µL) was transferred to the blocked microtiten plates and incubated for one hour at 37° C. After the primary incubation, the wells were washed three times with wash buffer. Biotin-labeled rabbit anti-rLBP antibody was diluted 1/4000 in PBS-BSA/ Tween and 50 µL was added to all wells. The plates were then incubated for one hour at 37° C. Subsequently, all wells were washed 3 times with wash buffer. Alkaline phosphatase-labeled streptavidin (Zymed Laboratories Inc., San Francisco, Calif.) was diluted 1/2000 in PBS-BSA/ Tween and 50 µL was added to all wells. After incubation for 15 minutes at 37° C., all wells were washed three times with wash buffer and 3 times with deionized water and the substrate p-nitrophenylphosphate (1 mg/mL in 10% dietha- nolamine buffer) was added in a volume of 50 to all wells. Color development was allowed to proceed for one hour at room temperature, after which 50 µL of 1 N NaOH was added to stop the reaction. The absorbance at 405 nm was determined for all wells using a Vmax Plate Reader (Molecular Devices Corp., Menlo Park, Calif.).

The mean absorbance at 405 nm ($A_{405}$) for all samples and standards (in triplicate) were corrected for background by subtracting the mean $A_{405}$ of wells receiving only sample dilute buffer (no BPI) in the primary incubation step. A standard curve was then plotted as $A_{405}$ versus ng/ml of rLBP or $rLBP_{25}$. The linear range was selected, a linear regression analysis was performed and concentrations were determined for samples and controls by interpolation from the standard curve.

EXAMPLE 18

Construction of Vectors for Expression of LBP Derivatives

An LBP derivative was constructed in which the alanine residue at position 131 was mutated to cysteine. This position is analogous to cysteine 132 in the BPI sequence, which appears to be the cysteine involved in homodimer formation. By placing a cysteine in the same position in the LBP sequence, the expressed protein may also have the ability to dimerize via interchain disulfide bond formation through cysteine 131, and the resultant dimer may have increased biological potency as is observed for the BPI dimer. To construct the LBP (1–197) (Cys131) derivative, two complementary oligonucleotides containing the desired mutation were used to replace a portion of the LBP sequence between BpmI and PstI restriction sites, corresponding to the amino acid sequence from residue 127 to residue 133. These oligonucleotides were LBP15: 5'-CCCACAGTCACGTGCTCCAGCTGCA-3'[SEQ ID NO:15], and LBP16:5'-GCTGGAGCACGTGACTGTGGGCC-3'[SEQ ID NO:16]. These 2 annealed oligonucleotides were ligated to two fragments from pML116: the -409 bp HindIII-BpmI fragment and the -3033 bp PstI-HindIII fragment, to generate plasmid pML136. Plasmid pML116 is a vector for use in an in vitro transcription/translation system encoding LBP (1–197) which corresponds to mammalian vectors pING4505 and pING4508 described above. Plasmid pML136 is then expressed in an in vitro transcription/ translation system as described above to produce LBP (1–197) (Cys 131). A corresponding vector for expression in mammalian cells can be constructed according to the methods described previously.

EXAMPLE 19

Vectors for Expression of LBP-IgG Hybrid Fusion Proteins

Portions of the LBP protein can be included in fusions with the Fc region of human $IgG_1$ according to the general methods of co-owned and copending U.S. patent application Ser. No. 08/064,693 filed May 19, 1993, the disclosure of which is hereby incorporated by reference, which teaches the construction of BPI-IgG fusion proteins. These LBP hybrid proteins may include truncated forms of LBP, such as 1–197, and may also include LBP derivatives containing the alanine 131 to cysteine mutation. These LBP hybrid proteins may be expected to form dimers upon recombinant production and may also have improved pharmacokinetics.

EXAMPLE 20

In Vitro Transcription/Translations of Truncated LBP Fragments and Determination of Their Ability to Mediate LPS Stimulation of TNF Activity While $rLBP_{25}$ and rLBP interact similarly with lipid A/LPS, rLBP and not $rLBP_{25}$ can stimulate the uptake of LPS and release the TNF by THP-1 cells. These data suggest that the region of LBP responsible for mediation of LPS activity via the CD14 receptor lies between positions 197 and 456 (the end) of the LBP protein sequence. To define this region more precisely, plasmid pML130 containing the entire 456 amino acid sequence of LBP (including silent mutations to introduce a ClaI restriction site at position 197–198), was constructed for in vitro transcription/ translation experiments. Plasmid pML130 corresponds generally to mammalian vector pING4539 described previously. The LBP insert in pML130 is under the control of the T7 RNA polymerase promoter, which efficiently transcribes RNA from linear DNA templates. Therefore, deletions of the LBP sequence generated via restriction digests of plasmid pMLI130 in the region between residues 197 and 456 as set out in Table 5 below are used as templates in the in vitro transcription/translation reaction to generate truncated LBP protein fragments. The biological activity of these LBP protein fragments are then tested to determine the region of the LBP sequence necessary for mediating the interaction of LPS with the CD14 receptor with the LBP (1–456) holoprotein acting as a positive control for CD14 activity and the $rLBP_{25}$ (1–197) fragment acting as a negative control. Mammalian vectors for expression of the LBP derivatives are produced and the derivatives are expressed according to the methods disclosed previously.

TABLE 5

| Restriction enzyme digest | LBP fragment size (amino acids) |
|---|---|
| HindIII | 456 |
| Eco47III | 400 |
| BsiHKAI | 342 |
| Bam1105I | 298 |
| Bsu36I | 244 |
| ClaI | 196 |

EXAMPLE 21

Construction of Vectors for Expression of LBP Hybrid Proteins

A number of vectors were constructed to express LBP hybrid proteins containing both BPI and LBP sequences derived from the amino-terminal domains of each protein. Such proteins are expected to retain LPS binding activity since the LPS binding domain exists within the amino-terminal region of both BPI and LBP. It is further expected that the hybrid proteins comprising amino terminal portions of both LBP and BPI would be unable to mediate LPS effects via interaction with CD14 receptor. Such proteins may further have advantageous biologic or pharmacokinetic properties. Vectors constructed as intermediates or for use in the in vitro transcription/translation system have the designation "pIC" or "pML" followed by a number while vectors intended for expression in mammalian cells have the designation "pING" followed by a number.

A vector encoding an LBP hybrid protein combining the elements of pML105 [LBP (1–43)/BPI (44–199)] and pML103 [BPI (1–159)/LBP (158–197)], namely pML134, was constructed to encode LBP (1–43)/BPI (44–159)/LBP (158–197). The construction of pML134 was accomplished by ligating the −458 bp NheI-EcoRI fragment of pML105 to the −3011 bp EcoRI-NheI fragment of pML103. In addition to pING4526 already described, another vector for expression of BPI(1–159)/LBP(158–197) in mammalian cells was constructed which contained optimized elements including Kozak initiation sequence, human kappa poly A/Mouse Kappa genomic transcription termination and CMV promoter as described in coowned and co-pending U.S. application Ser. No. 08/013,801, U.S. Pat. No. 5,420,019, filed Feb. 2, 1993 the disclosure of which is hereby incorporated by reference. The mammalian vector was designated pING4168.

Two other BPI/LBP hybrids, pML117 and pML118, were constructed by taking advantage of common PstI restriction sites contained in the coding region sequence of both proteins. The starting plasmids for these constructs were pIC127, which contains an insert encoding BPI (1–199), and pIC106, which contains an insert encoding LBP (1–197). pML117, containing an insert encoding BPI (1–137)/LBP (137–197), was constructed by replacing the −200 bp PstI-XhoI fragment of BPI in pIC127 with the corresponding LBP fragment from pIC106. pML118, encoding BPI (1–25) LBP (26–135) BPI (137–199) was constructed by replacing an −600 bp PstI-PstI fragment within the BPI coding region of pIC127 with the corresponding LBP fragment from pIC106. The resulting plasmids are used as templates in the in vitro transcription/translation reaction method according to Example 7 in order to generate LBP hybrid proteins. Constructs pML103, pML105, pML116, pML117, pML118, pML134 were expressed in the transcription/translation system and the products were all detected by ELISA using appropriate reagents. All the products bound well to Lipid A with the exception of BPI (1–25)/LBP(26–134)/BPI (135–199) which bound poorly. Three products exhibited superior Lipid A binding activity. They were BPI(1–159)/LBP(158–197), BPI(1–135)/LBP(135–197), and LBP (1–43)/BPI(44–159)/LBP(158–197).

Mammalian vectors for expression of the LBP hybrid proteins are produced and the derivatives are expressed according to the methods disclosed previously.

EXAMPLE 22

Construction of Vectors for Expression of LBP Hybrid Proteins Comprising BPI/LBP Active Domain Replacement Mutants rBPI$_{23}$ possesses three biological activities, LPS binding, heparin binding and bactericidal activity, which have been localized to specific domains of the protein defined by synthetic peptides as disclosed by co-owned and copending U.S. patent application Ser. No. 08/209,762 filed Mar. 11, 1994 which is a continuation-in-part of U.S. patent application Ser. No. 08/183,222, abandoned, filed Jan. 14, 1994, which is a continuation-in-part of U.S patent application Ser. No. 08/093,202, abandoned, filed Jul. 15, 1993 which is a continuation-in-part of U.S. patent application Ser. No. 08/030,644, U.S. Pat. No: 5,348,942 filed Mar. 12, 1993 the disclosures of which are incorporated herein by reference. Domain I of BPI includes the amino acid sequence of human BPI from about position 17 to about position 45 having the sequence: BPI Domain I ASQQGTAALQKELKRIKPDYS-DSFKIKH (SEQ ID NO: 17); Domain II of BPI includes the amino acid sequence of human BPI from about position 65 to about position 99 having the sequence BPI Domain II SSQISMVPNVGLKFSISNANIKISGKWKAQKRFLK (SEQ ID NO:18) while Domain III of BPI includes the amino acid sequence of human BPI from about position 142 to about position 169 having the sequence BPI Domain III VHVHISKSKVGWLIQLFHKKIESALRNK (SEQ ID NO:19) The corresponding domain I of LBP includes the amino acid sequence of human LBP from about position 17 to about position 45 having the sequence LBP Domain I AAQEGLLALQSELLRITLPDFTGDLRIPH (SEQ IS NO:20); Domain II of LBP includes the amino acid sequence of human LBP from about position 65 to about position 99 having the sequence LBP Domain II HSALR-PVPGQGLSLSISDSSIRVQGRWKVRKSFFK (SEQ ID NO:21); while Domain III of LBP includes the amino acid sequence of human LBP from about position 141 to about position 167 having the sequence LBP Domain III VEVDMSGDLGWLLNLFHNQIESKFQKV (SEQ ID NO 22).

Several plasmids encoding LBP hybrid proteins were constructed for in vitro transcription/translation studies in which sequences selected from Domains II and/or III of BPI were inserted to replace the corresponding region of LBP$_{25}$. Conversely, other plasmids were constructed in which sequences selected from Domains II and/or III of LBP were inserted to replace sequences from the corresponding region of BPI$_{23}$.

First, plasmid pML131 was constructed comprising silent mutations in Domain II of BPI$_{23}$. Specifically, the nucleotide sequence between ARLII and BsrBI restriction sites in the BPI$_{23}$ coding region of pIC127 was replaced with the annealed oligonucleotides BPI-66: 5'-TTAAATTTTCGATATCCAACGCCAATATTAAGAT-CTCCGGAAAATGGAAGGCACAAAAGCGCTTCCTT-AAGATGAG-3' (SEQ ID NO:23) and BPI-67:5'-CTCATCTTAAGGAAGCGCTTTTGTGCCT-TCCATTTTCCGGAGATCTTA ATATTGGCGTTG-GATATCGAAAAT (SEQ ID NO:24). This replacement changed the nucleotide sequence but not the amino acid sequence in the region between residues 77 and 100, and introduced additional restriction sites which could be used for site-directed mutagenesis (EcoRV, SspI, BglII, BspEI, Eco47III, and relocated AflII).

In addition plasmid pML140 was constructed comprising silent mutations in Domain III of BPI$_{23}$. Specifically, the nucleotide sequence between PmlI and BstBI restriction sites in the BPI$_{23}$ coding region of pIC127 was replaced with the annealed oligonucleotides BPI-78:5'-GTGCACATTTCGAAGAGCAAAGTGGGGTGGCTGA-TCCAATTGTTCCACAAAAAAATTGAGAGCGCGC-TG-3' (SEQ ID NO:25) and BPI-79: 5'-CGCAGCGCGCTCTCAATTTTTTTGTGGAACAA-TTGGATCAGCCACCCCACTTTGCTCTTCGAAATGT-GCAC-3' (SEQ ID NO:26). This replacement changed the nucleotide sequence but not the amino acid sequence in the region between residues 146 and 163, and introduced additional restriction sites which could be used for site-directed mutagenesis (relocated BstBI, MunI, and BssHII).

A plasmid for in vitro transcription/translation studies encoding the LBP hybrid protein [LBP(1–87)/BPI(88–100)/LBP(101–197)] was constructed in which a portion of Domain II of BPI replaced the corresponding LBP sequence. The hybrid protein comprised the first 87 amino acid residues of LBP, amino acid residues 88–100 of BPI and amino acid residues 101–197 of LBP. The nucleotide sequence between AvaII and BanII restriction sites in the LBP$_{25}$ coding region of pML116 was replaced with the annealed oligonucleotides BPI-74: 5'-GTCAGCGGGAAATGGAAGGCACAAAAGAGATTTTAAAAATGCAGGGCT-3' (SEQ ID NO:27) and BPI-75: 5'-CTGCATTTTTAAAAATCTCTTTTGTGCCTTCCATTTCCCGCT-3' (SEQ ID NO:28). This replacement essentially changed the amino acid sequence of residues 88–100 of LBP$_{25}$ from QGRWKVRKSFFKL (SEQ ID NO:29) to SGKWKAQKRFLKM (SEQ ID NO:30). The resulting plasmid was designated pML135.

A plasmid for in vitro transcription/translation studies encoding the LBP hybrid protein [LBP(1–146)/BPI(148–161)/LBP(160–197)] was constructed in which a portion of Domain III of BPI replaced the corresponding LBP sequence. The hybrid protein comprised the first 146 amino acid residues of LBP, amino acid residues 148–161 of BPI and amino acid residues 160–197 of LBP. Specifically, the nucleotide sequence between AflIII and ScaI restriction sites in the LBP$_{25}$ coding region of pML116 was replaced with the annealed oligonucleotides BPI-76:5'-CATGTCGAAGAGCAAAGTGGGGTGGCTGATCCAACTCTTCCACAAAAAAATTGAGTCCAAATTTCAGAAAGT-' (SEQ ID NO:31) and BPI-77:5'-ACTTTCTGAAATTTGGACTCAATTTTTTTGTGGAAGAGTTGGATCAGCCACCCCACTTTGCTCTTCGA-3' (SEQ ID NO:32). This replacement essentially changed the amino acid sequence of residues 147–159 of LBP$_{25}$ from GDLGWLLNLFHNQ (SEQ ID NO:33) to the corresponding BPI sequence KSKVGWLIQLFHKK (SEQ ID NO:34). This plasmid was designated pML137.

A plasmid for in vitro transcription/translation studies encoding the LBP hybrid protein [LBP(1–87)/BPI(88–100)/LBP(101–146)/BPI(148–161)/LBP(160–197)] was constructed in which portions of Domains II and III of BPI replaced the corresponding LBP sequences. The hybrid protein comprised the first 87 amino acid residues of LBP, amino acid residues 88–100 of BPI, amino acid residues 101–146 of LBP, amino acid residues 148–161 of BPI and amino acid residues 160–197 of LBP. Plasmid pML138 was constructed from pML135 and pML137 by replacing an ~292 bp BanII-XhoI fragment of the coding region of pML135 with the corresponding fragment from pML137 to introduce the domain III mutations into the plasmid already containing the domain II mutations.

A plasmid for in vitro transcription/translation studies encoding the LBP hybrid protein [BPI(1–85)/LBP(86–99)/BPI(100–199)] was constructed in which a portion of Domain II of LBP replaced the corresponding BPI sequence. The hybrid protein comprised the first 85 amino acid residues of BPI, amino acid residues 86–99 of LBP and amino acid residues 100–199 of BPI. Specifically, the nucleotide sequence between SspI and AflII restriction sites in the BPI$_{23}$ coding region of pML$_{131}$ was replaced with the annealed oligonucleotides BPI-80: 5'-ATTCGTGTACAGGGCAGGTGGAAGGTGCGCAAGTCATTCT-3' (SEQ ID NO:35) and BPI-81: 5'-TTAAAGAATGACTTGCGCACCTTCCACCTGCCCTGTACACGAAT-3' (SEQ ID NO:36). This replacement essentially changed the amino acid sequence of residues 86–99 of BPI$_{23}$ from KISGKWKAQKRFLK (SEQ ID NO:37) to the corresponding LBP sequence RVQGRWKVRKSFFK. This plasmid was designated pML141 (SEQ ID NO:38).

A plasmid for in vitro transcription/translation studies encoding the LBP hybrid protein [BPI(1–147/LBP(147–159)/BPI(162–199)] was constructed in which a portion of Domain III of LBP replaced the corresponding BPI sequence. The hybrid protein comprised the first 147 amino acid residues of BPI, amino acid residues 147–159 of LBP and amino acid residues 162–199 of BPI. The nucleotide sequence between BstBI and BssHII restriction sites in the BPI$_{23}$ coding region of pML140 was replaced with the annealed oligonucleotides BPI-82: 5'-CGGGAGACTTGGGGTGGCTGTTGAACCTCTTCCACAACCAGATTGAGAG-3' (SEQ ID NO:39) and BPI-83: 5'-CGCGCTCTCAATCTGGTTGTGGAAGAGGTTCAACAGCCACCCCAAGTCTCC-3' (SEQ ID NO:40). This replacement essentially changed the amino acid sequence of residues 148–161 of BPI$_{23}$ from KSKVGWLIQLFHKK (SEQ ID NO:41) to the corresponding LBP sequence GDLGWLLNLFHNQ (SEQ ID NO:42). This plasmid was designated pML142.

A plasmid for in vitro transcription/translation studies encoding the LBP hybrid protein [BPI(1–85)/LBP(86–99)/BPI(100–147)/LBP(147–159)/BPI(162–199)] was constructed in which portions of Domains II and III of LBP replaced the corresponding BPI sequences. The hybrid protein comprised the first 85 amino acid residues of BPI, amino acid residues 86–99 of LBP, amino acid residues 100–147 of BPI, amino acid residues 147–159 of LBP and amino acid residues 162–199 of BPI. pML143 can be constructed frown pML141 and pML142 by replacing an ~175 bp PmlI-XhoI fragment in the coding region of pML141 with the corresponding fragment from pML142 to introduce the domain III mutations into the plasmid already containing the domain II mutations. This plasmid was designated pML143.

The resulting plasmids are used as templates in the in vitro transcription/translation reaction to generate LBP hybrid proteins. Mammalian vectors for expression of the LBP hybrid proteins are produced and the derivatives are expressed according to the methods disclosed previously. The biological activities of these LBP hybrid proteins are then tested according to the methods set out above.

EXAMPLE 23

LBP derivatives in the form of synthetic LBP peptides were prepared according to the methods of Merrifield, J. Am, Chem, Soc. 85: 2149 (1963) and Merrifield, Anal Chem. 38: 1905–1914 (1966) using an Applied Biosystems, Inc. Model 432 synthesizer. The resulting derivatives comprised portions of the LBP sequence corresponding to either of BPI Domain II or III. The LBP derivative designated LBP-1 consisted of residues 73 through 99 of LBP having the sequence GQGLSLSISDSSIRVQGRWKVRKSFFK (SEQ ID NO:43). The LBP derivative designated LBP-2 consisted of residues 140 through 161 of LBP and had the sequence DVEVDMSGDSGWLLNLFHNQIE (SEQ ID NO:44). The LBP derivatives were subjected to an Limulus Amoebocyte Lysate (LAL) assay using a quantiative chromogenic LAL kit (Whitaker Bioproducts, Inc., Walkersville, Md.) to determine neutralization of LPS. LBP-1 was found to neutralize endotoxin in the LAL assay while LBP-2 did not.

Numerous modifications and variations in the practice of the invention are expected to occur to those skilled in the art upon consideration of the foregoing description of the presently preferred embodiments thereof. Consequently, the only limitations which should be placed upon the scope of the present invention are those which appear in the appended claims.

---

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
( A ) LENGTH: 591 base pairs
( B ) TYPE: nucleic acid
( C ) STRANDEDNESS: single
( D ) TOPOLOGY: linear ( i i ) MOLECULE TYPE: DNA ( i x ) FEATURE:
( A ) NAME/KEY: CDS
( B ) LOCATION: 1..591

( i x ) FEATURE:
( A ) NAME/KEY: misc_feature
( D ) OTHER INFORMATION: "rLBP25"

( x i ) SEQUENCE DESCRIPTION: SEQ ID NO:1:

| GCC | AAC | CCC | GGC | TTG | GTC | GCC | AGG | ATC | ACC | GAC | AAG | GGA | CTG | CAG | TAT | 48 |
| Ala | Asn | Pro | Gly | Leu | Val | Ala | Arg | Ile | Thr | Asp | Lys | Gly | Leu | Gln | Tyr | |
| 1 | | | | 5 | | | | | 10 | | | | | 15 | | |

| GCG | GCC | CAG | GAG | GGG | CTA | TTG | GCT | CTG | CAG | AGT | GAG | CTG | CTC | AGG | ATC | 96 |
| Ala | Ala | Gln | Glu | Gly | Leu | Leu | Ala | Leu | Gln | Ser | Glu | Leu | Leu | Arg | Ile | |
| | | | 20 | | | | | 25 | | | | | 30 | | | |

| ACG | CTG | CCT | GAC | TTC | ACC | GGG | GAC | TTG | AGG | ATC | CCC | CAC | GTC | GGC | CGT | 144 |
| Thr | Leu | Pro | Asp | Phe | Thr | Gly | Asp | Leu | Arg | Ile | Pro | His | Val | Gly | Arg | |
| | | 35 | | | | | 40 | | | | | 45 | | | | |

| GGG | CGC | TAT | GAG | TTC | CAC | AGC | CTG | AAC | ATC | CAC | AGC | TGT | GAG | CTG | CTT | 192 |
| Gly | Arg | Tyr | Glu | Phe | His | Ser | Leu | Asn | Ile | His | Ser | Cys | Glu | Leu | Leu | |
| | 50 | | | | | 55 | | | | | 60 | | | | | |

| CAC | TCT | GCG | CTG | AGG | CCT | GTC | CCT | GGC | CAG | GGC | CTG | AGT | CTC | AGC | ATC | 240 |
| His | Ser | Ala | Leu | Arg | Pro | Val | Pro | Gly | Gln | Gly | Leu | Ser | Leu | Ser | Ile | |
| 65 | | | | | 70 | | | | | 75 | | | | | 80 | |

| TCC | GAC | TCC | TCC | ATC | CGG | GTC | CAG | GGC | AGG | TGG | AAG | GTG | CGC | AAG | TCA | 288 |
| Ser | Asp | Ser | Ser | Ile | Arg | Val | Gln | Gly | Arg | Trp | Lys | Val | Arg | Lys | Ser | |
| | | | | 85 | | | | | 90 | | | | | 95 | | |

| TTC | TTC | AAA | CTA | CAG | GGC | TCC | TTT | GAT | GTC | AGT | GTC | AAG | GGC | ATC | AGC | 336 |
| Phe | Phe | Lys | Leu | Gln | Gly | Ser | Phe | Asp | Val | Ser | Val | Lys | Gly | Ile | Ser | |
| | | | 100 | | | | | 105 | | | | | 110 | | | |

| ATT | TCG | GTC | AAC | CTC | CTG | TTG | GGC | AGC | GAG | TCC | TCC | GGG | AGG | CCC | ACA | 384 |
| Ile | Ser | Val | Asn | Leu | Leu | Leu | Gly | Ser | Glu | Ser | Ser | Gly | Arg | Pro | Thr | |
| | | 115 | | | | | 120 | | | | | 125 | | | | |

| GTT | ACT | GCC | TCC | AGC | TGC | AGC | AGT | GAC | ATC | GCT | GAC | GTG | GAG | GTG | GAC | 432 |
| Val | Thr | Ala | Ser | Ser | Cys | Ser | Ser | Asp | Ile | Ala | Asp | Val | Glu | Val | Asp | |
| | 130 | | | | | 135 | | | | | 140 | | | | | |

| ATG | TCG | GGA | GAC | TTG | GGG | TGG | CTG | TTG | AAC | CTC | TTC | CAC | AAC | CAG | ATT | 480 |
| Met | Ser | Gly | Asp | Leu | Gly | Trp | Leu | Leu | Asn | Leu | Phe | His | Asn | Gln | Ile | |
| 145 | | | | 150 | | | | | 155 | | | | | 160 | | |

| GAG | TCC | AAG | TTC | CAG | AAA | GTA | CTG | GAG | AGC | AGG | ATT | TGC | GAA | ATG | ATC | 528 |
| Glu | Ser | Lys | Phe | Gln | Lys | Val | Leu | Glu | Ser | Arg | Ile | Cys | Glu | Met | Ile | |
| | | | 165 | | | | | 170 | | | | | 175 | | | |

| CAG | AAA | TCG | GTG | TCC | TCC | GAT | CTA | CAG | CCT | TAT | CTC | CAA | ACT | CTG | CCA | 576 |
| Gln | Lys | Ser | Val | Ser | Ser | Asp | Leu | Gln | Pro | Tyr | Leu | Gln | Thr | Leu | Pro | |
| | | | 180 | | | | | 185 | | | | | 190 | | | |

```
GTT  ACA  ACA  GAG  ATT                                                    591
Val  Thr  Thr  Glu  Ile
          195
```

( 2 ) INFORMATION FOR SEQ ID NO:2:

( i ) SEQUENCE CHARACTERISTICS:
        ( A ) LENGTH: 197 amino acids
        ( B ) TYPE: amino acid
        ( D ) TOPOLOGY: linear ( i i ) MOLECULE TYPE: protein ( i x ) FEATURE:
        ( A ) NAME/KEY: misc_feature
        ( D ) OTHER INFORMATION: "rLBP25"

( x i ) SEQUENCE DESCRIPTION: SEQ ID NO:2:

```
Ala  Asn  Pro  Gly  Leu  Val  Ala  Arg  Ile  Thr  Asp  Lys  Gly  Leu  Gln  Tyr
 1              5                        10                       15
Ala  Ala  Gln  Glu  Gly  Leu  Leu  Ala  Leu  Gln  Ser  Glu  Leu  Leu  Arg  Ile
              20                       25                  30
Thr  Leu  Pro  Asp  Phe  Thr  Gly  Asp  Leu  Arg  Ile  Pro  His  Val  Gly  Arg
              35                       40                  45
Gly  Arg  Tyr  Glu  Phe  His  Ser  Leu  Asn  Ile  His  Ser  Cys  Glu  Leu  Leu
         50                       55                  60
His  Ser  Ala  Leu  Arg  Pro  Val  Pro  Gly  Gln  Gly  Leu  Ser  Leu  Ser  Ile
 65                       70                  75                       80
Ser  Asp  Ser  Ser  Ile  Arg  Val  Gln  Gly  Arg  Trp  Lys  Val  Arg  Lys  Ser
                   85                       90                  95
Phe  Phe  Lys  Leu  Gln  Gly  Ser  Phe  Asp  Val  Ser  Val  Lys  Gly  Ile  Ser
             100                      105                 110
Ile  Ser  Val  Asn  Leu  Leu  Leu  Gly  Ser  Glu  Ser  Ser  Gly  Arg  Pro  Thr
             115                      120                 125
Val  Thr  Ala  Ser  Ser  Cys  Ser  Ser  Asp  Ile  Ala  Asp  Val  Glu  Val  Asp
        130                      135                 140
Met  Ser  Gly  Asp  Leu  Gly  Trp  Leu  Leu  Asn  Leu  Phe  His  Asn  Gln  Ile
145                      150                      155                      160
Glu  Ser  Lys  Phe  Gln  Lys  Val  Leu  Glu  Ser  Arg  Ile  Cys  Glu  Met  Ile
             165                      170                 175
Gln  Lys  Ser  Val  Ser  Ser  Asp  Leu  Gln  Pro  Tyr  Leu  Gln  Thr  Leu  Pro
             180                      185                 190
Val  Thr  Thr  Glu  Ile
          195
```

( 2 ) INFORMATION FOR SEQ ID NO:3:

( i ) SEQUENCE CHARACTERISTICS:
        ( A ) LENGTH: 1443 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS
        ( B ) LOCATION: 1..1443

( i x ) FEATURE:
        ( A ) NAME/KEY: mat_peptide
        ( B ) LOCATION: 76..1443

( i x ) FEATURE:

( A ) NAME/KEY: misc_feature
( D ) OTHER INFORMATION: "rLBP"

( x i ) SEQUENCE DESCRIPTION: SEQ ID NO:3:

| ATG | GGG | GCC | TTG | GCC | AGA | GCC | CTG | CCG | TCC | ATA | CTG | CTG | GCA | TTG | CTG | 48 |
| Met | Gly | Ala | Leu | Ala | Arg | Ala | Leu | Pro | Ser | Ile | Leu | Leu | Ala | Leu | Leu | |
| -25 | | | | -20 | | | | | -15 | | | | | | -10 | |

| CTT | ACG | TCC | ACC | CCA | GAG | GCT | CTG | GGT | GCC | AAC | CCC | GGC | TTG | GTC | GCC | 96 |
| Leu | Thr | Ser | Thr | Pro | Glu | Ala | Leu | Gly | Ala | Asn | Pro | Gly | Leu | Val | Ala | |
| | | | | -5 | | | | | 1 | | | | 5 | | | |

| AGG | ATC | ACC | GAC | AAG | GGA | CTG | CAG | TAT | GCG | GCC | CAG | GAG | GGG | CTA | TTG | 144 |
| Arg | Ile | Thr | Asp | Lys | Gly | Leu | Gln | Tyr | Ala | Ala | Gln | Glu | Gly | Leu | Leu | |
| | | 10 | | | | | 15 | | | | | 20 | | | | |

| GCT | CTG | CAG | AGT | GAG | CTG | CTC | AGG | ATC | ACG | CTG | CCT | GAC | TTC | ACC | GGG | 192 |
| Ala | Leu | Gln | Ser | Glu | Leu | Leu | Arg | Ile | Thr | Leu | Pro | Asp | Phe | Thr | Gly | |
| | 25 | | | | | 30 | | | | | | 35 | | | | |

| GAC | TTG | AGG | ATC | CCC | CAC | GTC | GGC | CGT | GGG | CGC | TAT | GAG | TTC | CAC | AGC | 240 |
| Asp | Leu | Arg | Ile | Pro | His | Val | Gly | Arg | Gly | Arg | Tyr | Glu | Phe | His | Ser | |
| 40 | | | | | 45 | | | | | 50 | | | | | 55 | |

| CTG | AAC | ATC | CAC | AGC | TGT | GAG | CTG | CTT | CAC | TCT | GCG | CTG | AGG | CCT | GTC | 288 |
| Leu | Asn | Ile | His | Ser | Cys | Glu | Leu | Leu | His | Ser | Ala | Leu | Arg | Pro | Val | |
| | | | | 60 | | | | | 65 | | | | | 70 | | |

| CCT | GGC | CAG | GGC | CTG | AGT | CTC | AGC | ATC | TCC | GAC | TCC | TCC | ATC | CGG | GTC | 336 |
| Pro | Gly | Gln | Gly | Leu | Ser | Leu | Ser | Ile | Ser | Asp | Ser | Ser | Ile | Arg | Val | |
| | | | 75 | | | | | 80 | | | | | 85 | | | |

| CAG | GGC | AGG | TGG | AAG | GTG | CGC | AAG | TCA | TTC | TTC | AAA | CTA | CAG | GGC | TCC | 384 |
| Gln | Gly | Arg | Trp | Lys | Val | Arg | Lys | Ser | Phe | Phe | Lys | Leu | Gln | Gly | Ser | |
| | | 90 | | | | | 95 | | | | | 100 | | | | |

| TTT | GAT | GTC | AGT | GTC | AAG | GGC | ATC | AGC | ATT | TCG | GTC | AAC | CTC | CTG | TTG | 432 |
| Phe | Asp | Val | Ser | Val | Lys | Gly | Ile | Ser | Ile | Ser | Val | Asn | Leu | Leu | Leu | |
| | 105 | | | | | 110 | | | | | 115 | | | | | |

| GGC | AGC | GAG | TCC | TCC | GGG | AGG | CCC | ACA | GTT | ACT | GCC | TCC | AGC | TGC | AGC | 480 |
| Gly | Ser | Glu | Ser | Ser | Gly | Arg | Pro | Thr | Val | Thr | Ala | Ser | Ser | Cys | Ser | |
| 120 | | | | | 125 | | | | | 130 | | | | | 135 | |

| AGT | GAC | ATC | GCT | GAC | GTG | GAG | GTG | GAC | ATG | TCG | GGA | GAC | TTG | GGG | TGG | 528 |
| Ser | Asp | Ile | Ala | Asp | Val | Glu | Val | Asp | Met | Ser | Gly | Asp | Leu | Gly | Trp | |
| | | | | 140 | | | | | 145 | | | | | 150 | | |

| CTG | TTG | AAC | CTC | TTC | CAC | AAC | CAG | ATT | GAG | TCC | AAG | TTC | CAG | AAA | GTA | 576 |
| Leu | Leu | Asn | Leu | Phe | His | Asn | Gln | Ile | Glu | Ser | Lys | Phe | Gln | Lys | Val | |
| | | | 155 | | | | | 160 | | | | | 165 | | | |

| CTG | GAG | AGC | AGG | ATT | TGC | GAA | ATG | ATC | CAG | AAA | TCG | GTG | TCC | TCC | GAT | 624 |
| Leu | Glu | Ser | Arg | Ile | Cys | Glu | Met | Ile | Gln | Lys | Ser | Val | Ser | Ser | Asp | |
| | | 170 | | | | | 175 | | | | | 180 | | | | |

| CTA | CAG | CCT | TAT | CTC | CAA | ACT | CTG | CCA | GTT | ACA | ACA | GAG | ATT | GAC | AGT | 672 |
| Leu | Gln | Pro | Tyr | Leu | Gln | Thr | Leu | Pro | Val | Thr | Thr | Glu | Ile | Asp | Ser | |
| | 185 | | | | | 190 | | | | | 195 | | | | | |

| TTC | GCC | GAC | ATT | GAT | TAT | AGC | TTA | GTG | GAA | GCC | CCT | CGG | GCA | ACA | GCC | 720 |
| Phe | Ala | Asp | Ile | Asp | Tyr | Ser | Leu | Val | Glu | Ala | Pro | Arg | Ala | Thr | Ala | |
| 200 | | | | | 205 | | | | | 210 | | | | | 215 | |

| CAG | ATG | CTG | GAG | GTG | ATG | TTT | AAG | GGT | GAA | ATC | TTT | CAT | CGT | AAC | CAC | 768 |
| Gln | Met | Leu | Glu | Val | Met | Phe | Lys | Gly | Glu | Ile | Phe | His | Arg | Asn | His | |
| | | | | 220 | | | | | 225 | | | | | 230 | | |

| CGT | TCT | CCA | GTT | ACC | CTC | CTT | GCT | GCA | GTC | ATG | AGC | CTT | CCT | GAG | GAA | 816 |
| Arg | Ser | Pro | Val | Thr | Leu | Leu | Ala | Ala | Val | Met | Ser | Leu | Pro | Glu | Glu | |
| | | | 235 | | | | | 240 | | | | | 245 | | | |

| CAC | AAC | AAA | ATG | GTC | TAC | TTT | GCC | ATC | TCG | GAT | TAT | GTC | TTC | AAC | ACG | 864 |
| His | Asn | Lys | Met | Val | Tyr | Phe | Ala | Ile | Ser | Asp | Tyr | Val | Phe | Asn | Thr | |
| | | 250 | | | | | 255 | | | | | 260 | | | | |

| GCC | AGC | CTG | GTT | TAT | CAT | GAG | GAA | GGA | TAT | CTG | AAC | TTC | TCC | ATC | ACA | 912 |
| Ala | Ser | Leu | Val | Tyr | His | Glu | Glu | Gly | Tyr | Leu | Asn | Phe | Ser | Ile | Thr | |
| | 265 | | | | | 270 | | | | | 275 | | | | | |

| | | | | | | | | | | | | | | | | |
|---|---|---|---|---|---|---|---|---|---|---|---|---|---|---|---|---|
| GAT | GAG | ATG | ATA | CCG | CCT | GAC | TCT | AAT | ATC | CGA | CTG | ACC | ACC | AAG | TCC | 960 |
| Asp | Glu | Met | Ile | Pro | Pro | Asp | Ser | Asn | Ile | Arg | Leu | Thr | Thr | Lys | Ser | |
| 280 | | | | 285 | | | | | 290 | | | | | | 295 | |
| TTC | CGA | CCC | TTC | GTC | CCA | CGG | TTA | GCC | AGG | CTC | TAC | CCC | AAC | ATG | AAC | 1008 |
| Phe | Arg | Pro | Phe | Val | Pro | Arg | Leu | Ala | Arg | Leu | Tyr | Pro | Asn | Met | Asn | |
| | | | | 300 | | | | | 305 | | | | | 310 | | |
| CTG | GAA | CTC | CAG | GGA | TCA | GTG | CCC | TCT | GCT | CCG | CTC | CTG | AAC | TTC | AGC | 1056 |
| Leu | Glu | Leu | Gln | Gly | Ser | Val | Pro | Ser | Ala | Pro | Leu | Leu | Asn | Phe | Ser | |
| | | | 315 | | | | | 320 | | | | | | 325 | | |
| CCT | GGG | AAT | CTG | TCT | GTG | GAC | CCC | TAT | ATG | GAG | ATA | GAT | GCC | TTT | GTG | 1104 |
| Pro | Gly | Asn | Leu | Ser | Val | Asp | Pro | Tyr | Met | Glu | Ile | Asp | Ala | Phe | Val | |
| | | 330 | | | | | 335 | | | | | 340 | | | | |
| CTC | CTG | CCC | AGC | TCC | AGC | AAG | GAG | CCT | GTC | TTC | CGG | CTC | AGT | GTG | GCC | 1152 |
| Leu | Leu | Pro | Ser | Ser | Ser | Lys | Glu | Pro | Val | Phe | Arg | Leu | Ser | Val | Ala | |
| | 345 | | | | | 350 | | | | | 355 | | | | | |
| ACT | AAT | GTG | TCC | GCC | ACC | TTG | ACC | TTC | AAT | ACC | AGC | AAG | ATC | ACT | GGG | 1200 |
| Thr | Asn | Val | Ser | Ala | Thr | Leu | Thr | Phe | Asn | Thr | Ser | Lys | Ile | Thr | Gly | |
| 360 | | | | | 365 | | | | | 370 | | | | | 375 | |
| TTC | CTG | AAG | CCA | GGA | AAG | GTA | AAA | GTG | GAA | CTG | AAA | GAA | TCC | AAA | GTT | 1248 |
| Phe | Leu | Lys | Pro | Gly | Lys | Val | Lys | Val | Glu | Leu | Lys | Glu | Ser | Lys | Val | |
| | | | | 380 | | | | | 385 | | | | | 390 | | |
| GGA | CTA | TTC | AAT | GCA | GAG | CTG | TTG | GAA | GCG | CTC | CTC | AAC | TAT | TAC | ATC | 1296 |
| Gly | Leu | Phe | Asn | Ala | Glu | Leu | Leu | Glu | Ala | Leu | Leu | Asn | Tyr | Tyr | Ile | |
| | | | 395 | | | | | 400 | | | | | 405 | | | |
| CTT | AAC | ACC | TTC | TAC | CCC | AAG | TTC | AAT | GAT | AAG | TTG | GCC | GAA | GGC | TTC | 1344 |
| Leu | Asn | Thr | Phe | Tyr | Pro | Lys | Phe | Asn | Asp | Lys | Leu | Ala | Glu | Gly | Phe | |
| | | 410 | | | | | 415 | | | | | 420 | | | | |
| CCC | CTT | CCT | CTG | CTG | AAG | CGT | GTT | CAG | CTC | TAC | GAC | CTT | GGG | CTG | CAG | 1392 |
| Pro | Leu | Pro | Leu | Leu | Lys | Arg | Val | Gln | Leu | Tyr | Asp | Leu | Gly | Leu | Gln | |
| | 425 | | | | | 430 | | | | | 435 | | | | | |
| ATC | CAT | AAG | GAC | TTC | CTG | TTC | TTG | GGT | GCC | AAT | GTC | CAA | TAC | ATG | AGA | 1440 |
| Ile | His | Lys | Asp | Phe | Leu | Phe | Leu | Gly | Ala | Asn | Val | Gln | Tyr | Met | Arg | |
| 440 | | | | | 445 | | | | | 450 | | | | | 455 | |
| GTT | | | | | | | | | | | | | | | | 1443 |
| Val | | | | | | | | | | | | | | | | |

( 2 ) INFORMATION FOR SEQ ID NO:4:

( i ) SEQUENCE CHARACTERISTICS:
        ( A ) LENGTH: 481 amino acids
        ( B ) TYPE: amino acid
        ( D ) TOPOLOGY: linear ( i i ) MOLECULE TYPE: protein ( i x ) FEATURE:
        ( A ) NAME/KEY: misc_feature
        ( D ) OTHER INFORMATION: "rLBP"

( x i ) SEQUENCE DESCRIPTION: SEQ ID NO:4:

| | | | | | | | | | | | | | | |
|---|---|---|---|---|---|---|---|---|---|---|---|---|---|---|
| Met | Gly | Ala | Leu | Ala | Arg | Ala | Leu | Pro | Ser | Ile | Leu | Leu | Ala | Leu | Leu |
| -25 | | | | | -20 | | | | | -15 | | | | | -10 |
| Leu | Thr | Ser | Thr | Pro | Glu | Ala | Leu | Gly | Ala | Asn | Pro | Gly | Leu | Val | Ala |
| | | | | -5 | | | | | 1 | | | | 5 | | |
| Arg | Ile | Thr | Asp | Lys | Gly | Leu | Gln | Tyr | Ala | Ala | Gln | Glu | Gly | Leu | Leu |
| | | 10 | | | | | 15 | | | | | 20 | | | |
| Ala | Leu | Gln | Ser | Glu | Leu | Leu | Arg | Ile | Thr | Leu | Pro | Asp | Phe | Thr | Gly |
| | 25 | | | | | 30 | | | | | 35 | | | | |
| Asp | Leu | Arg | Ile | Pro | His | Val | Gly | Arg | Gly | Arg | Tyr | Glu | Phe | His | Ser |
| 40 | | | | | 45 | | | | | 50 | | | | | 55 |
| Leu | Asn | Ile | His | Ser | Cys | Glu | Leu | Leu | His | Ser | Ala | Leu | Arg | Pro | Val |

```
                              60                        65                        70
Pro  Gly  Gln  Gly  Leu  Ser  Leu  Ser  Ile  Ser  Asp  Ser  Ser  Ile  Arg  Val
               75                       80                       85

Gln  Gly  Arg  Trp  Lys  Val  Arg  Lys  Ser  Phe  Phe  Lys  Leu  Gln  Gly  Ser
               90                       95                      100

Phe  Asp  Val  Ser  Val  Lys  Gly  Ile  Ser  Ile  Ser  Val  Asn  Leu  Leu  Leu
     105                      110                      115

Gly  Ser  Glu  Ser  Ser  Gly  Arg  Pro  Thr  Val  Thr  Ala  Ser  Ser  Cys  Ser
120                      125                      130                      135

Ser  Asp  Ile  Ala  Asp  Val  Glu  Val  Asp  Met  Ser  Gly  Asp  Leu  Gly  Trp
                    140                      145                      150

Leu  Leu  Asn  Leu  Phe  His  Asn  Gln  Ile  Glu  Ser  Lys  Phe  Gln  Lys  Val
               155                      160                      165

Leu  Glu  Ser  Arg  Ile  Cys  Glu  Met  Ile  Gln  Lys  Ser  Val  Ser  Ser  Asp
          170                      175                      180

Leu  Gln  Pro  Tyr  Leu  Gln  Thr  Leu  Pro  Val  Thr  Thr  Glu  Ile  Asp  Ser
     185                      190                      195

Phe  Ala  Asp  Ile  Asp  Tyr  Ser  Leu  Val  Glu  Ala  Pro  Arg  Ala  Thr  Ala
200                      205                      210                      215

Gln  Met  Leu  Glu  Val  Met  Phe  Lys  Gly  Glu  Ile  Phe  His  Arg  Asn  His
                    220                      225                      230

Arg  Ser  Pro  Val  Thr  Leu  Leu  Ala  Ala  Val  Met  Ser  Leu  Pro  Glu  Glu
               235                      240                      245

His  Asn  Lys  Met  Val  Tyr  Phe  Ala  Ile  Ser  Asp  Tyr  Val  Phe  Asn  Thr
          250                      255                      260

Ala  Ser  Leu  Val  Tyr  His  Glu  Glu  Gly  Tyr  Leu  Asn  Phe  Ser  Ile  Thr
     265                      270                      275

Asp  Glu  Met  Ile  Pro  Pro  Asp  Ser  Asn  Ile  Arg  Leu  Thr  Thr  Lys  Ser
280                      285                      290                      295

Phe  Arg  Pro  Phe  Val  Pro  Arg  Leu  Ala  Arg  Leu  Tyr  Pro  Asn  Met  Asn
                    300                      305                      310

Leu  Glu  Leu  Gln  Gly  Ser  Val  Pro  Ser  Ala  Pro  Leu  Leu  Asn  Phe  Ser
               315                      320                      325

Pro  Gly  Asn  Leu  Ser  Val  Asp  Pro  Tyr  Met  Glu  Ile  Asp  Ala  Phe  Val
          330                      335                      340

Leu  Leu  Pro  Ser  Ser  Ser  Lys  Glu  Pro  Val  Phe  Arg  Leu  Ser  Val  Ala
     345                      350                      355

Thr  Asn  Val  Ser  Ala  Thr  Leu  Thr  Phe  Asn  Thr  Ser  Lys  Ile  Thr  Gly
360                      365                      370                      375

Phe  Leu  Lys  Pro  Gly  Lys  Val  Lys  Val  Glu  Leu  Lys  Glu  Ser  Lys  Val
                    380                      385                      390

Gly  Leu  Phe  Asn  Ala  Glu  Leu  Leu  Glu  Ala  Leu  Leu  Asn  Tyr  Tyr  Ile
               395                      400                      405

Leu  Asn  Thr  Phe  Tyr  Pro  Lys  Phe  Asn  Asp  Lys  Leu  Ala  Glu  Gly  Phe
          410                      415                      420

Pro  Leu  Pro  Leu  Leu  Lys  Arg  Val  Gln  Leu  Tyr  Asp  Leu  Gly  Leu  Gln
     425                      430                      435

Ile  His  Lys  Asp  Phe  Leu  Phe  Leu  Gly  Ala  Asn  Val  Gln  Tyr  Met  Arg
440                      445                      450                      455

Val
```

( 2 ) INFORMATION FOR SEQ ID NO:5:

( i ) SEQUENCE CHARACTERISTICS:

(A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (D) OTHER INFORMATION: "LBP-Bsm"

(xi) SEQUENCE DESCRIPTION: SEQ ID NO:5:

GAATGCAGCC AACCCCGGCT TGGTCGCCA                29

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (D) OTHER INFORMATION: "LBP-2"

(xi) SEQUENCE DESCRIPTION: SEQ ID NO:6:

CTCGAGCTAA ATCTCTGTTG TAACTGGC                 28

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (D) OTHER INFORMATION: "LBP-3"

(xi) SEQUENCE DESCRIPTION: SEQ ID NO:7:

CATGTCGACA CCATGGGGGC CTTG                     24

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (D) OTHER INFORMATION: "LBP-4"

(xi) SEQUENCE DESCRIPTION: SEQ ID NO:8:

CATGCCGCGG TCAAACTCTC ATGTA                    25

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( i i ) MOLECULE TYPE: DNA ( i x ) FEATURE:
  ( A ) NAME/KEY: misc_feature
  ( D ) OTHER INFORMATION: "LBP 241- 245"

( x i ) SEQUENCE DESCRIPTION: SEQ ID NO:9:

GTCATGAGCC TTCCT                        15

( 2 ) INFORMATION FOR SEQ ID NO:10:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i i ) MOLECULE TYPE: protein ( i x ) FEATURE:
  ( A ) NAME/KEY: misc_feature
  ( D ) OTHER INFORMATION: "LBP 241- 245"

( x i ) SEQUENCE DESCRIPTION: SEQ ID NO:10:

Val Met Ser Leu Pro
1       5

( 2 ) INFORMATION FOR SEQ ID NO:11:

( i ) SEQUENCE CHARACTERISTICS:
  ( A ) LENGTH: 1813 base pairs
  ( B ) TYPE: nucleic acid
  ( C ) STRANDEDNESS: single
  ( D ) TOPOLOGY: linear ( i i ) MOLECULE TYPE: cDNA ( i x ) FEATURE:
  ( A ) NAME/KEY: CDS
  ( B ) LOCATION: 31..1491

( i x ) FEATURE:
  ( A ) NAME/KEY: mat_peptide
  ( B ) LOCATION: 124..1491

( i x ) FEATURE:
  ( A ) NAME/KEY: misc_feature
  ( D ) OTHER INFORMATION: "BPI"

( x i ) SEQUENCE DESCRIPTION: SEQ ID NO:11:

```
CAGGCCTTGA GGTTTTGGCA GCTCTGGAGG ATG AGA GAG AAC ATG GCC AGG GGC        54
                                 Met Arg Glu Asn Met Ala Arg Gly
                                 -31 -30                      -25

CCT TGC AAC GCG CCG AGA TGG GTG TCC CTG ATG GTG CTC GTC GCC ATA        102
Pro Cys Asn Ala Pro Arg Trp Val Ser Leu Met Val Leu Val Ala Ile
            -20                 -15                     -10

GGC ACC GCC GTG ACA GCG GCC GTC AAC CCT GGC GTC GTG GTC AGG ATC        150
Gly Thr Ala Val Thr Ala Ala Val Asn Pro Gly Val Val Val Arg Ile
        -5                       1                   5

TCC CAG AAG GGC CTG GAC TAC GCC AGC CAG CAG GGG ACG GCC GCT CTG        198
Ser Gln Lys Gly Leu Asp Tyr Ala Ser Gln Gln Gly Thr Ala Ala Leu
10              15                      20                  25

CAG AAG GAG CTG AAG AGG ATC AAG ATT CCT GAC TAC TCA GAC AGC TTT        246
Gln Lys Glu Leu Lys Arg Ile Lys Ile Pro Asp Tyr Ser Asp Ser Phe
                30              35                      40

AAG ATC AAG CAT CTT GGG AAG GGG CAT TAT AGC TTC TAC AGC ATG GAC        294
Lys Ile Lys His Leu Gly Lys Gly His Tyr Ser Phe Tyr Ser Met Asp
            45              50                      55
```

| | | | | | | | | | | | | | | | |
|---|---|---|---|---|---|---|---|---|---|---|---|---|---|---|---|
| ATC | CGT | GAA | TTC | CAG | CTT | CCC | AGT | TCC | CAG | ATA | AGC | ATG | GTG | CCC | AAT | 342 |
| Ile | Arg | Glu | Phe | Gln | Leu | Pro | Ser | Ser | Gln | Ile | Ser | Met | Val | Pro | Asn |
| | | 60 | | | | 65 | | | | | 70 | | | | |

| GTG | GGC | CTT | AAG | TTC | TCC | ATC | AGC | AAC | GCC | AAT | ATC | AAG | ATC | AGC | GGG | 390 |
| Val | Gly | Leu | Lys | Phe | Ser | Ile | Ser | Asn | Ala | Asn | Ile | Lys | Ile | Ser | Gly |
| | 75 | | | | | 80 | | | | | 85 | | | | |

| AAA | TGG | AAG | GCA | CAA | AAG | AGA | TTC | TTA | AAA | ATG | AGC | GGC | AAT | TTT | GAC | 438 |
| Lys | Trp | Lys | Ala | Gln | Lys | Arg | Phe | Leu | Lys | Met | Ser | Gly | Asn | Phe | Asp |
| 90 | | | | 95 | | | | | 100 | | | | | 105 | |

| CTG | AGC | ATA | GAA | GGC | ATG | TCC | ATT | TCG | GCT | GAT | CTG | AAG | CTG | GGC | AGT | 486 |
| Leu | Ser | Ile | Glu | Gly | Met | Ser | Ile | Ser | Ala | Asp | Leu | Lys | Leu | Gly | Ser |
| | | | | 110 | | | | | 115 | | | | | 120 | |

| AAC | CCC | ACG | TCA | GGC | AAG | CCC | ACC | ATC | ACC | TGC | TCC | AGC | TGC | AGC | AGC | 534 |
| Asn | Pro | Thr | Ser | Gly | Lys | Pro | Thr | Ile | Thr | Cys | Ser | Ser | Cys | Ser | Ser |
| | | | 125 | | | | | 130 | | | | | 135 | | |

| CAC | ATC | AAC | AGT | GTC | CAC | GTG | CAC | ATC | TCA | AAG | AGC | AAA | GTC | GGG | TGG | 582 |
| His | Ile | Asn | Ser | Val | His | Val | His | Ile | Ser | Lys | Ser | Lys | Val | Gly | Trp |
| | | 140 | | | | | 145 | | | | | 150 | | | |

| CTG | ATC | CAA | CTC | TTC | CAC | AAA | AAA | ATT | GAG | TCT | GCG | CTT | CGA | AAC | AAG | 630 |
| Leu | Ile | Gln | Leu | Phe | His | Lys | Lys | Ile | Glu | Ser | Ala | Leu | Arg | Asn | Lys |
| | 155 | | | | | 160 | | | | | 165 | | | | |

| ATG | AAC | AGC | CAG | GTC | TGC | GAG | AAA | GTG | ACC | AAT | TCT | GTA | TCC | TCC | AAG | 678 |
| Met | Asn | Ser | Gln | Val | Cys | Glu | Lys | Val | Thr | Asn | Ser | Val | Ser | Ser | Lys |
| 170 | | | | 175 | | | | | 180 | | | | | 185 | |

| CTG | CAA | CCT | TAT | TTC | CAG | ACT | CTG | CCA | GTA | ATG | ACC | AAA | ATA | GAT | TCT | 726 |
| Leu | Gln | Pro | Tyr | Phe | Gln | Thr | Leu | Pro | Val | Met | Thr | Lys | Ile | Asp | Ser |
| | | | | 190 | | | | | 195 | | | | | 200 | |

| GTG | GCT | GGA | ATC | AAC | TAT | GGT | CTG | GTG | GCA | CCT | CCA | GCA | ACC | ACG | GCT | 774 |
| Val | Ala | Gly | Ile | Asn | Tyr | Gly | Leu | Val | Ala | Pro | Pro | Ala | Thr | Thr | Ala |
| | | | | 205 | | | | | 210 | | | | | 215 | |

| GAG | ACC | CTG | GAT | GTA | CAG | ATG | AAG | GGG | GAG | TTT | TAC | AGT | GAG | AAC | CAC | 822 |
| Glu | Thr | Leu | Asp | Val | Gln | Met | Lys | Gly | Glu | Phe | Tyr | Ser | Glu | Asn | His |
| | | 220 | | | | | 225 | | | | | 230 | | | |

| CAC | AAT | CCA | CCT | CCC | TTT | GCT | CCA | CCA | GTG | ATG | GAG | TTT | CCC | GCT | GCC | 870 |
| His | Asn | Pro | Pro | Pro | Phe | Ala | Pro | Pro | Val | Met | Glu | Phe | Pro | Ala | Ala |
| | 235 | | | | | 240 | | | | | 245 | | | | |

| CAT | GAC | CGC | ATG | GTA | TAC | CTG | GGC | CTC | TCA | GAC | TAC | TTC | TTC | AAC | ACA | 918 |
| His | Asp | Arg | Met | Val | Tyr | Leu | Gly | Leu | Ser | Asp | Tyr | Phe | Phe | Asn | Thr |
| 250 | | | | 255 | | | | | 260 | | | | | 265 | |

| GCC | GGG | CTT | GTA | TAC | CAA | GAG | GCT | GGG | GTC | TTG | AAG | ATG | ACC | CTT | AGA | 966 |
| Ala | Gly | Leu | Val | Tyr | Gln | Glu | Ala | Gly | Val | Leu | Lys | Met | Thr | Leu | Arg |
| | | | | 270 | | | | | 275 | | | | | 280 | |

| GAT | GAC | ATG | ATT | CCA | AAG | GAG | TCC | AAA | TTT | CGA | CTG | ACA | ACC | AAG | TTC | 1014 |
| Asp | Asp | Met | Ile | Pro | Lys | Glu | Ser | Lys | Phe | Arg | Leu | Thr | Thr | Lys | Phe |
| | | | 285 | | | | | 290 | | | | | 295 | | |

| TTT | GGA | ACC | TTC | CTA | CCT | GAG | GTG | GCC | AAG | AAG | TTT | CCC | AAC | ATG | AAG | 1062 |
| Phe | Gly | Thr | Phe | Leu | Pro | Glu | Val | Ala | Lys | Lys | Phe | Pro | Asn | Met | Lys |
| | | 300 | | | | | 305 | | | | | 310 | | | |

| ATA | CAG | ATC | CAT | GTC | TCA | GCC | TCC | ACC | CCG | CCA | CAC | CTG | TCT | GTG | CAG | 1110 |
| Ile | Gln | Ile | His | Val | Ser | Ala | Ser | Thr | Pro | Pro | His | Leu | Ser | Val | Gln |
| | 315 | | | | | 320 | | | | | 325 | | | | |

| CCC | ACC | GGC | CTT | ACC | TTC | TAC | CCT | GCC | GTG | GAT | GTC | CAG | GCC | TTT | GCC | 1158 |
| Pro | Thr | Gly | Leu | Thr | Phe | Tyr | Pro | Ala | Val | Asp | Val | Gln | Ala | Phe | Ala |
| 330 | | | | 335 | | | | | 340 | | | | | 345 | |

| GTC | CTC | CCC | AAC | TCC | TCC | CTG | GCT | TCC | CTC | TTC | CTG | ATT | GGC | ATG | CAC | 1206 |
| Val | Leu | Pro | Asn | Ser | Ser | Leu | Ala | Ser | Leu | Phe | Leu | Ile | Gly | Met | His |
| | | | | 350 | | | | | 355 | | | | | 360 | |

| ACA | ACT | GGT | TCC | ATG | GAG | GTC | AGC | GCC | GAG | TCC | AAC | AGG | CTT | GTT | GGA | 1254 |
| Thr | Thr | Gly | Ser | Met | Glu | Val | Ser | Ala | Glu | Ser | Asn | Arg | Leu | Val | Gly |
| | | | 365 | | | | | 370 | | | | | 375 | | |

```
GAG CTC AAG CTG GAT AGG CTG CTC CTG GAA CTG AAG CAC TCA AAT ATT       1302
Glu Leu Lys Leu Asp Arg Leu Leu Leu Glu Leu Lys His Ser Asn Ile
        380                 385                 390

GGC CCC TTC CCG GTT GAA TTG CTG CAG GAT ATC ATG AAC TAC ATT GTA       1350
Gly Pro Phe Pro Val Glu Leu Leu Gln Asp Ile Met Asn Tyr Ile Val
395                 400                 405

CCC ATT CTT GTG CTG CCC AGG GTT AAC GAG AAA CTA CAG AAA GGC TTC       1398
Pro Ile Leu Val Leu Pro Arg Val Asn Glu Lys Leu Gln Lys Gly Phe
410                 415                 420                 425

CCT CTC CCG ACG CCG GCC AGA GTC CAG CTC TAC AAC GTA GTG CTT CAG       1446
Pro Leu Pro Thr Pro Ala Arg Val Gln Leu Tyr Asn Val Val Leu Gln
                430                 435                 440

CCT CAC CAG AAC TTC CTG CTG TTC GGT GCA GAC GTT GTC TAT AAA           1491
Pro His Gln Asn Phe Leu Leu Phe Gly Ala Asp Val Val Tyr Lys
            445                 450                 455

TGAAGGCACC AGGGGTGCCG GGGGCTGTCA GCCGCACCTG TTCCTGATGG GCTGTGGGGC     1551
ACCGGCTGCC TTTCCCCAGG GAATCCTCTC CAGATCTTAA CCAAGAGCCC CTTGCAAACT     1611
TCTTCGACTC AGATTCAGAA ATGATCTAAA CACGAGGAAA CATTATTCAT TGGAAAAGTG     1671
CATGGTGTGT ATTTTAGGGA TTATGAGCTT CTTTCAAGGG CTAAGGCTGC AGAGATATTT     1731
CCTCCAGGAA TCGTGTTTCA ATTGTAACCA AGAAATTTCC ATTTGTGCTT CATGAAAAAA     1791
AACTTCTGGT TTTTTCATG TG                                               1813
```

( 2 ) INFORMATION FOR SEQ ID NO:12:

( i ) SEQUENCE CHARACTERISTICS:
        ( A ) LENGTH: 487 amino acids
        ( B ) TYPE: amino acid
        ( D ) TOPOLOGY: linear ( i i ) MOLECULE TYPE: protein ( i x ) FEATURE:
        ( A ) NAME/KEY: misc_feature
        ( D ) OTHER INFORMATION: "BPI"

( x i ) SEQUENCE DESCRIPTION: SEQ ID NO:12:

```
Met Arg Glu Asn Met Ala Arg Gly Pro Cys Asn Ala Pro Arg Trp Val
-31     -30                 -25                 -20

Ser Leu Met Val Leu Val Ala Ile Gly Thr Ala Val Thr Ala Ala Val
    -15             -10                  -5                   1

Asn Pro Gly Val Val Val Arg Ile Ser Gln Lys Gly Leu Asp Tyr Ala
                 5                  10                  15

Ser Gln Gln Gly Thr Ala Ala Leu Gln Lys Glu Leu Lys Arg Ile Lys
            20                  25                  30

Ile Pro Asp Tyr Ser Asp Ser Phe Lys Ile Lys His Leu Gly Lys Gly
        35                  40                  45

His Tyr Ser Phe Tyr Ser Met Asp Ile Arg Glu Phe Gln Leu Pro Ser
50                  55                  60                  65

Ser Gln Ile Ser Met Val Pro Asn Val Gly Leu Lys Phe Ser Ile Ser
                70                  75                  80

Asn Ala Asn Ile Lys Ile Ser Gly Lys Trp Lys Ala Gln Lys Arg Phe
            85                  90                  95

Leu Lys Met Ser Gly Asn Phe Asp Leu Ser Ile Glu Gly Met Ser Ile
        100                 105                 110

Ser Ala Asp Leu Lys Leu Gly Ser Asn Pro Thr Ser Gly Lys Pro Thr
    115                 120                 125

Ile Thr Cys Ser Ser Cys Ser Ser His Ile Asn Ser Val His Val His
130                 135                 140                 145
```

Ile Ser Lys Ser Lys Val Gly Trp Leu Ile Gln Leu Phe His Lys Lys
            150                     155                     160

Ile Glu Ser Ala Leu Arg Asn Lys Met Asn Ser Gln Val Cys Glu Lys
            165                     170                     175

Val Thr Asn Ser Val Ser Ser Lys Leu Gln Pro Tyr Phe Gln Thr Leu
            180                     185                     190

Pro Val Met Thr Lys Ile Asp Ser Val Ala Gly Ile Asn Tyr Gly Leu
            195                     200                     205

Val Ala Pro Pro Ala Thr Thr Ala Glu Thr Leu Asp Val Gln Met Lys
210                     215                     220                     225

Gly Glu Phe Tyr Ser Glu Asn His His Asn Pro Pro Pro Phe Ala Pro
                        230                     235                     240

Pro Val Met Glu Phe Pro Ala Ala His Asp Arg Met Val Tyr Leu Gly
                245                     250                     255

Leu Ser Asp Tyr Phe Phe Asn Thr Ala Gly Leu Val Tyr Gln Glu Ala
            260                     265                     270

Gly Val Leu Lys Met Thr Leu Arg Asp Asp Met Ile Pro Lys Glu Ser
        275                     280                     285

Lys Phe Arg Leu Thr Thr Lys Phe Phe Gly Thr Phe Leu Pro Glu Val
290                     295                     300                     305

Ala Lys Lys Phe Pro Asn Met Lys Ile Gln Ile His Val Ser Ala Ser
                310                     315                     320

Thr Pro Pro His Leu Ser Val Gln Pro Thr Gly Leu Thr Phe Tyr Pro
            325                     330                     335

Ala Val Asp Val Gln Ala Phe Ala Val Leu Pro Asn Ser Ser Leu Ala
            340                     345                     350

Ser Leu Phe Leu Ile Gly Met His Thr Thr Gly Ser Met Glu Val Ser
        355                     360                     365

Ala Glu Ser Asn Arg Leu Val Gly Glu Leu Lys Leu Asp Arg Leu Leu
370                     375                     380                     385

Leu Glu Leu Lys His Ser Asn Ile Gly Pro Phe Pro Val Glu Leu Leu
                        390                     395                     400

Gln Asp Ile Met Asn Tyr Ile Val Pro Ile Leu Val Leu Pro Arg Val
                405                     410                     415

Asn Glu Lys Leu Gln Lys Gly Phe Pro Leu Pro Thr Pro Ala Arg Val
            420                     425                     430

Gln Leu Tyr Asn Val Val Leu Gln Pro His Gln Asn Phe Leu Leu Phe
        435                     440                     445

Gly Ala Asp Val Val Tyr Lys
450                     455

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: misc_feature
        ( D ) OTHER INFORMATION: "BPI-18"

( x i ) SEQUENCE DESCRIPTION: SEQ ID NO:13:

AAGCATCTTG GGAAGGGG        18

( 2 ) INFORMATION FOR SEQ ID NO:14:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: misc_feature
        ( D ) OTHER INFORMATION: "BPI-11"

( x i ) SEQUENCE DESCRIPTION: SEQ ID NO:14:

```
TATTTTGGTC ATTACTGGCA GAGT                                              24
```

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: misc_feature
        ( D ) OTHER INFORMATION: "LBP15"

( x i ) SEQUENCE DESCRIPTION: SEQ ID NO:15:

```
CCCACAGTCA CGTGCTCCAG CTGCA                                             25
```

( 2 ) INFORMATION FOR SEQ ID NO:16:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: misc_feature
        ( D ) OTHER INFORMATION: "LBP16"

( x i ) SEQUENCE DESCRIPTION: SEQ ID NO:16:

```
GCTGGAGCAC GTGACTGTGG GCC                                               23
```

( 2 ) INFORMATION FOR SEQ ID NO:17:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: misc_feature
        ( D ) OTHER INFORMATION: "BPI Domain I"

( x i ) SEQUENCE DESCRIPTION: SEQ ID NO:17:

```
Ala Ser Gln Gln Gly Thr Ala Ala Leu Gln Lys Glu Leu Lys Arg Ile
 1               5                  10                  15
Lys Pro Asp Tyr Ser Asp Ser Phe Lys Ile Lys His
            20                  25
```

( 2 ) INFORMATION FOR SEQ ID NO:18:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: misc_feature
        ( D ) OTHER INFORMATION: "BPI Domain II"

( x i ) SEQUENCE DESCRIPTION: SEQ ID NO:18:

```
Ser  Ser  Gln  Ile  Ser  Met  Val  Pro  Asn  Val  Gly  Leu  Lys  Phe  Ser  Ile
 1               5                        10                       15
Ser  Asn  Ala  Asn  Ile  Lys  Ile  Ser  Gly  Lys  Trp  Lys  Ala  Gln  Lys  Arg
              20                        25                       30
Phe  Leu  Lys
         35
```

( 2 ) INFORMATION FOR SEQ ID NO:19:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: misc_feature
        ( D ) OTHER INFORMATION: "BPI Domain III"

( x i ) SEQUENCE DESCRIPTION: SEQ ID NO:19:

```
Val  His  Val  His  Ile  Ser  Lys  Ser  Lys  Val  Gly  Trp  Leu  Ile  Gln  Leu
 1               5                        10                       15
Phe  His  Lys  Lys  Ile  Glu  Ser  Ala  Leu  Arg  Asn  Lys
              20                        25
```

( 2 ) INFORMATION FOR SEQ ID NO:20:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: misc_feature
        ( D ) OTHER INFORMATION: "LBP Domain I"

( x i ) SEQUENCE DESCRIPTION: SEQ ID NO:20:

```
Ala  Ala  Gln  Glu  Gly  Leu  Leu  Ala  Leu  Gln  Ser  Glu  Leu  Leu  Arg  Ile
 1               5                        10                       15
Thr  Leu  Pro  Asp  Phe  Thr  Gly  Asp  Leu  Arg  Ile  Pro  His
              20                        25
```

( 2 ) INFORMATION FOR SEQ ID NO:21:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: protein ( i x ) FEATURE:
  ( A ) NAME/KEY: misc_feature
  ( D ) OTHER INFORMATION: "LBP Domain II"

( x i ) SEQUENCE DESCRIPTION: SEQ ID NO:21:

```
His  Ser  Ala  Leu  Arg  Pro  Val  Pro  Gly  Gln  Gly  Leu  Ser  Leu  Ser  Ile
 1                  5                        10                      15
Ser  Asp  Ser  Ser  Ile  Arg  Val  Gln  Gly  Arg  Trp  Lys  Val  Arg  Lys  Ser
              20                  25                        30
Phe  Phe  Lys
         35
```

( 2 ) INFORMATION FOR SEQ ID NO:22:

( i ) SEQUENCE CHARACTERISTICS:
    ( A ) LENGTH: 27 amino acids
    ( B ) TYPE: amino acid
    ( C ) STRANDEDNESS: single
    ( D ) TOPOLOGY: linear ( i i ) MOLECULE TYPE: protein ( i x ) FEATURE:
    ( A ) NAME/KEY: misc_feature
    ( D ) OTHER INFORMATION: "LBP Domain III"

( x i ) SEQUENCE DESCRIPTION: SEQ ID NO:22:

```
Val  Glu  Val  Asp  Met  Ser  Gly  Asp  Leu  Gly  Trp  Leu  Leu  Asn  Leu  Phe
 1                  5                        10                      15
His  Asn  Gln  Ile  Glu  Ser  Lys  Phe  Gln  Lys  Val
              20                  25
```

( 2 ) INFORMATION FOR SEQ ID NO:23:

( i ) SEQUENCE CHARACTERISTICS:
    ( A ) LENGTH: 76 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:23:

```
TTAAATTTTC GATATCCAAC GCCAATATTA AGATCTCCGG AAAATGGAAG GCACAAAAGC        60
GCTTCCTTAA GATGAG                                                        76
```

( 2 ) INFORMATION FOR SEQ ID NO:24:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:24:

```
CTCATCTTAA GGAAGCGCTT TTGTGCCTTC CATTTTCCGG AGATCTTAAT ATTGGCGTTG        60
GATATCGAAA AT                                                            72
```

( 2 ) INFORMATION FOR SEQ ID NO:25:

( i ) SEQUENCE CHARACTERISTICS:
    ( A ) LENGTH: 69 base pairs ( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:25:

GTGCACATTT CGAAGAGCAA AGTGGGGTGG CTGATCCAAT TGTTCCACAA AAAAATTGAG     60

AGCGCGCTG     69

( 2 ) INFORMATION FOR SEQ ID NO:26:

( i ) SEQUENCE CHARACTERISTICS:
( A ) LENGTH: 71 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:26:

CGCAGCGCGC TCTCAATTTT TTTGTGGAAC AATTGGATCA GCCACCCCAC TTTGCTCTTC     60

GAAATGTGCA C     71

( 2 ) INFORMATION FOR SEQ ID NO:27:

( i ) SEQUENCE CHARACTERISTICS:
( A ) LENGTH: 49 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:27:

GTCAGCGGGA AATGGAAGGC ACAAAAGAGA TTTTAAAAA TGCAGGGCT     49

( 2 ) INFORMATION FOR SEQ ID NO:28:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:28:

CTGCATTTTT AAAAATCTCT TTTGTGCCTT CCATTTCCCG CT     42

( 2 ) INFORMATION FOR SEQ ID NO:29:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:29:

Gln Gly Arg Trp Lys Val Arg Lys Ser Phe Phe Lys Leu
 1           5                  10

( 2 ) INFORMATION FOR SEQ ID NO:30:

( i ) SEQUENCE CHARACTERISTICS:
( A ) LENGTH: 13 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:30:

```
Ser Gly Lys Trp Lys Ala Gln Lys Arg Phe Leu Lys Met
1               5                   10
```

(2) INFORMATION FOR SEQ ID NO:31:

(i) SEQUENCE CHARACTERISTICS:
(A) LENGTH: 72 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:31:

```
CATGTCGAAG AGCAAAGTGG GGTGGCTGAT CCAACTCTTC CACAAAAAAA TTGAGTCCAA      60
ATTTCAGAAA GT                                                          72
```

(2) INFORMATION FOR SEQ ID NO:32:

(i) SEQUENCE CHARACTERISTICS:
(A) LENGTH: 68 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:32:

```
ACTTTCTGAA ATTTGGACTC AATTTTTTTG TGGAAGAGTT GGATCAGCCA CCCCACTTTG      60
CTCTTCGA                                                               68
```

(2) INFORMATION FOR SEQ ID NO:33:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:33:

```
Gly Asp Leu Gly Trp Leu Leu Asn Leu Phe His Asn Gln
1               5                   10
```

(2) INFORMATION FOR SEQ ID NO:34:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:34:

```
Lys Ser Lys Val Gly Trp Leu Ile Gln Leu Phe His Lys Lys
1               5                   10
```

(2) INFORMATION FOR SEQ ID NO:35:

( i ) SEQUENCE CHARACTERISTICS:
     ( A ) LENGTH: 40 base pairs
     ( B ) TYPE: nucleic acid
     ( C ) STRANDEDNESS: single
     ( D ) TOPOLOGY: linear ( i i ) MOLECULE TYPE: DNA ( x i ) SEQUENCE DESCRIPTION: SEQ ID NO:35:

ATTCGTGTAC AGGGCAGGTG GAAGGTGCGC AAGTCATTCT    40

( 2 ) INFORMATION FOR SEQ ID NO:36:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:36:

TTAAAGAATG ACTTGCGCAC CTTCCACCTG CCCTGTACAC GAAT    44

( 2 ) INFORMATION FOR SEQ ID NO:37:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:37:

Lys Ile Ser Gly Lys Trp Lys Ala Gln Lys Arg Phe Leu Lys
1               5                   10

( 2 ) INFORMATION FOR SEQ ID NO:38:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:38:

Arg Val Gln Gly Arg Trp Lys Val Arg Lys Ser Phe Phe Lys
1               5                   10

( 2 ) INFORMATION FOR SEQ ID NO:39:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:39:

CGGGAGACTT GGGGTGGCTG TTGAACCTCT TCCACAACCA GATTGAGAG    49

( 2 ) INFORMATION FOR SEQ ID NO:40:

( i ) SEQUENCE CHARACTERISTICS:
        ( A ) LENGTH: 51 base pairs
        ( B ) TYPE: nucleic acid (C) STRANDEDNESS: single
(D) TOPOLOGY: linear (ii) MOLECULE TYPE: DNA (xi) SEQUENCE DESCRIPTION: SEQ ID NO:40:

CGCGCTCTCA ATCTGGTTGT GGAAGAGGTT CAACAGCCAC CCCAAGTCTC C 51

(2) INFORMATION FOR SEQ ID NO:41:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:41:

Lys Ser Lys Val Gly Trp Leu Ile Gln Leu Phe His Lys Lys
1               5                   10

(2) INFORMATION FOR SEQ ID NO:42:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:42:

Gly Asp Leu Gly Trp Leu Leu Asn Leu Phe His Asn Gln
1               5                   10

(2) INFORMATION FOR SEQ ID NO:43:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:43:

Gly Gln Gly Leu Ser Leu Ser Ile Ser Asp Ser Ser Ile Arg Val Gln
1               5                   10                  15

Gly Arg Trp Lys Val Arg Lys Ser Phe Phe Lys
                20                  25

(2) INFORMATION FOR SEQ ID NO:44:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:44:

Asp Val Glu Val Asp Met Ser Gly Asp Ser Gly Trp Leu Leu Asn Leu
1               5                   10                  15

Phe His Asn Gln Ile Glu
                20

(2) INFORMATION FOR SEQ ID NO:45:

(i) SEQUENCE CHARACTERISTICS:
        (A) LENGTH: 197 amino acids
        (B) TYPE: amino acid
        (D) TOPOLOGY: linear (ii) MOLECULE TYPE: protein (ix) FEATURE:
        (A) NAME/KEY: misc_feature
        (D) OTHER INFORMATION: "rLBP25"

(xi) SEQUENCE DESCRIPTION: SEQ ID NO:45:

```
Ala Asn Pro Gly Leu Val Ala Arg Ile Thr Asp Lys Gly Leu Gln Tyr
 1               5                  10                  15

Ala Ala Gln Glu Gly Leu Leu Ala Leu Gln Ser Glu Leu Leu Arg Ile
            20                  25                  30

Thr Leu Pro Asp Phe Thr Gly Asp Leu Arg Ile Pro His Val Gly Arg
        35                  40                  45

Gly Arg Tyr Glu Phe His Ser Leu Asn Ile His Ser Cys Glu Leu Leu
    50                  55                  60

His Ser Ala Leu Arg Pro Val Pro Gly Gln Gly Leu Ser Leu Ser Ile
 65                  70                  75                  80

Ser Asp Ser Ser Ile Arg Val Gln Gly Arg Trp Lys Val Arg Lys Ser
                85                  90                  95

Phe Phe Lys Leu Gln Gly Ser Phe Asp Val Ser Val Lys Gly Ile Ser
               100                 105                 110

Ile Ser Val Asn Leu Leu Leu Gly Ser Glu Ser Ser Gly Arg Pro Thr
           115                 120                 125

Val Thr Cys Ser Ser Cys Ser Ser Asp Ile Ala Asp Val Glu Val Asp
       130                 135                 140

Met Ser Gly Asp Leu Gly Trp Leu Leu Asn Leu Phe His Asn Gln Ile
145                 150                 155                 160

Glu Ser Lys Phe Gln Lys Val Leu Glu Ser Arg Ile Cys Glu Met Ile
               165                 170                 175

Gln Lys Ser Val Ser Ser Asp Leu Gln Pro Tyr Leu Gln Thr Leu Pro
           180                 185                 190

Val Thr Thr Glu Ile
       195
```

(2) INFORMATION FOR SEQ ID NO:46:

(i) SEQUENCE CHARACTERISTICS:
        (A) LENGTH: 199 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:46:

```
Ala Asn Pro Gly Leu Val Ala Arg Ile Thr Asp Lys Gly Leu Gln Tyr
 1               5                  10                  15

Ala Ala Gln Glu Gly Leu Leu Ala Leu Gln Ser Glu Leu Leu Arg Ile
            20                  25                  30

Thr Leu Pro Asp Phe Thr Gly Asp Leu Arg Ile Lys His Leu Gly Lys
        35                  40                  45

Gly His Tyr Ser Phe Tyr Ser Met Asp Ile Arg Glu Phe Gln Leu Pro
    50                  55                  60

Ser Ser Gln Ile Ser Met Val Pro Asn Val Gly Leu Lys Phe Ser Ile
```

```
     65                        70                         75                        80

Ser   Asn   Ala   Asn   Ile   Lys   Ile   Ser   Gly   Lys   Trp   Lys   Ala   Gln   Lys   Arg
                           85                         90                        95

Phe   Leu   Lys   Met   Ser   Gly   Asn   Phe   Asp   Leu   Ser   Ile   Glu   Gly   Met   Ser
                     100                        105                       110

Ile   Ser   Ala   Asp   Leu   Lys   Leu   Gly   Ser   Asn   Pro   Thr   Ser   Gly   Lys   Pro
                     115                        120                       125

Thr   Ile   Thr   Cys   Ser   Ser   Cys   Ser   Ser   His   Ile   Asn   Ser   Val   His   Val
               130                        135                       140

His   Ile   Ser   Lys   Ser   Lys   Val   Gly   Trp   Leu   Ile   Gln   Leu   Phe   His   Lys
   145                           150                        155                       160

Lys   Ile   Glu   Ser   Ala   Leu   Arg   Asn   Lys   Met   Asn   Ser   Gln   Val   Cys   Glu
                           165                        170                       175

Lys   Val   Thr   Asn   Ser   Val   Ser   Ser   Lys   Leu   Gln   Pro   Tyr   Phe   Gln   Thr
                     180                        185                       190

Leu   Pro   Val   Met   Thr   Lys   Ile
                     195
```

( 2 ) INFORMATION FOR SEQ ID NO:47:

( i ) SEQUENCE CHARACTERISTICS:
        ( A ) LENGTH: 199 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:47:

```
   Val   Asn   Pro   Gly   Val   Val   Val   Arg   Ile   Ser   Gln   Lys   Gly   Leu   Asp   Tyr
   1                       5                          10                        15

Ala   Ser   Gln   Gln   Gly   Thr   Ala   Ala   Leu   Gln   Lys   Glu   Leu   Lys   Arg   Ile
                     20                         25                        30

Lys   Ile   Pro   Asp   Tyr   Ser   Asp   Ser   Phe   Lys   Ile   Lys   His   Leu   Gly   Lys
                     35                         40                        45

Gly   His   Tyr   Ser   Phe   Tyr   Ser   Met   Asp   Ile   Arg   Glu   Phe   Gln   Leu   Pro
               50                         55                        60

Ser   Ser   Gln   Ile   Ser   Met   Val   Pro   Asn   Val   Gly   Leu   Lys   Phe   Ser   Ile
   65                          70                         75                        80

Ser   Asn   Ala   Asn   Ile   Lys   Ile   Ser   Gly   Lys   Trp   Lys   Ala   Gln   Lys   Arg
                           85                         90                        95

Phe   Leu   Lys   Met   Ser   Gly   Asn   Phe   Asp   Leu   Ser   Ile   Glu   Gly   Met   Ser
                     100                        105                       110

Ile   Ser   Ala   Asp   Leu   Lys   Leu   Gly   Ser   Asn   Pro   Thr   Ser   Gly   Lys   Pro
                     115                        120                       125

Thr   Ile   Thr   Cys   Ser   Ser   Cys   Ser   Ser   His   Ile   Asn   Ser   Val   His   Val
               130                        135                       140

His   Ile   Ser   Lys   Ser   Lys   Val   Gly   Trp   Leu   Ile   Gln   Leu   Phe   His   Asn
   145                           150                        155                       160

Gln   Ile   Glu   Ser   Lys   Phe   Gln   Lys   Val   Leu   Glu   Ser   Arg   Ile   Cys   Glu
                           165                        170                       175

Met   Ile   Gln   Lys   Ser   Val   Ser   Ser   Asp   Leu   Gln   Pro   Tyr   Leu   Gln   Thr
                     180                        185                       190

Leu   Pro   Val   Thr   Thr   Glu   Ile
                     195
```

( 2 ) INFORMATION FOR SEQ ID NO:48:

( i ) SEQUENCE CHARACTERISTICS:
  ( A ) LENGTH: 199 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:48:

```
Ala Asn Pro Gly Leu Val Ala Arg Ile Thr Asp Lys Gly Leu Gln Tyr
 1               5                  10                  15

Ala Ala Gln Glu Gly Leu Leu Ala Leu Gln Ser Glu Leu Leu Arg Ile
             20                  25                  30

Thr Leu Pro Asp Phe Thr Gly Asp Leu Arg Ile Lys His Leu Gly Lys
             35                  40                  45

Gly His Tyr Ser Phe Tyr Ser Met Asp Ile Arg Glu Phe Gln Leu Pro
         50                  55                  60

Ser Ser Gln Ile Ser Met Val Pro Asn Val Gly Leu Lys Phe Ser Ile
 65                  70                  75                  80

Ser Asn Ala Asn Ile Lys Ile Ser Gly Lys Trp Lys Ala Gln Lys Arg
                 85                  90                  95

Phe Leu Lys Met Ser Gly Asn Phe Asp Leu Ser Ile Glu Gly Met Ser
                100                 105                 110

Ile Ser Ala Asp Leu Lys Leu Gly Ser Asn Pro Thr Ser Gly Lys Pro
            115                 120                 125

Thr Ile Thr Cys Ser Ser Cys Ser Ser His Ile Asn Ser Val His Val
        130                 135                 140

His Ile Ser Lys Ser Lys Val Gly Trp Leu Ile Gln Leu Phe His Asn
145                 150                 155                 160

Gln Ile Glu Ser Lys Phe Gln Lys Val Leu Glu Ser Arg Ile Cys Glu
                165                 170                 175

Met Ile Gln Lys Ser Val Ser Ser Asp Leu Gln Pro Tyr Leu Gln Thr
                180                 185                 190

Leu Pro Val Thr Thr Glu Ile
            195
```

( 2 ) INFORMATION FOR SEQ ID NO:49:

( i ) SEQUENCE CHARACTERISTICS:
  ( A ) LENGTH: 198 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:49:

```
Val Asn Pro Gly Val Val Val Arg Ile Ser Gln Lys Gly Leu Asp Tyr
 1               5                  10                  15

Ala Ser Gln Gln Gly Thr Ala Ala Leu Gln Lys Glu Leu Lys Arg Ile
             20                  25                  30

Lys Ile Pro Asp Tyr Ser Asp Ser Phe Lys Ile Lys His Leu Gly Lys
             35                  40                  45

Gly His Tyr Ser Phe Tyr Ser Met Asp Ile Arg Glu Phe Gln Leu Pro
         50                  55                  60

Ser Ser Gln Ile Ser Met Val Pro Asn Val Gly Leu Lys Phe Ser Ile
 65                  70                  75                  80

Ser Asn Ala Asn Ile Lys Ile Ser Gly Lys Trp Lys Ala Gln Lys Arg
                 85                  90                  95
```

```
Phe  Leu  Lys  Met  Ser  Gly  Asn  Phe  Asp  Leu  Ser  Ile  Glu  Gly  Met  Ser
               100                 105                      110

Ile  Ser  Ala  Asp  Leu  Lys  Leu  Gly  Ser  Asn  Pro  Thr  Ser  Gly  Lys  Pro
               115                 120                      125

Thr  Ile  Thr  Cys  Ser  Ser  Cys  Ser  Ser  Asp  Ile  Ala  Asp  Val  Glu  Val
               130                 135                      140

Asp  Met  Ser  Gly  Asp  Leu  Gly  Trp  Leu  Leu  Asn  Leu  Phe  His  Asn  Gln
145                      150                      155                      160

Ile  Glu  Ser  Lys  Phe  Gln  Lys  Val  Leu  Glu  Ser  Arg  Ile  Cys  Glu  Met
               165                 170                      175

Ile  Gln  Lys  Ser  Val  Ser  Ser  Asp  Leu  Gln  Pro  Tyr  Leu  Gln  Thr  Leu
               180                 185                      190

Pro  Val  Thr  Thr  Glu  Ile
               195
```

( 2 ) INFORMATION FOR SEQ ID NO:50:

( i ) SEQUENCE CHARACTERISTICS:
        ( A ) LENGTH: 198 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:50:

```
Val  Asn  Pro  Gly  Val  Val  Arg  Ile  Ser  Gln  Lys  Gly  Leu  Asp  Tyr
1              5                   10                       15

Ala  Ser  Gln  Gln  Gly  Thr  Ala  Ala  Leu  Gln  Ser  Glu  Leu  Leu  Arg  Ile
               20                  25                       30

Thr  Leu  Pro  Asp  Phe  Thr  Gly  Asp  Leu  Arg  Ile  Pro  His  Val  Gly  Arg
               35                  40                       45

Gly  Arg  Tyr  Glu  Phe  His  Ser  Leu  Asn  Ile  His  Ser  Cys  Glu  Leu  Leu
          50                  55                       60

His  Ser  Ala  Leu  Arg  Pro  Val  Pro  Gly  Gln  Gly  Leu  Ser  Leu  Ser  Ile
65                       70                  75                            80

Ser  Asp  Ser  Ser  Ile  Arg  Val  Gln  Gly  Arg  Trp  Lys  Val  Arg  Lys  Ser
               85                  90                       95

Phe  Phe  Lys  Leu  Gln  Gly  Ser  Phe  Asp  Val  Ser  Val  Lys  Gly  Ile  Ser
               100                 105                      110

Ile  Ser  Val  Asn  Leu  Leu  Leu  Gly  Ser  Glu  Ser  Ser  Gly  Arg  Pro  Thr
               115                 120                      125

Val  Thr  Ala  Ser  Ser  Cys  Ser  Ser  His  Ile  Asn  Ser  Val  His  Val  His
          130                 135                      140

Ile  Ser  Lys  Ser  Lys  Val  Gly  Trp  Leu  Ile  Gln  Leu  Phe  His  Lys  Lys
145                      150                      155                      160

Ile  Glu  Ser  Ala  Leu  Arg  Asn  Lys  Met  Asn  Ser  Gln  Val  Cys  Glu  Lys
               165                 170                      175

Val  Thr  Asn  Ser  Val  Ser  Ser  Lys  Leu  Gln  Pro  Tyr  Phe  Gln  Thr  Leu
               180                 185                      190

Pro  Val  Met  Thr  Lys  Ile
               195
```

( 2 ) INFORMATION FOR SEQ ID NO:51:

( i ) SEQUENCE CHARACTERISTICS:
        ( A ) LENGTH: 197 amino acids
        ( B ) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO:51:

```
Ala Asn Pro Gly Leu Val Ala Arg Ile Thr Asp Lys Gly Leu Gln Tyr
1               5                   10                  15

Ala Ala Gln Glu Gly Leu Leu Ala Leu Gln Ser Glu Leu Leu Arg Ile
            20                  25                  30

Thr Leu Pro Asp Phe Thr Gly Asp Leu Arg Ile Pro His Val Gly Arg
            35                  40                  45

Gly Arg Tyr Glu Phe His Ser Leu Asn Ile His Ser Cys Glu Leu Leu
        50                  55                  60

His Ser Ala Leu Arg Pro Val Pro Gly Gln Gly Leu Ser Leu Ser Ile
65                  70                  75                  80

Ser Asp Ser Ser Ile Arg Val Ser Gly Lys Trp Lys Ala Gln Lys Arg
                85                  90                  95

Phe Leu Lys Met Gln Gly Ser Phe Asp Val Ser Val Lys Gly Ile Ser
            100                 105                 110

Ile Ser Val Asn Leu Leu Leu Gly Ser Glu Ser Ser Gly Arg Pro Thr
            115                 120                 125

Val Thr Ala Ser Ser Cys Ser Ser Asp Ile Ala Asp Val Glu Val Asp
        130                 135                 140

Met Ser Gly Asp Leu Gly Trp Leu Leu Asn Leu Phe His Asn Gln Ile
145                 150                 155                 160

Glu Ser Lys Phe Gln Lys Val Leu Glu Ser Arg Ile Cys Glu Met Ile
                165                 170                 175

Gln Lys Ser Val Ser Ser Asp Leu Gln Pro Tyr Leu Gln Thr Leu Pro
            180                 185                 190

Val Thr Thr Glu Ile
            195
```

( 2 ) INFORMATION FOR SEQ ID NO:52:

( i ) SEQUENCE CHARACTERISTICS:
    ( A ) LENGTH: 198 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:52:

```
Ala Asn Pro Gly Leu Val Ala Arg Ile Thr Asp Lys Gly Leu Gln Tyr
1               5                   10                  15

Ala Ala Gln Glu Gly Leu Leu Ala Leu Gln Ser Glu Leu Leu Arg Ile
            20                  25                  30

Thr Leu Pro Asp Phe Thr Gly Asp Leu Arg Ile Pro His Val Gly Arg
            35                  40                  45

Gly Arg Tyr Glu Phe His Ser Leu Asn Ile His Ser Cys Glu Leu Leu
        50                  55                  60

His Ser Ala Leu Arg Pro Val Pro Gly Gln Gly Leu Ser Leu Ser Ile
65                  70                  75                  80

Ser Asp Ser Ser Ile Arg Val Gln Gly Arg Trp Lys Val Arg Lys Ser
                85                  90                  95

Phe Phe Lys Leu Gln Gly Ser Phe Asp Val Ser Val Lys Gly Ile Ser
            100                 105                 110
```

| Ile | Ser | Val | Asn | Leu | Leu | Leu | Gly | Ser | Glu | Ser | Ser | Gly | Arg | Pro | Thr |
|---|---|---|---|---|---|---|---|---|---|---|---|---|---|---|---|
| | | 115 | | | | | 120 | | | | | 125 | | | |
| Val | Thr | Ala | Ser | Ser | Cys | Ser | Ser | Asp | Ile | Ala | Asp | Val | Glu | Val | Asp |
| | 130 | | | | | 135 | | | | | 140 | | | | |
| Met | Ser | Lys | Ser | Lys | Val | Gly | Trp | Leu | Ile | Gln | Leu | Phe | His | Lys | Lys |
| 145 | | | | | 150 | | | | | 155 | | | | | 160 |
| Ile | Glu | Ser | Lys | Phe | Gln | Lys | Val | Leu | Glu | Ser | Arg | Ile | Cys | Glu | Met |
| | | | | 165 | | | | | 170 | | | | | 175 | |
| Ile | Gln | Lys | Ser | Val | Ser | Ser | Asp | Leu | Gln | Pro | Tyr | Leu | Gln | Thr | Leu |
| | | | 180 | | | | | 185 | | | | | 190 | | |
| Pro | Val | Thr | Thr | Glu | Ile | | | | | | | | | | |
| | | | | 195 | | | | | | | | | | | |

(2) INFORMATION FOR SEQ ID NO:53:

(i) SEQUENCE CHARACTERISTICS:
  (A) LENGTH: 198 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:53:

| Ala | Asn | Pro | Gly | Leu | Val | Ala | Arg | Ile | Thr | Asp | Lys | Gly | Leu | Gln | Tyr |
|---|---|---|---|---|---|---|---|---|---|---|---|---|---|---|---|
| 1 | | | | 5 | | | | | 10 | | | | | 15 | |
| Ala | Ala | Gln | Glu | Gly | Leu | Leu | Ala | Leu | Gln | Ser | Glu | Leu | Leu | Arg | Ile |
| | | | 20 | | | | | 25 | | | | | 30 | | |
| Thr | Leu | Pro | Asp | Phe | Thr | Gly | Asp | Leu | Arg | Ile | Pro | His | Val | Gly | Arg |
| | | | 35 | | | | | 40 | | | | | 45 | | |
| Gly | Arg | Tyr | Glu | Phe | His | Ser | Leu | Asn | Ile | His | Ser | Cys | Glu | Leu | Leu |
| | | 50 | | | | | 55 | | | | | 60 | | | |
| His | Ser | Ala | Leu | Arg | Pro | Val | Pro | Gly | Gln | Gly | Leu | Ser | Leu | Ser | Ile |
| 65 | | | | | 70 | | | | | 75 | | | | | 80 |
| Ser | Asp | Ser | Ser | Ile | Arg | Val | Ser | Gly | Lys | Trp | Lys | Ala | Gln | Lys | Arg |
| | | | | 85 | | | | | 90 | | | | | 95 | |
| Phe | Leu | Lys | Met | Gln | Gly | Ser | Phe | Asp | Val | Ser | Val | Lys | Gly | Ile | Ser |
| | | | 100 | | | | | 105 | | | | | 110 | | |
| Ile | Ser | Val | Asn | Leu | Leu | Leu | Gly | Ser | Glu | Ser | Ser | Gly | Arg | Pro | Thr |
| | | 115 | | | | | 120 | | | | | 125 | | | |
| Val | Thr | Ala | Ser | Ser | Cys | Ser | Ser | Asp | Ile | Ala | Asp | Val | Glu | Val | Asp |
| | 130 | | | | | 135 | | | | | 140 | | | | |
| Met | Ser | Lys | Ser | Lys | Val | Gly | Trp | Leu | Ile | Gln | Leu | Phe | His | Lys | Lys |
| 145 | | | | | 150 | | | | | 155 | | | | | 160 |
| Ile | Glu | Ser | Lys | Phe | Gln | Lys | Val | Leu | Glu | Ser | Arg | Ile | Cys | Glu | Met |
| | | | | 165 | | | | | 170 | | | | | 175 | |
| Ile | Gln | Lys | Ser | Val | Ser | Ser | Asp | Leu | Gln | Pro | Tyr | Leu | Gln | Thr | Leu |
| | | | 180 | | | | | 185 | | | | | 190 | | |
| Pro | Val | Thr | Thr | Glu | Ile | | | | | | | | | | |
| | | | | 195 | | | | | | | | | | | |

(2) INFORMATION FOR SEQ ID NO:54:

(i) SEQUENCE CHARACTERISTICS:
  (A) LENGTH: 199 amino acids
  (B) TYPE: amino acid
  (C) STRANDEDNESS: single
  (D) TOPOLOGY: linear (ii) MOLECULE TYPE: protein ( x i ) SEQUENCE DESCRIPTION: SEQ ID NO:54:

```
Val Asn Pro Gly Val Val Val Arg Ile Ser Gln Lys Gly Leu Asp Tyr
1               5                   10                  15
Ala Ser Gln Gln Gly Thr Ala Ala Leu Gln Lys Glu Leu Lys Arg Ile
            20                  25                  30
Lys Ile Pro Asp Tyr Ser Asp Ser Phe Lys Ile Lys His Leu Gly Lys
        35                  40                  45
Gly His Tyr Ser Phe Tyr Ser Met Asp Ile Arg Glu Phe Gln Leu Pro
    50                  55                  60
Ser Ser Gln Ile Ser Met Val Pro Asn Val Gly Leu Lys Phe Ser Ile
65                  70                  75                  80
Ser Asn Ala Asn Ile Arg Val Gln Gly Arg Trp Lys Val Arg Lys Ser
                85                  90                  95
Phe Phe Lys Met Ser Gly Asn Phe Asp Leu Ser Ile Glu Gly Met Ser
            100                 105                 110
Ile Ser Ala Asp Leu Lys Leu Gly Ser Asn Pro Thr Ser Gly Lys Pro
            115                 120                 125
Thr Ile Thr Cys Ser Ser Cys Ser Ser His Ile Asn Ser Val His Val
    130                 135                 140
His Ile Ser Lys Ser Lys Val Gly Trp Leu Ile Gln Leu Phe His Lys
145                 150                 155                 160
Lys Ile Glu Ser Ala Leu Arg Asn Lys Met Asn Ser Gln Val Cys Glu
                165                 170                 175
Lys Val Thr Asn Ser Val Ser Ser Lys Leu Gln Pro Tyr Phe Gln Thr
                180                 185                 190
Leu Pro Val Met Thr Lys Ile
            195
```

( 2 ) INFORMATION FOR SEQ ID NO:55:

( i ) SEQUENCE CHARACTERISTICS:
        ( A ) LENGTH: 198 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:55:

```
Val Asn Pro Gly Val Val Val Arg Ile Ser Gln Lys Gly Leu Asp Tyr
1               5                   10                  15
Ala Ser Gln Gln Gly Thr Ala Ala Leu Gln Lys Glu Leu Lys Arg Ile
            20                  25                  30
Lys Ile Pro Asp Tyr Ser Asp Ser Phe Lys Ile Lys His Leu Gly Lys
        35                  40                  45
Gly His Tyr Ser Phe Tyr Ser Met Asp Ile Arg Glu Phe Gln Leu Pro
    50                  55                  60
Ser Ser Gln Ile Ser Met Val Pro Asn Val Gly Leu Lys Phe Ser Ile
65                  70                  75                  80
Ser Asn Ala Asn Ile Lys Ile Ser Gly Lys Trp Lys Ala Gln Lys Arg
                85                  90                  95
Phe Leu Lys Met Ser Gly Asn Phe Asp Leu Ser Ile Glu Gly Met Ser
            100                 105                 110
Ile Ser Ala Asp Leu Lys Leu Gly Ser Asn Pro Thr Ser Gly Lys Pro
            115                 120                 125
Thr Ile Thr Cys Ser Ser Cys Ser Ser His Ile Asn Ser Val His Val
```

|     |     |     |     |     | 130 |     |     |     |     | 135 |     |     |     |     | 140 |     |     |     |     |
| --- | --- | --- | --- | --- | --- | --- | --- | --- | --- | --- | --- | --- | --- | --- | --- | --- | --- | --- | --- |
| His | Ile | Ser | Gly | Asp | Leu | Gly | Trp | Leu | Leu | Asn | Leu | Phe | His | Asn | Gln |
| 145 |     |     |     |     | 150 |     |     |     |     | 155 |     |     |     |     | 160 |
| Ile | Glu | Ser | Ala | Leu | Arg | Asn | Lys | Met | Asn | Ser | Gln | Val | Cys | Glu | Lys |
|     |     |     |     | 165 |     |     |     |     | 170 |     |     |     |     | 175 |     |
| Val | Thr | Asn | Ser | Val | Ser | Ser | Lys | Leu | Gln | Pro | Tyr | Phe | Gln | Thr | Leu |
|     |     |     | 180 |     |     |     |     | 185 |     |     |     |     | 190 |     |     |
| Pro | Val | Met | Thr | Lys | Ile |
|     |     | 195 |

( 2 ) INFORMATION FOR SEQ ID NO:56:

( i ) SEQUENCE CHARACTERISTICS:
( A ) LENGTH: 198 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:56:

| Val | Asn | Pro | Gly | Val | Val | Arg | Ile | Ser | Gln | Lys | Gly | Leu | Asp | Tyr |
| --- | --- | --- | --- | --- | --- | --- | --- | --- | --- | --- | --- | --- | --- | --- |
| 1 |     |     |     | 5 |     |     |     |     | 10 |     |     |     |     | 15 |
| Ala | Ser | Gln | Gln | Gly | Thr | Ala | Ala | Leu | Gln | Lys | Glu | Leu | Lys | Arg | Ile |
|     |     |     | 20 |     |     |     |     | 25 |     |     |     |     | 30 |     |     |
| Lys | Ile | Pro | Asp | Tyr | Ser | Asp | Ser | Phe | Lys | Ile | Lys | His | Leu | Gly | Lys |
|     |     | 35 |     |     |     |     | 40 |     |     |     |     | 45 |     |     |     |
| Gly | His | Tyr | Ser | Phe | Tyr | Ser | Met | Asp | Ile | Arg | Glu | Phe | Gln | Leu | Pro |
|     | 50 |     |     |     |     | 55 |     |     |     |     | 60 |
| Ser | Ser | Gln | Ile | Ser | Met | Val | Pro | Asn | Val | Gly | Leu | Lys | Phe | Ser | Ile |
| 65 |     |     |     |     | 70 |     |     |     |     | 75 |     |     |     |     | 80 |
| Ser | Asn | Ala | Asn | Ile | Arg | Val | Gln | Gly | Arg | Trp | Lys | Val | Arg | Lys | Ser |
|     |     |     |     | 85 |     |     |     |     | 90 |     |     |     |     | 95 |
| Phe | Phe | Lys | Met | Ser | Gly | Asn | Phe | Asp | Leu | Ser | Ile | Glu | Gly | Met | Ser |
|     |     |     | 100 |     |     |     |     | 105 |     |     |     |     | 110 |
| Ile | Ser | Ala | Asp | Leu | Lys | Leu | Gly | Ser | Asn | Pro | Thr | Ser | Gly | Lys | Pro |
|     |     | 115 |     |     |     |     | 120 |     |     |     |     | 125 |
| Thr | Ile | Thr | Cys | Ser | Ser | Cys | Ser | Ser | His | Ile | Asn | Ser | Val | His | Val |
|     | 130 |     |     |     |     | 135 |     |     |     |     | 140 |
| His | Ile | Ser | Gly | Asp | Leu | Gly | Trp | Leu | Leu | Asn | Leu | Phe | His | Asn | Gln |
| 145 |     |     |     |     | 150 |     |     |     |     | 155 |     |     |     |     | 160 |
| Ile | Glu | Ser | Ala | Leu | Arg | Asn | Lys | Met | Asn | Ser | Gln | Val | Cys | Glu | Lys |
|     |     |     |     | 165 |     |     |     |     | 170 |     |     |     |     | 175 |
| Val | Thr | Asn | Ser | Val | Ser | Ser | Lys | Leu | Gln | Pro | Tyr | Phe | Gln | Thr | Leu |
|     |     |     | 180 |     |     |     |     | 185 |     |     |     |     | 190 |
| Pro | Val | Met | Thr | Lys | Ile |
|     |     | 195 |

What is claimed is:

1. A lipopolysaccharide binding protein (LBP) derivative hybrid protein consisting of an LBP amino acid sequence selected from within the amino-terminal half of LBP wherein at least a portion of the LBP sequences SEQ ID NO:20, SEQ ID NO:21, or SEQ ID NO:22 is respectively replaced with at least a portion effective for endotoxin binding of the bactericidal/permeability-increasing (BPI) sequences SEQ ID NO:17, SEQ ID NO:18, or SEQ ID NO:19.

2. The hybrid protein according to claim 1 which is LBP(1-87)/BPI(88-100)/LBP(101-197) (SEQ ID NO:51).

3. The hybrid protein according to claim 1 which is LBP(1-146)/BPI(148-161)/LBP(160-197) (SEQ ID NO:52).

4. The hybrid protein according to claim 1 which is LBP(1-87)/BPI(88-100)/LBP(101-146)/BPI(148-161)/LBP(160-197) (SEQ ID NO:53).

5. A DNA sequence consisting of a DNA encoding an LBP derivative hybrid protein according to claim 1.

6. A DNA vector comprising the DNA sequence according to claim 5.

7. A host cell stably transformed or transfected with a DNA sequence according to claim 5 in a manner allowing expression in the host cell of the protein encoded thereby.

8. A pharmaceutical composition comprising an LBP derivative hybrid protein according to claim 1 and a pharmaceutically acceptable diluent, adjuvant or carrier.

9. A method of treating a gram-negative bacterial infection comprising administering an LBP derivative hybrid protein of claim 1.

10. The method of claim 9 wherein the LBP derivative hybrid protein is administered at a dosage of from about 0.1 mg/kg to about 100 mg/kg of body weight.

* * * * *